US007678830B2

(12) United States Patent
Honda et al.

(10) Patent No.: US 7,678,830 B2
(45) Date of Patent: Mar. 16, 2010

(54) TRICYCLIC-BIS-ENONE DERIVATIVES AND METHODS OF USE THEREOF

(75) Inventors: Tadashi Honda, Hanover, NH (US); Frank G. Favaloro, Norfolk, MA (US); Gordon W. Gribble, Lebanon, NH (US); Michael B. Sporn, Tunbridge, VT (US); Nanjoo Suh, White River Junction, VT (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 11/672,449

(22) Filed: Feb. 7, 2007

(65) Prior Publication Data

US 2007/0155742 A1 Jul. 5, 2007

Related U.S. Application Data

(62) Division of application No. 10/345,053, filed on Jan. 15, 2003, now Pat. No. 7,176,237.

(60) Provisional application No. 60/348,594, filed on Jan. 15, 2002, provisional application No. 60/376,040, filed on Apr. 26, 2002, provisional application No. 60/402,966, filed on Aug. 13, 2002.

(51) Int. Cl.
*A61K 31/275* (2006.01)
*C07C 255/47* (2006.01)

(52) U.S. Cl. ...................... 514/519; 558/429

(58) Field of Classification Search ............... 514/519
See application file for complete search history.

(56) References Cited

U.S. PATENT DOCUMENTS

| | | | | |
|---|---|---|---|---|
| 4,395,423 | A | 7/1983 | Neumann | 424/304 |
| 4,808,614 | A | 2/1989 | Hertel | 514/45 |
| 5,013,649 | A | 5/1991 | Wang et al. | 435/69.1 |
| 5,064,823 | A | 11/1991 | Lee et al. | 514/198 |
| 5,401,838 | A | 3/1995 | Chou | 536/281 |
| 5,426,183 | A | 6/1995 | Kjell | 536/285.5 |
| 5,464,826 | A | 11/1995 | Grindey et al. | 514/50 |
| 5,521,294 | A | 5/1996 | Wildfeuer | 536/187 |
| 5,597,124 | A | 1/1997 | Kessel et al. | 241/30 |
| 5,603,958 | A | 2/1997 | Morein et al. | 424/489 |
| 5,606,048 | A | 2/1997 | Chou et al. | 536/271.1 |
| 5,972,703 | A | 10/1999 | Long et al. | 435/372 |
| 6,025,395 | A | 2/2000 | Breitner et al. | 514/570 |
| 6,303,569 | B1 | 10/2001 | Greenwald et al. | 514/2 |
| 6,326,507 | B1 | 12/2001 | Gribble et al. | 558/415 |
| 6,485,756 | B1 | 11/2002 | Aust et al. | 424/725 |
| 6,974,801 | B2 | 12/2005 | Honda et al. | 514/25 |
| 7,176,237 | B2 | 2/2007 | Honda et al. | 514/519 |
| 7,265,096 | B2 | 9/2007 | Gallop et al. | 514/49 |
| 7,288,568 | B2 | 10/2007 | Gribble et al. | 514/519 |
| 7,435,755 | B2 | 10/2008 | Konopleva et al. | 514/510 |
| 2002/0042535 | A1 | 4/2002 | Gribble et al. | 558/429 |
| 2005/0276836 | A1 | 12/2005 | Wilson et al. | 424/434 |
| 2005/0288363 | A1 | 12/2005 | Gribble et al. | 558/303 |
| 2007/0155742 | A1 | 7/2007 | Honda et al. | 514/519 |
| 2008/0220057 | A1 | 9/2008 | Gribble et al. | 514/522 |
| 2009/0093447 | A1 | 4/2009 | Konopleva et al. | 514/510 |

FOREIGN PATENT DOCUMENTS

| | | |
|---|---|---|
| DE | 10 2005 041613 | 3/2007 |
| EP | 0 272 891 A2 | 6/1988 |
| EP | 0 329 348 B1 | 7/1995 |
| EP | 0 376 518 B1 | 11/1995 |
| EP | 0 576 230 B1 | 4/1996 |
| EP | 0 577 303 B1 | 10/1997 |
| EP | 0 712 860 B1 | 12/2001 |
| WO | WO 91/15498 | 10/1991 |
| WO | WO 98/00173 | 1/1998 |
| WO | WO 98/32762 | 7/1998 |
| WO | WO 99/33483 | 7/1999 |
| WO | WO 99/65478 | 12/1999 |
| WO | WO 00/73253 | 12/2000 |
| WO | WO 01/01135 | 1/2001 |
| WO | WO 02/03996 | 1/2002 |
| WO | WO 2005/042002 | 5/2002 |

(Continued)

OTHER PUBLICATIONS

Cancer and Metastasis Reviews (1998), 17(1), 91-106.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL;http://www.cnn.com/2003/HEALTH/conditions/09/24/alzheimers.drug.ap/index.html>.*
Science (1999), vol. 286, 531-537.*
Mandel et al., CNS Drugs, 2003: 17(10); 729-62.*
Favaloro et al., Journal of Medicinal Chemistry, vol. 45, No. 22, Oct. 24, 2002.*

(Continued)

*Primary Examiner*—Rebecca L Anderson
(74) *Attorney, Agent, or Firm*—Fulbright & Jaworski LLP

(57) ABSTRACT

Novel tricyclic-bis-enone derivatives (TBEs) as well as the process for the preparation of such TBEs are provided. Also provided are methods for prevention and/or treatment of cancer, Alzheimer's disease, Parkinson's disease, multiple sclerosis, amyotropic lateral sclerosis, rheumatoid arthritis, inflammatory bowel disease, and all other diseases whose pathogenesis is believed to involve excessive production of either nitric oxide (NO) or prostaglandins or the overexpression of iNOS or COX-2 genes or gene products. Further, methods for the synthesis of the TBE compounds of the invention utilize cheap commercially available reagents and are highly cost effective and amenable to scale-up. Additional high efficiency synthetic methods that utilize novel intermediates as well as the synthesis of these intermediates are also provided. Furthermore, the invention also provides methods for designing novel and water-soluble TBEs.

10 Claims, 5 Drawing Sheets

FOREIGN PATENT DOCUMENTS

| | | |
|---|---|---|
| WO | WO 2005/046732 | 5/2002 |
| WO | WO 02/47611 | 6/2002 |
| WO | WO 03/043631 | 5/2003 |
| WO | WO 03/059339 | 7/2003 |
| WO | WO 2006/029221 | 3/2006 |
| WO | WO 2007/005879 | 1/2007 |
| WO | WO 2007/069895 | 6/2007 |
| WO | WO 2008/111497 | 9/2008 |
| WO | WO 2008/136838 | 11/2008 |
| WO | WO 2009/023232 | 2/2009 |

OTHER PUBLICATIONS

Agarwal and Mehta, "Possible involvement of Bcl-2 pathway in resinoid X receptor alpha-induced apoptosis of HL-60 cells," *Biochem Biophys Res Common*, 230(2):251-253, 1997.

Al-alami et al., "Divergent effect of taxol on proliferation, apoptosis and nitric oxide production in MHH225 CD34 positive and U937 CD34 negative human leukemia cells," *Leukemia Res.*, 22:939-945, 1998.

Ambs et al., "p53 and vascular endothelial growth factor regulate tumor growth of NOS2-expressing human carcinoma cells," *Nat. Med.*, 4(12):1371-1376, 1998.

Amstutz et al., "Die position 5 im oxotremorin-gerust: eine zentrale stelle fur die steuerung der aktivitat am muscarinischen rezeptor," *Helv. Chim. Acta.*, 70:2232-2244, 1987.

Andreeff et al., "Expression of bcl-2-related genes in normal and AML progenitors: Changes induced by chemotherapy and cationic acid," *Leukemia*, 13:1881-1892, 1999.

Andreeff et al., "PPARgamma nuclear receptor as a novel molecular target in leukemias," *2002 Keystone Symposia*, Abstract No. 501, 2002.

Andreeff, "Acute myeloid leukemia," *In: Cancer Treatment*, Haskell (Ed.), W. B. Saunders, 911-922, 1995.

Baeuerle, "NF-κB: ten years after," *Cell*, 87:13-20, 1996.

Bagasra et al., "Activation of the inducible form of nitric oxide synthase in the brains of patients with multiple sclerosis," *Proc. Natl. Acad. Sci. USA*, 92:12041-12045, 1995.

Baldwin, "The NF-κB and IκB proteins: new discoveries and insights," *Annu. Rev. Immunol.*, 14:649-681, 1996.

Bargou et al., "Constitutive nuclear factor κB-ReIA activation is required for proliferation and survival of Hodgkin's disease tumor cells," *J. Clin. Invest.*, 100:2961-2969, 1997.

Barkett and Gilmore, "Control of apoptosis by Rel/NF-κB transcription factors," *Oncogene*, 18:6910-6924, 1999.

Barnes and Karin, "Nuclear factor-κB—a pivotal transcription factor in chronic inflammation diseases," *N. Engl. J. Med.*, 336:1066-1071, 1997.

Beran et al., "Topotecan and cytarabine is an active combination regimen in myelodysplastic syndromes and chronic myelomonocytic leukemia," *J. Clinical Oncology*, 17(9):2819-2830, 1999.

Bliard et al., "Glycosylation of acids under phase transfer conditions. Partial synthesis of saponins," *Tetrahedron Lett.*, 35:6107-6108, 1994.

Bogdan et al., "Contrasting mechanisms for suppression of macrophage cytokine release by transforming growth factor-β and interleukin-10," *J. Biol. Chem.*, 267:23301-23308, 1992.

Bogdon and Ding, "Taxol, a microtubule-stabilizing antineoplastic agent, induces expression of tumor necrosis factor α and interleukin-1 in macrophages," *J. Leukoc. Biol.*, 52(1):119-121, 1992.

Boolbol et al., "Cyclooxygenase-2 overexpression and tumor formation are blocked by sulindac in a murine model of familial adenomatous polyposis," *Cancer Res.*, 56(11):2556-2560, 1996.

Bore et al., "The anti-inflammatory triterpenoid methyl 2-cyano-3,12-dioxoolean 1,9(11)-dien-28-oate methanol solvate hydrate," *Acta Crystallorg C.*, 58(Pt 3):o199-o200, 2002.

Brookes et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore," *Cancer Res.*, 67:1793-1802, 2007.

Buzoni-Gatel et al., "Intraepithelial lymphocytes traffic to the intestine and enhance resistance to *Toxoplasma gondii* oral infection," *J. Immunol.*, 162:5846-5852, 1999.

Buzoni-Gatel et al., "Murine ileitis after intracellular parasite infection is controlled by TGF-beta-producing intraepithelial lymphocytes," *Gastroenterolog*, 120:914-924, 2001.

Cai et al., "A new protecting group for alkynes: orthogonally protected dialkynes," *Helv. Chim. Acta.*, 78:732-757, 1995.

Carter et al., "Expression of survivin, a member of the inhibitor of apoptosis (IAP) family of caspase inhibitors is expressed in AML and regulated by cytokines and ATRA," *Blood*, 94(Suppl 1):479a, Abstract # 2142, 1999.

Cassady and Suffness, In *Anticancer Agents Based on Natural Product Models*; Academic Press, NY, 254-269, 1980.

Castaigne et al., "All-trans retinoic acid as a differentiation therapy for acute promyelocytic leukemia," *Blood*, 76(9):1704-1709, 1990.

Chauhan et al., "The bortezomib/proteasome inhibitor PS-341 and triterpenoid CDDO-Im induce synergistic anti-multiple myeloma (MM) activity and overcome bortezomib resistance," *Blood*, 103:3158-3166, 2004.

Chintharlapalli et al., "2-Cyano-3,12-dioxoolean-1,9-dien-28-oic acid and related compounds inhibit growth of colon cancer cells through peroxisome proliferator-activated receptor gamma-dependent and -independent pathways," *Mol. Pharmacol.*, 68:119-128, 2005.

Chung and Wasicak, "Synthesis of chiral α-acetylenic cyclic amines from α-amino acids: applications to differentially constrained oxotremorine analogues as muscarinic agents," *Tetrahedron Lett.*, 31:3957-3960, 1990.

Clinton et al., "Steroidal[3,2-c]pyrazoles. II. Androstanes, 19-norandrostanes and their unsaturated analogs," *J. Am. Chem. Soc.*, 83:1478-1491, 1961.

Corey and Ruden, "Stereoselective methods for the synthesis of terminal cis AND trans enyne untis," *Tetrahedron Lett.*, 1495-1499, 1973.

Coyle and Puttfarcken, "Oxidative stress, glutamate, and neurodegenerative disorders," *Science*, 262:689-695, 1993.

Dean et al., "Halogenolysis of methyl glycyrrhetate with lithium iodidedimethylformamide," *J. Chem. Soc.*, 6655-6659, 1965.

Dezulbe et al., "Interim results of a phase I trial with a novel orally administered synthetic triterpenoid RTA 402 (CDDO-Me) in patients with solid tumors and lymphoid malignancies," *J. Clin. Oncol.*, 2007 ASCO Annual Meeting Proceedings, 25(18S):14101, 2007.

Ding et al., "Macrophage deactivating factor and transforming growth factors-$\beta_1$ $\beta_2$ and $\beta_3$, inhibit induction of macrophage nitrogen oxide synthesis by IFNγ[1]," *J. Immunol.*, 145:940-944, 1990.

Drach et al., "Induction of differentiation in myeloid leukemia cell lines and acute promyelocytic leukemia cells by liposomal all-trans-retinoic acid," *Cancer Research*, 53:2100-2104, 1993.

Drefahl and Huneck, "Nor-olea-12-enol-17-amin und Olea-12-enol-28-amin," *Chem. Ber.*, 91:278-281, 1958.

DuBois et al., "$G_1$ delay in cells overexpressing prostaglandin endoperoxide synthase-2[1]," *Cancer Res.*, 56(4):733-737, 1996.

DuBois et al., "Increased cyclooxygenase-2 levels in carcinogen-induced rat colonic tumors," *Gastroenterology*, 110:1259-1262, 1996.

Dutcher et al., "Pentacyclic triterpene synthesis. 5. Synthesis of optically pure ring AB precursors," *J. Org. Chem.*, 41:2663-2669, 1976.

Elliot et al., "The triterpenoid CDDO inhibits expression of matrix metalloproteinase-1, matrix metalloproteinase-13 and Bcl-3 in primary human chondrocytes," *Arthritis Res. Ther.*, 5:R285-R291, 2003.

Elsawa et al., "Preferential Inhibition of Malignant Cell Growth by CDDO in Waldenstrom Macroglobulinemia," *Blood*, 108(11):2528, 2006.

Elstner et al., "Ligands for peroxisome proliferator-activated receptorgamma and retinoic acid receptor inhibit growth and induce apoptosis of human breast cancer cells in vitro and in BNX mice," *Proc. Natl. Acad. Sci. USA*, 95:8806-8811, 1998.

Engel et al., "Quantitation of minimal residual disease in acute myelogenous leukemia and myelodysplastic syndromes in complete remission by molecular cytogenetics of progenitor cells," *Leukemia*, 13:568-577, 1999.

Estey et al., "Molecular remissions induced by liposomal-encapsulated all-trans retinoic acid in newly diagnosed acute promyelocytic leukemia," *Blood*, 94:2230-2235, 1999.

Estey et al., "Randomized phase II study of fludarabine + cytosine arabinoside + idarubicin + all-trans retinoic acid + granulocyte-colony stimulating factor in poor prognosis newly diagnosed acute myeloid leukemia and myelodysplastic syndrom," *Blood*, 93(8):2478-2484, 1998.

Favaloro et al., "Design and synthesis of tricyclic compounds with enone functionalities in rings A and C: a novel class of highly active inhibitors of nitric oxide production in mouse macrophages," *J. Med. Chem.*, 45:4801-4805, 2002.

Finkbeiner and Stiles, "Chelation as a driving force in organic reactions. IV. Synthesis of α-nitro acids by control of the carboxylastion-decarboxylation equilibrum," *J. Am. Chem. Soc.*, 85:616-622, 1963.

Genain and Hauser, "Creation of a model for multiple sclerosis in Callithrix jacchus marmosets," *J. Mol. Med.*, 75:187-197, 1997.

Ghosh et al., "NF-κB and Rel proteins: evolutionarily conserved mediators of immune response," *Annu Rev Immunol.*, 16:225-260, 1998.

Grieco and Speake, "Synthetic Studies on Quassinoids: Total Synthesis and Biological Evaluation of (+)-Des-D-chaparrinone," *J. Org. Chem.*, 63:5929-5936, 1998.

Grieco et al., "Synthetic studies on quassinoids: total synthesis and biological evaluation of (+)-des-D-chaparrinone," *J. Org. Chem.*, 63:5929-5936, 1998.

Gura et al., "Systems for identifying new drugs are often faulty," *Science*, 278:1041-1042, 1997.

Guttridge et al., "NF-kappaB controls cell growth and differentiation through transcriptional regulation of cyclin D1," *Mol. Cell. Biol.*, 19:5785-5799, 1999.

Hail et al., "Evidence supporting a role for calcium in apoptosis induction by the synthetic triterpenoid 2-cyano-3,12-dioxooleana-1,9-dien-28-oic acid (CDDO)," *J. Biol. Chem.*, 279:11179-11187, 2004.

Hinz et al., "NF-kappaB function in growth control: regulation of cyclin D1 expression and G0/G1-to-S-phase transition," *Mol. Cell Biol.*, 19:2690-2698, 1999.

Hirota et al., "Stereoselective total synthesis of (±)-eperuane-8β,15-diol[1]," *Bull. Chem. Soc. Jpn.*, 61:4023-4028, 1988.

Hirota et al., "Suppression of tumor promoter-induced inflammation of mouse ear by ursolic acid and 4,4-dimethycholestane derivatives, "*Agric. Biol. Chem.*, 54:1073-1075, 1990.

Hirota et al., "Total synthesis of (±)-amarolide, a quassinoid bitter principle," *J. Org. Chem.*, 56:1119-1127, 1991.

Honda et al., "A novel dicyanotriterpenoid, 2-cyano-3,12-dioxooleanan-1,9(11)-dien-28-onitrile, active at picomolar concentrations for inhibition of nitric oxide production," *Bioorganic & Medicinal Chemistry Letters*, 12:1027-1030, 2002.

Honda et al., "Design and synthesis of 2-cyano-3,12-dioxoolean-1,9-dien-28-oic acid, a novel and highly active inhibitor of nitric oxide production in mouse macrophages," *Bioorg Med Chem Lett.*, 8(19):2711-2714, 1998.

Honda et al., "Efficient synthesis of (−)- and (+)-tricyclic compounds with enome functionalities in rings and C. A novel class of orally active anti-inflammatory and cancer chemopreventive agents," Org Biomol Chem, 1:4384-4391, 2003.

Honda et al., "New enone derivatives of oleanolic acid and ursolic acid as inhibitors of nitric oxide production in mouse macrophages," *Bioorg. Med. Chem. Lett.*, 7:1623-1628, 1997.

Honda et al., "Novel synthetic oleanane and ursane triterpenoids with various enone functionalities in ring A as inhibitors of nitric oxide production in mouse macrophages," *J. Med. Chem.*, 43:1866-1877, 2000.

Honda et al., "Novel synthetic oleanane triterpenoids: a series of highly active inhibitors of nitric oxide production in mouse macrophages," *Bioorg. Med. Chem. Lett.*, 9(24):3429-3434, 1999.

Honda et al., "Synthesis of (±)-3,3-ethylenedioxy-14α-hydroxy-5-picrasene-11,16-dione, a 14αH-picrasane derivative," *Chem. Lett.*, 299-302, 1981.

Honda et al., "Synthetic oleanane and ursane triterpenoids with modified rings A and C: A series of highly active inhibitors of nitric oxide production in mouse macrophages," *J. Med. Chem.*, 43:4233-4246, 2000.

Huang et al., "Inhibition of skin tumorigenesis by Rosemary and its constituents carnosol and ursolic acid," *Cancer Res.*, 54:701-708, 1994.

Huang et al., "Structure of a WW domain containing fragment of dystrophin in complex with β-dystroglycan," *Nat. Struct Biol.*, 7:634-638, 2000.

Hyer et al., "Synthetic triterpenoids cooperate with tumor necrosis factor-related apoptosis-inducing ligand to induce apoptosis of breast cancer cells," *Cancer Res.*, 65:4799-4808, 2005.

Ikeda et al., "Induction of redox imbalance and apoptosis in multiple myeloma cells by the novel triterpenoid 2-cyano-3,12-dioxoolean-1,9-dien-28-oic acid," *Mol. Cancer Ther.*, 3:39-45, 2004.

Ikeda et al., "The novel triterpenoid CDDO and its derivatives induce apoptosis by disruption of intracellular redox balance," *Cancer Res.*, 63:5551-5558, 2003.

Ito et al., "Involvement of caspase-8 in the induction of osteosarcoma cell apoptosis by the novel triterpenoid CDDO," *47th Annual Meeting, Orthopaedic Research Society*, Feb. 25- 28, 2001, San Francisco, California, p. 0863, Poster Session, 2001.

Ito et al., "The novel triterpenoid 2-cyano-3,12-dioxoolean-1,9-dien-28-oic acid induces apoptosis of human myeloid leukemia cells by a caspase-8-dependent mechanism," *Cell Growth Differ.*, 11:261-267, 2000.

Ito et al., "The novel triterpenoid CDDO induces apoptosis and differentiation of human osteosarcoma cells by a caspase-8 dependent mechanism," *Mol. Pharmacol*, 59:1094-1099, 2001.

Johansen et al., "Pharmacology and preclinical pharmacokinetics of the triterpenoid CDDO methyl ester," *Proc. Amer. Assoc. Cancer Res.*, 44:1728, 2003.

Johnson et al., "A plan for distinguishing between some five- and six-membered ring ketones," *J. Am Chem. Soc.*, 67:1745-1754, 1945.

Johnson et al., "Relationships between drug activity in NCI preclinical in vitro and in vivo models and early clinical trials," *Br. J. Cancer*, 84:1424-1431, 2001.

Joyce et al., "Integration of Rac-dependent regulation of cyclin D1 transcription through a nuclear factor-kappaB-dependent pathway," *J. Biol. Chem.*, 274:25245-25249, 1999.

Kahne and Collum, "Kinetic cyanations of ketone enolates," *Tetrahedron Lett.*, 22:5011-5014, 1981.

Kaltschmidt et al., "Transcription factor NF-kappaB is activated in primary neurons by amyloid beta peptides and in neurons surrounding early plaques from patients with Alzheimer disease," *Proc. Natl. Acad. Sci. USA*, 94:2642-2647, 1997.

Kawamori et al., "Chemopreventive activity of celecoxib, as specific cyclooxygenase-2 inhibitor, against colon carcinogenesis," *Cancer Res.*, 58(3):409-412, 1998.

Kerwin et al., "Quassinoid synthesis. 2. Preparation of a tetracyclic intermediate having the Bruceantin tetrahydrofuran ring," *J. Org. Chem.*, 52:1686-1695, 1987.

Khan et al., "A dichotomous role for nitric oxide during acute Toxoplasma gondii infection in mice," *Proc. Natl. Acad. Sci. USA*, 94:13955-13960, 1997.

Kim et al., "Capasase-3 activation is involved in apoptosis induced by a synthetic triterpenoid in Non-small cell lung cancer (NSCLC) cells," *Proc. Amer. Assoc. Cancer Res.*, 41:770, Abstract #4894, 2000.

Kim et al., "Identification of a novel synthetic triterpenoid, methyl-2-cyano-3,12-dioxooleana-1,9-dien-28-oate, that potently induces caspace-mediated apoptosis in human lung cancer cells," Molecular Cancer Therapeutics, 1:177-184, 2002.

Kircher, "Triterpenes, in organ pipe cactus," *Phytochemistry*, 19:2707-2712, 1980; Database CAPLUS on STN AN:1981:550946.

Konopleva and Andreeff, "Regulatory pathways in programmed cell death," *Cancer Mol Biol.*, 6:1229-1260, 1999.

Konopleva et al., "Activation of nuclear transcription factor PPARgamma by the novel triterpenoid CDDO as targeted therapy in breast cancer," *2002 Keystone Symposium*, Abstract No. 539, 2002.

Konopleva et al., "Apoptosis: molecules and mechanisms," *Adv Exp Med Biol*, 457:217-236, 1998.

Konopleva et al., "Mechanisms and Activity of PPARgamma-Active Triterpenoids CDDO and CDDO-Me in Leukemias," *Blood*, 106:2460, 2005.

Konopleva et al., "Novel synthetic triterpenoid CDDO-Me: potent antiproliferative, proapoptotic and differentiating agent in AML," *Blood*, 96(11), Part 1: 121A, abstract # 522, 2000.

Konopleva et al., "Novel synthetic triterpenoid, CDDO, and its methyl ester: Potent antiproliferative, proapoptotic and differentiating agents in AML," *Blood*, 94(Suppl 1):479a, Abstract #2140, 1999.

Konopleva et al., "Novel triterpenoid CDD0-Me is a potent inducer of apoptosis and differentiation in acute myelogenous leukemia," *Blood*, 99(1):326-335, 2002.

Konopleva et al., "Peroxisome proliferator-activated receptor gamma and retinoid X receptor ligands are potent inducers of differentiation and apoptosis in leukemias," *Mol. Cancer Ther.*, 3:1249-1262, 2004.

Konopleva et al., "PPARγ nuclear receptor as a novel therapeutic target in AML," *Blood*, 96(11):460a, Abstract #1982, 2000.

Konopleva et al., "PPARgamma Ligand CDDO Induces Apoptosis in Leukemias Via Multiple Apoptosis Pathways," *Abstracts of the 44th Annual Meeting of the American Society of Hematology*, Abstract No. 2209, 2002.

Konopleva et al., "PPARgamma Ligands Are Potent Inducers of Apoptosis in Leukemias and Lymphomas," *American Society of Hematology 43rd Annual Meeting and Exposition*, Abstract No. 501, 2001.

Konopleva et al., "PPARgamma Nuclear Receptor as a Novel Molecular Target in Leukemia Therapy," *Proc. Amer. Assoc. Cancer Res.*, 43:4730, 2002.

Konopleva et al., "PPARgamma Nuclear Receptor as a Novel Therapeutic Target in AML," *Proc. Amer. Assoc. Cancer Res.*, 42:4458, 2001.

Konopleva et al., "Suppression of ERK Activation is Required for Triterpenoid Methyl-CDDO-Induced Apoptosis in AML," *Blood*, 102(11):1404, 2003.

Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317-328, 2006.

Konopleva et al., "Synthetic triterpenoid CDDO as a novel therapy for resistant breast cancer," *Proc. Amer. Assoc. Cancer Res.*, 44:2726, 2003.

Konopleva et al., "The novel triterpenoid CDDO-Me suppresses MAPK pathways and promotes p38 activation in acute myeloid leukemia cells," *Leukemia*, 19:1350-1354, 2005.

Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.

Konopleva et al., "Triterpenoid Methyl-CDDO Is a Potent Inducer of Apoptosis in CD34+ AML Progenitor Cells Via Activation of SAPK Pathways and Inhibition of MAPK Cascades," *Blood*, 104:2533, 2004.

Kornblau et al., "Apoptosis regulating proteins as targets of therapy for hematological malignancies," *Exp. Opin. Inv. Drugs*, 8:2027-2057, 1999.

Kornblau et al., "Phase I study of mitoxantrone plus etoposide with multidrug blockage by SDZ PSC-833 in relapsed or refractory acute myelogenous leukemia," *J. Clin. Oncol.*, 15(5):1796-1802, 1997.

Kowalski and Reddy, "Ester homologation revisited: a reliable, higher yielding and better understood procedure," *J. Org. Chem.*, 57:7194-7208, 1992.

Kress et al., "Triterpenoids Display Single Agent Activity in a Mouse Model of CLL/SBL," *Blood*, 108(11):2530, 2006.

Kress et al., "Triterpenoids Display Single Agent Anti-tumor Activity in a Transgenic Mouse Model of Chronic Lymphocytic Leukemia and Small B Cell Lymphoma," *PLoS ONE*, 6(e559):1-11, 2007.

Kurbacher et al., "Ascorbic acid (vitamin C) improves the antineoplastic activity of doxorubicin, cisplatin, and paclitaxel in human breast carcinoma cells in vitro," *Cancer Lett.*, 103:183-189, 1996.

Kurinna et al., "The novel triterpenoid CDDO-Me promotes apoptosis in Gleevec-resistant chronic myeloid leukemia cells by caspase-independent mechanisms," *Proc. Amer. Assoc. Cancer Res.*, 46:2240, 2005.

Lapillonne et al., "Activation of peroxisome proliferator-activated receptor gamma by a novel synthetic triterpenoid 2-cyano-3,12-dioxooleana-1,9-dien-28-oic acid induces growth arrest and apoptosis in breast cancer cells," *Cancer Res.*, 63:5926-5939, 2003.

Lee et al., "Functional and quantitative analysis of splenic T cell immune responses following oral toxoplasma gondii infection in mice," *Experimental Parasitology*, 91:212-221, 1999.

Lemieux, "Acylglycosyl Halides. [55] tetra-O-acetyl-α-D-glucopyranosyl bromide," *Methods Carbohydr. Chem.*, 2:221-222, 1963.

Lieu et al., "Dual cytotoxic mechanisms of submicromolar taxol on human leukemia HL-60 cells," *Biochem. Pharmacology*, 53:1587-1596, 1997.

Ling et al., "The novel triterpenoid C-28 methyl ester of 2-cyano-3,12-dioxoolen-1, 9-dien-28-oic acid inhibits metastatic murine breast tumor growth through inactivation of STAT3 signaling," *Cancer Res.*, 67:4210-4218, 2007.

Ling et al., "The novel triterpenoid CDDO-Me inhibits metastatic murine breast tumor through inhibition of Stat3 signaling," 2007 AACR Annual Meeting, Abstract No. 301, 2007.

Liotta et al., "A simple method for the efficient sysnthesis of unsaturated β-dicarbonyl compunds," *J. Org. Chem.*, 46:2920-2923, 1981.

MacMicking et al., "Altered responses to bacterial infection and endotoxic shock in mice lacking inducible nitric oxide synthase," *Cell*, 81:641-650, 1995.

Marnett, "Aspirin and the potential role of prostaglandins in colon cancer," *Cancer Res.*, 52(20):5575-5589, 1992.

McGeer and McGeer, "The inflammatory response system of brain: implications for therapy of Alzheimer and other neurodegenerative diseases," *Brain Res. Brain Res. Rev.*, 21:195-218, 1995.

Mehta et al., "Activation of retinoid receptors RAR alpha and RXR alpha induces differentiation and apoptosis, respectively, in HL-60 cells," *Cell, Growth Differ*, 7(2): 179-186, 1996.

Melichar et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-gamma expression," *Gynecologic Oncology*, 93:149-154, 2004.

Mella et al.,"1, 2-dideoxy-3, 4:5, 7-bis-o—(1-methylethylidene)—D-gluco- and—D-galacto-hept-1-ynitols : synthesis and conformational studies," *Tetrahedron*, 44:1673-1678, 1988.

Merril and Benveniste, "Cytokines in inflammatory brain lesions: helpful and harmful," *Trends Neurosci.*, 19:331-338, 1996.

Minns et al., "A novel triterpenoid induces transforming growth factor beta production by intraepithelial lymphocytes to prevent ileitis," *Gastroenterology*, 127:119-126, 2004.

Mix et al., "A synthetic triterpenoid selectively inhibits the induction of matrix metalloproteinases 1 and 13 by inflammmatory cytokines," *Arthritis Rheum.*, 44:1096-1104, 2001.

Mix et al., "Peroxisome proliferator-activated receptor-gamma-independent repression of collagenase gene expression by 2-cyano-3,12-dioxooleana-1,9-dien-28-oic acid and prostaglandin 15-deoxy-delta(12,14) J2: a role for Smad signaling," *Mol. Pharmacol.*, 65:309-318, 2004.

Moncada et al., "Nitric oxide: physiology, pathophysiology, and pharmacology," *Pharmacol. Rev.*, 43:109-142, 1991.

Murphy et al., "Immunomodulatory Effects of the Triterpenoid CDDO after Allogeneic Bone Marrow Transplantation in Mice: Reduction of Acute Graft-Versus-Host Disease Lethality," *Blood*, 106:1316, 2005.

Muzart, "Synthesis of unsaturated carbonyl compounds via a chromium-mediated allylic oxidation by 70% tert.butylhydroperoxide," *Tetrahedron Lett.*, 28:4665-4668, 1987.

Nathan and Xie, "Nitric oxide synthases: roles, tolls, and controls," *Cell*, 78:915-918, 1994.

Nicholson et al., "Lethality of endotoxin in mice genetically deficient in the respiratory burst oxidase, inducible nitric oxide synthase, or both," *Shock*, 11:253-258, 1999.

Nishino et al., "Inhibition of the tumor-promoting action of 12-O tetradecanoylphorbol-13-acetate by some oleanane-type triterpenoid compounds," *Cancer Res.*, 48:5210-5215, 1988.

Ohshima and Bartsch, "Chronic infections and inflammatory process as cancer risk factors: possible role of nitric oxide in carcinogenesis," *Mutat. Res.*, 305:253-264, 1994.

Ono et al., "A convenient procedure for esterification of carboxylic acids," *Bull. Chem. Soc. Jpn.*, 51:2401-2404, 1978.

Oshima et al., "Suppression of intestinal polyposis in Apc$^{\Delta 716}$ knock-out mice by inhibition of cyclooxygenase 2 (COX-2)," *Cell*, 87:803-809, 1996.

Pahl, "Activators and target genes of Rel/NF-κB transcription factors," *Oncogene*, 18:6853-6866, 1999.

Pedersen et al., "The triterpenoid CDDO induces apoptosis in refractory CLL B cells," *Blood*, 100:2965-2972, 2002.

Picard et al., "The triterpene resinols and related acids, part VI," *J. Chem. Soc.*, 1045-108, 1939.

Place et al., "The novel synthetic triterpenoid, CDDO-imidazolide, inhibits inflammatory response and tumor growth in vivo," *Clin. Cancer Res.*, 9:2798-2806, 2003.

Prescott and White, "Self-promotion? Intimate connections between APC and prostaglandin H synthase-2," *Cell*, 87(5):783-786, 1996.

Rayet and Gelinas, "Aberrant rel/nfkb genes and activity in human cancer," *Oncogene*, 18:6938-6947, 1999.

Reddy et al., "Evaluation of cyclooxygenase-2 inhibitor for potential chemopreventive properties in colon carcinogenesis," *Cancer Res.*, 56(20):4566-4569, 1996.

Rossi et al., "Anti-inflammatory cyclopentenone prostaglandins are direct inhibitors of IkappaB kinase," *Nature*, 403:103-108, 2000.

Ruvolo et al., "The novel triterpenoid methyl-CDDO inhibits Bc12 phosphorylation and potently kolls U937 cells," *Blood*, 94(10), Suppl. 1, Part 1: 280A, abstract #1251, 1999.

Salvemini et al., "Endogenous nitric oxide enhances prostaglandin production in a model of renal inflammation," *J. Clin. Invest.*, 93(5):1940-1947, 1994.

Salvemini et al., "Nitric oxide activates cyclooxygenase enzymes," *Proc. Natl. Acad. Sci. USA*, 90(15):7240-7244, 1993.

Samudio et al., "2,cyano-3,12 dioxoolean-1,9 diene-28-imidazolide induces apoptosis in pancreatic cancer via redox-dependent cytoplasmic stress," *Proc. Amer. Assoc. Cancer Res.*, 46:5899, 2005.

Samudio et al., "2-Cyano-3,12-dioxooleana-1,9-dien-28-imidazolide (CDDO-Im) directly targets mitochondrial glutathione to induce apoptosis in pancreatic cancer," *J. Biol. Chem.*, 280:36273-36282, 2005.

Samudio et al., "A novel mechanism of action of methyl-2-cyano-3,12 dioxoolean-1,9 diene-28-oate: direct permeabilization of the inner mitochondrial membrane to inhibit electron transport and induce apoptosis," *Mol. Pharmacol.*, 69:1182-1193, 2006.

Samudio et al., "A novel mechanism of action of methyl-2-cyano-3,12 dioxoolean-1,9 diene-28-oate (CDDO-Me): Direct permeabilization of the inner mitochondrial membrane to inhibit electron transport and induce apoptosis," *Proc. Am. Assoc. Cancer Res.*, 47: 4693, 2006.

Samudio et al., "A Novel Mechanism of Action of Methyl-2-cyano-3,12 dioxoolean-1,9 diene-28-oate (CDDO-Me): Direct Permeabilization of the Inner Mitochondrial Membrane to Inhibit Electron Transport and Induce Apoptosis," *Blood*, 106:4462, 2005.

Samudio et al., "The novel triterpenoid CDDOme potently synergizes with inhibition of bcl-2 function to induce apoptosis in AML via disruption of intracellular redox homeostasis," *Proc. Amer. Assoc. Cancer Res.*, 46:4955, 2005.

Scholz et al., "Sensitive and specific methods for the determination of CDDO methyl ester in mouse, rat, dog, monkey, and human plasma by LC-tandem mass spectrometry," *Proc. Amer. Assoc. Cancer Res.*, 4:6321, 2003.

Seibert and Masferrer, "Role of inducible cyclooxygenase (COX-2) in inflammation," *Receptor*, 4(1):17-23, 1994.

Sharpless et al., "Electrophilic and nucleophilic organoselenium reagents. New routes to alpha, beta-unsaturated carbonyl compounds," *J. Am. Chem. Soc.*, 95:6137, 1973.

Sheng et al., "A selective cyclooxygenase 2 inhibitor suppresses the growth of H-ras-transformed rat intestinal epithelial cells," *Gastroenterology*, 113(6):1883-18891, 1997.

Sheng et al., "Inhibition of human colon cancer cell growth by selective inhibition of cyclooxygenase-2," *J. Clin. Invest.*, 99(9):2254-2259, 1997.

Shishodia et al., "A synthetic triterpenoid, CDDO-Me, inhibits IkappaBalpha kinase and enhances apoptosis induced by TNF and chemotherapeutic agents through down-regulation of expression of nuclear factor kappaB-regulated gene products in human leukemic cells," *Clin. Cancer Res.*, 12:1828-1838, 2006.

Simonian and Coyle, "Oxidative stress in neurodegenerative diseases," *Annu. Rev. Pharmacol Toxicol.*, 36:83-106, 1996.

Simonsen et al., "Tetracyclic hydroxy acids," In *the Terpenes*, Cambridge University, Cambridge, 5:221-285, 1957.

Singh et al., "Anti-inflammatory activity of oleanolic acid in rats and mice," *J. Pharm.Pharmacol.*, 44:456-458, 1992.

Snitman et al., "Synthetic approaches to taxodione synthesis of methyl 12-oxopodocarpa-5,9(11)-diene-8β-carboxylate," *Synth. Comm.*, 8:187-194, 1978.

Sonogashira et al., "A convenient synthesis of acetylenes: catalytic substitutions of acetylenic hydrogen with bromoakenes, iodoarenes, and bromopyridines," *Tetrahedron Lett.*, 4467-4470, 1975.

Sporn and Roberts, "Peptide growth factors and inflammation, tissue repair, and cancer," *J. Clin. Invest.*, 78:329-332, 1986.

Sporn et al., "Prospects for prevention and treatment of cancer with selective PPARγ modulators (SPARMs)," *Trends in Molecular Medicine*, 7(9):395-400, 2001.

Stadheim et al., "The novel triterpenoid 2-cyano-3,12-dioxooleana-1,9-dien-28-oic acid (CDDO) potently enhances apoptosis induced by tumor necrosis factor in human leukemia cells," *J. Biol. Chem.*, 277:16448-16455, 2002.

Sterzycki, "Pyrodinium tosylate, a mild catalyst for formation and cleavage of dioxolane-type acetals," *Synthesis*, 724-725, 1979.

Stewart et al., "Risk of Alzheimer's disease and duration of NSAID use" *Neurology*, 48:626-632, 1997.

Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59(2):336-341, 1999.

Suh et al., "A novel synthetic oleanane triterpenoid, 2-cyano-3,12-dioxoolean-1,9-dien-28-oic acid (CDDO), induces cell differentiation in human myeloid leukemias," *Proceedings of the American Association for Cancer Research Annual Meeting*, 40:300, abstract # 1988, 1999.

Suh et al., "Novel triterpenoids suppress inducible ntiric oxide synthase (iNOS) and inducible cyclooxygenase (COX-2)," *Proceedings of the American Association for Cancer Research Annual Meeting*, 39(Abstract 1821):266, 1998.

Suh et al., "Synthetic triterpenoids activate a pathway for apoptosis in AML cells involving downregulation of FLIP and sensitization to TRAIL," *Leukemia*, 17:2122-2129, 2003.

Suh et al., "Synthetic triterpenoids enhance transforming growth factor β/Smad signaling," *Cancer Res.*, 63:1371-1376, 2003.

Suh et al., "Triterpenoids CDDO and CDDO-Me Down-Regulate FLIP Expression and Sensitize AML Cells to Trail-Induced Apoptosis," *American Society of Hematology 43$^{rd}$ Annual Meeting and Exposition*, Abstract No. 498, 2001.

Sun et al., "The synthetic triterpenoid, CDDO, suppresses alloreactive T cell responses and reduces murine early acute graft-versus-host disease mortality," *Biology of Blood and Marrow Transplantation*, 13:521-529, 2007.

Tabe et al., "Chrmoatin-Mediated Transcriptional Activation with Novel Peroxisome Proliferator—Activated Receptor gamma(P-PARgamma) Ligand 2-cyano-1,9-dien-28-oic Acid (CDDO) in Acute Promyelocytic Leukemia Cells," *Abstracts of the 44$^{th}$ Annual Meeting of the American Society of Hematology*, Abstract No. 2191, 2002.

Takabe et al., "Synthesis of lycosyl esters of oleanolic," *Carbohydrate Research*, 76:101-108, 1979, Database CAPLUS on STN AN:1980:42278.

Takahashi et al., "Increased expression of inducible and endothelial constitutive nitric oxide synthases in rat colon tumors induced by azoxymethane," *Cancer Res.*, 57:1233-1237, 1997.

Tamir and Tannebaum, "The role of nitric oxide (NO) in the carcinogenic process," *Biochim. Biophys. Acta*, 1288:F31-F36, 1996.

Tamm et al., "Expression and prognostic significance of IAP-family genes in human cancers and leukemias," *Blood*, 94(Suppl. 1):69a, Abstract # 298, 1999.

Tsao et al., "DRIP205 co-activator overexpression enhances PPARgamma-mediated differentiation of leukemia cells by CDDO," *Proc. Amer. Assoc. Cancer Res.*, 46:1855, 2005.

Tsao et al., "Targeted Induction of Apoptosis in Leukemias by PPARgammma Ligation," *American Society of Hematology 43rd Annual Meeting and Exposition*, Abstract No. 2381, 2001.

Tsujii and DuBois, "Alterations in cellular adhesion and apoptosis in epithelial cells overexpressing prostaglandin endoperoxide synthase 2," *Cell*, 83(3):493-501, 1995.

Tsujii et al., "Cyclooxygenases regulates angiogenesis induced by colon cancer cells," *Cell*, 93:705-716, 1998.

Vazquez et al., "Human immunodeficiency virus type 1-induced macrophage gene expression includes the p21 gene, a target for viral regulation," *J. Virol.*, 79:4479-4491, 2005.

Walczak et al., "Tumoricidal activity of tumor necrosis factor-related apoptosis-inducing ligand in vivo", *Nature Medicine*, 5(2):157-163, 1999.

Wang et al., "A novel synthetic triterpenoid, 2-cyano-3,12-dioxoolean-1,9-dien-28-oic acid (CDDO) induces adipocyte differentiation in 3T3-L1 cells," *Proceedings of the American Association for Cancer Research Annual Meeting*, 40:300, abstract # 1989, 1999.

Wang et al., "A synthetic Triterpenoid, 2-cyano-3,12-dioxooleana-1,9-dien-28-oic acid (CDDO), is a ligand for the peroxisome proliferator-activated receptor γ," *Mol. Endocrin.*, 14(10):1550-1556, 2000.

Wang et al., "Synthetic triterpenoid CDDO and its derivatives increase ceramides and are cytotoxic to pediatric acute lymphoblastic leukemia cell lines," *Proc. Am. Assoc. Cancer Res.*, 47: 4643, 2006.

Warrell et al., "Differentiation therapy of acute promyelocytic leukemia with tretinoin (all-trans-retinoic acid)," *N. Engl. J. Med.*, 324(20):1385-1393, 1991.

Williams et al., "Immunology of multiple sclerosis," *Clin. Neurosci.*, 2(3-4):229-245, 1994.

Woodley, "Liposomes For Oral Administration of Drugs," *Crit. Rev. Therapeutic Drug Carrier System*, 2(1):1-18, 1985.

Xie et al., "Differential expression patterns in human myeloblastic leukemia HL-60 and multidrug resistant HL-60/Dox cells analyzed by human cDNA expression array," *Blood*, 92 (Suppl 1):387a, Abstract #1600. 1998.

Yates et al., "Pharmacodynamic characterization of chemopreventive triterpenoids as exceptionally potent inducers of Nrf2-regulated genes," *Mol. Cancer Ther.*, 6:154-162, 2007.

Yates et al., "Potent protection against aflatoxin-induced tumorigenesis through induction of Nrf2-regulated pathways by the triterpenoid 1-[2-cyano-3-,12-dioxooleana-1,9(11)-dien-28-oyl]imidazole," *Cancer Res.*, 66:2488-2494, 2006.

Zapata et al., "CDDO and CDDO-Im Reduce Tumor Burden in a Transgenic Mouse Model of CLL," *Blood*, 104:3477, 2004.

Zapata et al., "Triterpenoids show activity against leukemic cells in a transgenic mouse model of CLL," *Proc. Amer. Assoc. Cancer Res.*, 46:5179, 2005.

Zhang et al., "Synthetic triterpenoid CDDO as effective therapy for HER2-expressing resistant breast cancer," *Proc. Amer. Assoc. Cancer Res.*, Abstract No. 3799, 2004.

Zhang et al., "The novel synthetic oleanane triterpenoid CDDO (2-cyano-3, 12-dioxoolean-1, 9-dien-28-oic acid) induces apoptosis in Mycosis fungoides/Sézary syndrome cells," *J. Invest. Dermatol.*, 123:380-387, 2004.

Zou et al., "c-Jun NH2-terminal kinase-mediated up-regulation of death receptor 5 contributes to induction of apoptosis by the novel synthetic triterpenoid methyl-2-cyano-3,12-dioxooleana-1, 9-dien-28-oate in human lung cancer cells," *Cancer Res.*, 64:7570-7578, 2004.

Cho et al., "The transcription factor NRF2 protects against pulmonary fibrosis," *FASEB Journal*, 18:1-29, 2004.

Cianchi et al., "Cyclooxygenase-2 activation mediates the proangiogenic effect of nitric oxide in colorectal cancer," *Clinical Cancer Research*, 10:2694-2704, 2004.

Dinkova-Kostova et al., "Extremely potent triterpenoid inducers of the phase 2 response: correlations of protection against oxidant and inflammatory stress," *PNAS*, 102:4584-4589, 2005.

Ekmekcioglu et al., "Tumor iNOS predicts poor survival for stage III melanoma patients," *Int. J. Cancer*, 119:861-866, 2006.

Ellies et al., "Mammary tumor latency is increased in mice lacking the inducible nitric oxide synthase," *Int J. Cancer*, 106:1-7, 2003.

Honda et al., "Novel tricyclic compounds having acetylene groups at C-8a and cyano enones in rings A and C: highly potent anti-inflammatory and cytoprotective agents," *J. Med. Chem.*, 50:1731-1734, 2007.

Li and Nel, "Role of the Nrf2-mediated signaling pathway as a negative regulator of inflammation: implications for the impact of particulate pollutants on asthma," *Antioxidants & Redox Signaling*, 8:88-98, 2006.

Liby et al., "A novel acetylenic tricyclic bis-(cyano enone) potently induces phase 2 cytoprotective pathways and blocks liver carcinogenesis induced by aflatoxin," *Cancer Res.*, 68:6727-6733, 2008.

Liby et al., "The rexinoid LG100268 and the synthetic triterpenoid CDDO-methyl amide are more potent than erlotinib for prevention of mouse lung carcinogenesis," Mol. Cancer Ther., 7:1251-1257, 2008.

Liby et al., "The synthetic triterpenoids, CDDO and CDDO-imidazolide, are potent inducers of heme oxygenase-1 and Nrf2/ARE signaling," *Cancer Res.*, 65:4789-4798, 2005.

Liby et al., "Triterpenoids and rexinoids as multifunctional agents for the prevention and treatment of cancer," *Nature Reviews Cancer*, 7:357-369, 2007.

Mantovani et al., "Inflammation by remote control," *Nature*, 435:752-753, 2005.

Marrogi et al., "Nitric oxide synthase, cyclooxygenase 2, and vascular endothelial growth factor in the angiogenesis of non-small cell lung carcinoma," *Clinical Cancer Research*, 6:4739-4744, 2000.

Nathan et al., "Protection from Alzheimer's-like disease in the mouse by genetic ablation of inducible nitric oxide synthase," *The Journal of Experimental Medicine*, 202:1163-1169, 2005.

Nathan, "Points of control in inflammation," *Nature*, 420:846-852, 2002.

Osburn et al., "Genetic of pharmacologic amplification of Nrf2 signaling inhibits acute inflammatory liver injury in mice," *Toxicological Sciences*, 104:218-227, 2008.

Pollard, "Tumour-educated macrophages promote tumour progression and metastasis," *Nature Reviews*, 4:71-78, 2004.

Rangasamy et al., "Disruption of Nrf2 enhances susceptibility to severe airway inflammation and asthma in mice," *Journal of Experimental Medicine*, 202:47-59, 2005.

Thimmulappa et al., "Nrf2 is a critical regulator of the innate immune response and survival during experimental sepsis," *The Journal of Clinical Investigation*, 116:984-995, 2006.

Thimmulappa et al., "Nrf2-dependent protection from LPS induced inflammatory response and mortality by CDDO-imidazolide," *Biochem. Biophys. Res. Commun.*, 351:883-889, 2006.

Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," *Antioxidants & Redox Signaling*, 9:1-8, 2007.

Torres et al., "Inflammation and nitric oxide production in skeletal muscle of type 2 diabetic patients," *Journal of Endocrinology*, 181:419-427, 2004.

van Muiswinkel and Kuiperij, "The Nrf2-ARE signaling pathway: promising drug target to combat oxidative stress in neurodegenerative disorders," *Current Drug Target—CNS & Neurological Disorders*, 4:267-281, 2005.

Vodovotz et al., "Inducible nitric oxide synthase in tangle-bearing neurons of patients with Alzheimer's disease," *The Journal of Experimental Medicine*, 184:1425-1433, 1996.

Finlay et al., "The effects of A and C ring modification of oleanolic and ursolic acid on the inhibition of nitric oxide formation in mouse macrophages," 213th ACS National Meeting, San Francisco, California, abstract, Apr. 13-17, 1997.

Finlay et al., "The effects of A and C ring modification of oleanolic and ursolic acid on the inhibition of nitric oxide formation in mouse macrophages," 213th ACS National Meeting, San Francisco, California, poster, Apr. 13-17, 1997.

Honda et al., "New synthetic oleanane and ursane triterpenoids as inhibitors of nitric oxide production in mouse macrophages," 5th Chemical Congress of North America Meeting, Cancun, Mexico, abstract, Nov. 11-15, 1997.

Honda et al., "New synthetic oleanane and ursane triterpenoids as inhibitors of nitric oxide production in mouse macrophages," 5th Chemical Congress of North America Meeting, Cancun, Mexico, slides from oral presentation and poster, Nov. 11-15, 1997.

Office Action, in Canadian Patent App. No. 2,335,505, mailed May 4, 2009.

Office Action, in European Patent App. No. 01 989 130, mailed Mar. 24, 2009.

Response to Office Action, in Canadian Patent App. No. 2,335,505, dated Mar. 23, 2009.

Suh et al., "New triterpenoids as cancer preventive and anti-inflammatory agents," 88th AACR Meeting, San Francisco, California, abstract No. 1457, Mar. 1997.

Suh et al., "New triterpenoids as cancer preventive and anti-inflammatory agents," 88th AACR Meeting, San Francisco, California, poster, Mar. 1997.

Suh et al., "Novel triterpenoids suppress inducible nitric oxide synthase (INOS) and inducible cyclooxygenase (COX-2)," 89th AACR Meeting, New Orleans, Louisiana, slides from oral presentation, Mar. 28-Apr. 1, 1998.

"CDDO in treating patients with metastatic or unresectable solid tumors or lymphoma," http://www.clinicaltrials.gov/ct2/show/NCT00352040?term=CDDO&rank=1, Dec. 14, 2008.

"FDA mulls drug to slow late-stage Alzheimer's," http://www.cnn.com/2003/HEALTH/conditions/09/24/alzheimers.drug.ap/index.html, Retrieved on Sep. 23, 2003.

"Phase IIa trail to determine the effects of bardoxolone methyl on renal function in patients with diabetic nephropathy," http://www.clinicaltrials.gov/ct2/show/NCT00664027?term=rta&rank=10, Dec. 14, 2008.

"RTA 402 in advanced solid tumors or lymphoid malignancies," http://www.clinicaltrials.gov/ct2/show/NCT00508807?term=rta&rank=2&show_desc=Y, Dec. 14, 2008.

"Study to assess the safety, tolerability, and pharmacodynamics of RTA 402 in patients with hepatic dysfunction," http://www.clinicaltrials.gov/ct2/show/NCT00550849?term=rta&rank=4, Dec. 14, 2008.

Abraham and Kappas, "Heme oxygenase and the cardiovascular-renal system," *Free Radic. Biol. Med.*, 39 (1): 1-25, 2005.

Ahmad et al., "Triterpenoid CDDO-Me blocks the NF-κB pathway by direct inhibition of IKKβ on Cys-179", *J. Biol. Chem.*, 281: 35764-9, 2006.

Akrivakis et al., "Prolonged infusion of gemcitabine in stage IV breast cancer: a phase I study," *Anti-Cancer Drugs*, 10 (6): 525-531, 1999.

Alexander et al., "Synthesis and cytotoxic activity of two novel 1-dodecylthio-2-decyloxypropyl-3-phosphatidic acid conjugates with gemcitabine and cytosine arabinoside," *J. Med. Chem.*, 46 (19): 4205-4208, 2003.

Araujo et al., "Systemic rather than local heme oxygenase-1 overexpression improves cardiac allograft outcomes in a new transgenic mouse," *J. Immunol.*, 171 (3): 1572-1580, 2003.

Ardestani et al., "Effects of dexamethasone and betamethasone as COX-2 gene expression inhibitors on rigidity in a rat model of Parkinson's disease," *Indian J. Pharmacol.*, 39:235-9, 2007.

Ariga et al., "Role of sphingolipid-mediated cell death in neurodegenerative diseases," *Journal of Lipid Research*, 39:1-16, 1998.

Bach, "Heme oxygenase-1 and transplantation tolerance," *Hum. Immunol.*, 67 (6): 430-432, 2006.

Baker et al., "2'-Deoxy-2'-methylenecytidine and 2'-deoxy-2',2'-difluorocytidine 5'- diphosphates: potent mechanism-based inhibitors of ribonucleotide reductase," *J. Med. Chem.*, 34(6): 1884, 1991.

Balkwill et al., "Smoldering and polarized inflammation in the initiation and promotion of malignant disease," *Cancer Cell*, 7 (3): 211-217, 2005.

Beal, "Mitochondria, free radicals, and neurodegeneration," *Curr. Opin. Neurobiol.*, 6:661—666, 1996.

Bollag and Holdener, "Retinoids in cancer prevention and therapy," *Annals of Oncology*, 3:513-526, 1992.

Bruder and Caplan, "First bone formation and the dissection of an osteogenic lineage in the embryonic chick tibia is revealed by monoclonal antibodies against osteoblasts," *Bone*, 10:359-375, 1989.

Bruder and Caplan, "A monoclonal antibody against the surface of osteoblasts recognizes alkaline phosphatase isoenzymes in bone, liver, kidney, and intestine," *Bone*, 11:189-198, 1990.

Bruder et al., "Terminal Osteogenic cell differentiation in culture requires beta-glycerol phosphate," *Trans. Ortho. Res. Soc.*, 16:58, 1991.

Bruland et al., "Expression and characteristics of a novel human osteosarcoma-associated cell surface antigen," *Cancer Res.*, 48:5302-5308, 1988.

Cerwenka and Swain, "TGF-β1: immunosuppressant and viability factor for T lymphocytes," *Microbes and Infection*, 1: 1291-1296, 1999.

Chen et al., "Chondrogenesis in chick limb bud mesodermal cells: reciprocal modulation by activin and inhibin," *Exp. Cell. Res.*, 206:119-27, 1993.

Chen et al., "Stimulation of chondrogenesis in limb bud mesoderm cells by recombinant human bone morphogenetic protein 2B (BMP-2B) and modulation by transforming growth factor beta 1 and beta 2," *Exp. Cell. Res.*, 195:509-15, 1991.

Cheng et al., "Differentiation of human bone marrow osteogenic stromal cells in vitro: induction of the osteoblast phenotype by dexamethasone," *Endocrinology*, 134:277-86, 1994.

Chou et al., "Sterospecific Synthesis of 2-Deoxy-2,2-difluororibonolactone and its Use in the Preparation of 2'-Deoxy-2', 2'-difluoro-B—D-ribofuranosyl Pyrimidine Nucleosides: The Key Role of Selective Crystallization," *Synthesis*, 565-570, 1992.

Cripe, "Adult Acute Leukemia," *Current Problems in Cancer*, 21(1): 4-64, 1997.

Cui, "A material science perspective of pharmaceutical solids," *Int. J. Pharmceutics*, 339 (1-2): 3-18, 2007.

Di Stefano et al., "Inhibition of [3H]thymidine incorporation into DNA of rat regenerating liver by 2',2'-difluorodeoxycytidine coupled to lactosaminated poly-L-lysine," *Biochem. Pharmacol.*, 57 (7): 793-799, 1999.

Dragnev et al., "The retinoids and cancer prevention mechanisms," *The Oncologist*, 5:361-368, 2000.

Embleton et al., "Antitumour reactions of monoclonal antibody against a human osteogenic-sarcoma cell line," *Br. J. Cancer*, 43:4801-4805, 1981.

Gandhi et al., "Prolonged infusion of gemcitabine: clinical and pharmacodynamic studies during a phase I trial in relapsed acute myelogenous leukemia," *J. Clin. Oncol.*, 20 (3): 665-673, 2002.

Godoy et al., "Central and systemic IL-I exacerbates neurodegeneration and motor symptoms in a model of Parkinson's disease," *Brain*, 131:1880-1894, 2008.

Guo et al., "Selective Protection of 2',2'-Diflurodeoxycytidine (Gemcitabine)," *J. Org. Chem.*, 64: 8319-8322, 1999.

Guo et al., "Targeted delivery of a peripheral benzodiazepine receptor ligand-gemcitabine conjugate to brain tumors in a xenograft model," *Cancer Chemother. Pharmacol.*, 48 (2): 169-176, 2001.

Heiner et al., "Localization of GD2-specific monoclonal antibody 3F8 in human osteosarcoma," *Cancer Res.*, 47:5377-5384, 1987.

Hidvegi et al., "A low temperature method of isolating normal human articular chondrocytes," *Osteoarthr. Cartil.*, 14:89-93, 2006.

Honda et al., "An efficient synthesis of tricyclic compounds (±)-(4aβ, 8aβ, 10βaa)— 1,2,3,4,4a,6,7,8,8a,9,1-,10a-Dodecahydro-1,1,4a-Trimethyl-2-Oxophenanthrene-8a-Carboxolic acid, its methyl ester, and (±)-(4aβ,8aβ,10aα)-3,4,4a,6,7,8,8a,9,10,10a-Decahydro-8a-Hydroxymethyl-1,1,4a-Trimethylphenanthren-2(1H)-one," *Org. Prep. Proced Int.*, 37 (6):546-550, 2005.

Honda et al., "Design, synthesis, and biological evaluation of biotin conjugates of 2-cyano-3,12-dioxooleana-1,9(11)-dien-28-oic acid for the isolation of the protein targets,". J. Med. Chem., 47 (20): 4923-4932, 2004.

Honda et al., "Synthesis of a novel dicyano abietane analogue: a potential antiinflammatory agent," *J. Org. Chem.*, 71:3314-3316, 2006.

Hong et al., "Phase I trial of a novel oral NF-κB/pSTAT3 inhibitor RTA-402 in patients with solid tumors and lymphoid malignancies," 44th Annual Meeting of the American Society of Clinical Oncology, 2008.

Hosoi et al., "Detection of human osteosarcoma-associated antigen(s) by monoclonal antibodies," *Cancer Res.*, 42:654-661, 1982.

Huang et al., "Inhibitory effects of dietary curcumin on forestomach, duodenal, and colon carcinogenesis in mice," *Cancer. Res.*, 54:5841-5847, 1994.

Iguchi et al., "Lipid peroxidation and disintegration of the cell membrane structure in cultures of rat lung fibroblasts treated with asbestos," *J. Appl. Toxicol.*, 13:269-275, 1993.

Ishikawa et al., "Heme oxygenase-1 inhibits atherogenesis in Watanabe heritable hyperlipidemic rabbits," *Circulation*, 104 (15): 1831-1836, 2001.

Kasinski et al., "Inhibition of IkappaB kinase-nuclear factor-kappaB signaling pathway by 3,5-bis(2-flurobenzylidene)piperidin-4-one (EF24), a novel monoketone analog of curcumin," *Mol. Pharmacology*, 74(3): 654-661, 2008.

Klotz et al., "Selective expression of inducible nitric oxide synthase in human prostate carcinoma," *Cancer*, 82:1897-1903, 1998.

Konopleva et al., "Engraftment potential of AML progenitors into NOD/scid mice is dependent on baseline CXCR4 expression,"*Blood*, 94(Suppl 1):166b, Abstract #3916, 1999.

Kruger et al., "Up-regulation of heme oxygenase provides vascular protection in an animal model of diabetes through its antioxidant and antiapoptotic effects," *J. Pharmacol. Exp. Ther.*,319 (3): 1144-1152, 2006.

Lala et al., "Role of nitric oxide in tumor progression: lessons from experimental tumors," *Cancer and Metastasis Reviews*, 17 (1): 91-106, 1998.

Langille et al., "Differential effects of physiological concentrations of retinoic acid in vitro on chondrogenesis and myogenesis in chick craniofacial mesenchyme," *Differentiation*, 40:84, 1989.

Lawson et al., "Isolation and preliminary characterization of a monoclonal antibody that interacts preferentially with the liver isoenzyme of human alkaline phosphatase," *Clin. Chem.*, 31:381-385, 1985.

Leonard et al., "Expression of nitric oxide synthase in inflammatory bowel disease is not affected by corticosteroid treatment," *J. Clin. Pathol.*, , 51:750-753, 1998.

Liu et al., "Heme oxygenase-1 (HO-1) inhibits postmyocardial infarct remodeling and restores ventricular function," *FASEB J.*, 20 (2): 207-216, 2006.

Long, "Regulation of human bone marrow-derived osteoprogenitor cells by osteogenic growth factors ," *Clin. Invest.*, 95:881-887, 1995.

Luo et al., "IKK/NF-kappaB signaling: balancing life and death—a new approach to cancer therapy," *J. Clin. Invest.*, 115 (10): 2625-2631, 2005.

Maurel et al., "Phase I trial of weekly gemcitabine at 3-h infusion in refractory, heavily pretreated advanced solid tumors," *Anti-Cancer Drugs*, 12 (9): 713-717, 2001.

Morris et al., "Association of a functional inducible nitric oxide synthase promoter variant with complications in type 2 diabetes," *J. Mol. Med.*, 80 (2): 96-104, 2002.

Morse and Choi, "Heme oxygenase-1: from bench to bedside,"*Am. J. Respir. Crit. Care Med.*, 172 (6): 660-670, 2005.

Morse and Choi, "Heme oxygenase-1: the 'emerging molecule' has arrived," *Am. J. Respir. Crit. Care Med.*, 27(1):8-16, 2002.

Murray and Zweifel, "Preparation of Phenyl Cyanate and Its Utilization for the Synthesis of α, β-Unsaturated Nitriles," *Synthesis*, 150-151, 1980.*Synthesis*, 150-151, 1980.

Na and Surh et al., "Transcriptional regulation via cysteine thiol modification: a novel molecular strategy for chemoprevention and cytoprotection,"*Mol. Carcinog.*,45 (6): 368-380, 2006.

Office Action, in Canadian Patent App. No. 2,335,505, mailed Jan. 10, 2008.
Office Action, in Canadian Patent App. No. 2,335,505, mailed Nov. 23, 2006.
Office Action, in Canadian Patent App. No. 2,335,505, mailed Sep. 22, 2008.
Office Action, in Canadian Patent App. No. 2,430,454, mailed Jan. 20, 2009.
Office Action, in European Patent App. No. 01 989 130, mailed Jul. 31, 2008.
Office Action, in European Patent App. No. 03 729 681, mailed Nov. 6, 2008.
Office Action, in European Patent App. No. 99 928 731, mailed Aug. 1, 2008.
Office Action, in European Patent App. No. 99 928 731, mailed Dec. 9, 2008.
Office Action, in European Patent App. No. 99 928 731, mailed Dec. 15, 2004.
Office Action, in European Patent App. No. 99 928 731, mailed Feb. 14, 2007.
Office Action, in U.S. Appl. No. 09/335,003, mailed Aug. 28, 2000.
Office Action, in U.S. Appl. No. 09/335,003, mailed Mar. 15, 2001.
Office Action, in U.S. Appl. No. 09/335,003, mailed Nov. 2, 2000.
Office Action, in U.S. Appl. No. 09/927,081, mailed Feb. 22, 2002.
Office Action, in U.S. Appl. No. 09/998,009, mailed Apr. 4, 2007.
Office Action, in U.S. Appl. No. 09/998,009, mailed Jul. 11, 2005.
Office Action, in U.S. Appl. No. 09/998,009, mailed Jul. 14, 2004.
Office Action, in U.S. Appl. No. 09/998,009, mailed Jul. 3, 2006.
Office Action, in U.S. Appl. No. 09/998,009, mailed Mar. 24, 2004.
Office Action, in U.S. Appl No. 09/998,009, mailed Nov. 30, 2005.
Office Action, in U.S. Appl. No. 09/998,009, mailed Nov. 16, 2007.
Office Action, in U.S. Appl. No. 09/998,009, mailed Oct. 20, 2004.
Office Action, in U.S. Appl. No. 10/345,053, mailed Aug. 25, 2004.
Office Action, in U.S. Appl. No. 10/345,053, mailed Dec. 23, 2004.
Office Action, in U.S. Appl. No. 10/345,053, mailed Dec. 6, 2005.
Office Action, in U.S. Appl. No. 10/345,053, mailed Mar. 1, 2006.
Office Action, in U.S. Appl. No. 10/345,053, mailed May 31, 2005.
Office Action, in U.S. Appl. No. 10/395,372, mailed Apr. 28, 2006.
Office Action, in U.S. Appl. No. 10/395,372, mailed Aug. 4, 2005.
Office Action, in U.S. Appl. No. 10/395,372, mailed Dec. 20, 2006.
Office Action, in U.S. Appl. No. 10/395,372, mailed Feb. 7, 2007.
Office Action, in U.S. Appl. No. 10/395,372, mailed Jan. 28, 2004.
Office Action, in U.S. Appl. No. 10/395,372, mailed Jul. 9, 2004.
Office Action, in U.S. Appl. No. 10/395,372, mailed Jun. 12, 2006.
Office Action, in U.S. Appl. No. 10/395,372, mailed May 23, 2005.
Office Action, in U.S. Appl. No. 10/395,372, mailed Nov. 23, 2005.
Office Action, in U.S. Appl. No. 10/435,925, mailed Sep. 30, 2005.
Office Action, in U.S. Appl. No. 11/121,316, mailed Apr. 16, 2009.
Office Action, in U.S. Appl. No. 11/121,316, mailed Jul. 21, 2008.
Office Action, in U.S. Appl. No. 11/121,316, mailed Mar. 17, 2008.
Office Action, in U.S. Appl. No. 11/927,418, mailed Mar. 2, 2009.

Omura and Swern, "Oxidation of Alcohols by 'Activated' Dimethyl Sulfoxide. A Preparative, Steric and Mechanistic Study," *Tetrahedron*, 34:1651-1660, 1978.

Palcy and Goltzman, "Protein kinase signalling pathways involved in the up-regulation of the rat alpha1(I) collagen gene by transforming growth factor beta1 and bone morphogenetic protein 2 in osteoblastic cells," *Biochem. J.*, 343:21-27, 1999.

Patel et al., "Phase II clinical investigation of gemcitabine in advanced soft tissue sarcomas and window evaluation of dose rate on gemcitabine triphosphate accumulation," *J. Clin. Oncol.*, 19 (15): 3483-3489, 2001.

Paul et al., "Design and synthesis of a self-assembled photochemical dyad based on selective imidazole recognition," *Inorg. Chem.*, 41:3699-3704, 2002.

Paul et al., "Effective expression of small interfering RNA in human cells," *Nature Biotechnol.*, 20:505-508, 2002.

PCT, International Preliminary Examination Report, in Int. App. No. PCT/US1999/13635, mailed Sep. 6, 2000.
PCT, International Preliminary Examination Report, in Int. App. No. PCT/US2001/44541, mailed Jan. 15, 2004.
PCT, International Preliminary Examination Report, in Int. App. No. PCT/US2003/01307, mailed Oct. 20, 2003.

PCT, International Search Report, in Int. App. No. PCT/US1999/13635, mailed Oct. 20, 1999.
PCT, International Search Report, in Int. App. No. PCT/US2001/44541, mailed Jan. 24, 2003.
PCT, International Search Report, in Int. App. No. PCT/US2003/01307, mailed May 12, 2003.
PCT, Written Opinion, in Int. App. No. PCT/US1999/13635, mailed May 15, 2000.
PCT, Written Opinion, in Int. App. No. PCT/US2001/44541, mailed Sep. 23, 2003.
Petition Decision, issued in U.S. Appl. No. 10/345,053, mailed May 22, 2006.
Response to Office Action, in Canadian Patent App. No. 2,335,505, dated Jul. 10, 2008.
Response to Office Action, in Canadian Patent App. No. 2,335,505, dated May 11, 2007.
Response to Office Action, in European Patent App. No. 01 989 130, dated Sep. 5, 2008.
Response to Office Action, in European Patent App. No. 99 928 731, dated Oct. 1, 2008.
Response to Office Action, in European Patent App. No. 99 928 731, dated Mar. 9, 2009.
Response to Office Action, in European Patent App. No. 99 928 731, dated Jun. 23, 2005.
Response to Office Action, in European Patent App. No. 99 928 731, dated Aug. 14, 2007.
Response to Office Action, in U.S. Appl. No. 09/335,003, dated Sep. 28, 2000.
Response to Office Action, in U.S. Appl. No. 09/335,003, dated Mar. 2, 2001.
Response to Office Action, in U.S. Appl. No. 09/335,003, dated Apr. 16, 2001.
Response to Office Action, in U.S. Appl. No. 09/998,009, dated Apr. 21, 2004.
Response to Office Action, in U.S. Appl. No. 09/998,009, dated Sep. 14, 2004.
Response to Office Action, in U.S. Appl. No. 09/998,009, dated Apr. 19, 2005.
Response to Office Action, in U.S. Appl. No. 09/998,009, dated Oct. 11, 2005.
Response to Office Action, in U.S. Appl. No. 09/998,009, dated Mar. 30, 2006.
Response to Office Action, in U.S. Appl. No. 09/998,009, dated Jan. 3, 2007.
Response to Office Action, in U.S. Appl. No. 09/998,009, dated Sep. 4, 2007.
Response to Office Action, in U.S. Appl. No. 09/998,009, dated Feb. 18, 2008.
Response to Office Action, in U.S. Appl. No. 10/345,053, dated Sep. 24, 2004.
Response to Office Action, in U.S. Appl. No. 10/345,053, dated Mar. 23, 2005.
Response to Office Action, in U.S. Appl. No. 10/345,053, dated Sep. 3, 2005.
Response to Office Action, in U.S. Appl. No. 10/345,053, dated Feb. 6, 2006.
Response to Office Action, in U.S. Appl. No. 10/395,372, dated Apr. 28, 2004.
Response to Office Action, in U.S. Appl. No. 10/395,372, dated Nov. 9, 2004.
Response to Office Action, in U.S. Appl. No. 10/395,372, dated Jul. 25, 2005.
Response to Office Action, in U.S. Appl. No. 10/395,372, dated Nov. 23, 2005.
Response to Office Action, in U.S. Appl. No. 10/395,372, dated Apr. 21, 2006.
Response to Office Action, in U.S. Appl. No. 10/395,372, dated Oct. 12, 2006.
Response to Office Action, in U.S. Appl. No. 10/395,372, dated Jan. 12, 2007.
Response to Office Action, in U.S. Appl. No. 10/395,372, dated Feb. 14, 2007.
Response to Office Action, in U.S. Appl. No. 10/435,925, dated Mar. 30, 2005.
Response to Office Action, in U.S. Appl. No. 11/121,316, dated Apr. 4, 2008.
Response to Office Action, in U.S. Appl. No. 11/121,316, dated Dec. 19, 2008.
Response to Office Action, in U.S. Appl. No. 11/672,449, dated Dec. 15, 2008.
Response to Office Action, in U.S. Appl. No. 11/927,418, dated Apr. 2, 2009.
Response to Written Opinion, in Int. App. No. PCT/US1999/13635, dated Jul. 14, 2000.
Richardson et al., "Synthesis and restriction enzyme analysis of oligodeoxyribonucleotides containing the anti-cancer drug 2',2'-difluoro-2'-deoxycytidine," *Nucleic Acid Res.*, 20 (7): 1763-1769, 1992.
Rizzieri et al., "Phase I evaluation of prolonged-infusion gemcitabine with mitoxantrone for relapsed or refractory acute leukemia," *J. Clin. Oncol.*, 20 (3): 674-679, 2002.
Robbins et al., "Inflammation and Repair," In: Basic Pathology 3rd Edition, W.B. Saunders Company, Chapter 2, p. 28, 1981.
Sacerdoti et al., "Heme oxygenase overexpression attenuates glucose-mediated oxidative stress in quiescent cell phase: linking heme to hyperglycemia complications," *Curr. Neurovasc. Res.*, 2(2): 103-111, 2005.
Satoh et al., "Activation of the Keap1/Nrf2 pathway for neuroprotection by electrophilic [correction of electrophillic] phase II inducers," *PNAS*, 103 (3): 768-773, 2006.
Shull et al., "Identification of a vitamin D-responsive protein on the surface of human osteosarcoma cells," *Proc. Natl. Acad. Sci. USA*, 86:5405-5410, 1989.
Shull et al., "Morphologic and biochemical studies of canine mucopolysaccharidosis I," *Am. J. Pathol.*, 114:487-495, 1984.
Singh and Evans, "Nitric oxide, the biological mediator of the decade: fact or fiction?" *Eur. Respir. J.*, 10:699-707, 1997.
Sive et al., "Expression of chondrocyte markers by cells of normal and degenerate intervertebral discs," *Mol. Pathol.*, 55:91-97, 2002.
Sporn et al., "Transforming growth factor-beta: biological function and chemical structure," *Science*, 233:532-534, 1986.
Steadman's Medical Journal 23rd Edition, The Williams & Wilkins Company, p. 401, 1976.
Strejan et al., "Suppression of chronic-relapsing experimental allergic encephalomyelitis in strain-13 guinea pigs by administration of liposome-associated myelin basic protein," *J. Neuroimmunol.*, 7 (1): 27, 1984.
Suh et al., "Novel triterpenoids suppress inducible nitric oxide synthase (iNOS) and inducible cyclooxygenase (COX-2) in mouse macrophages," *Cancer Research*, 58:717-723, 1998.
Suh et al., "New triterpenoids as cancer preventive and anti-inflammatory agents," *Proceedings of the American Association for Cancer Research*, Abstract No. 1457, 38: 216, 1997.
Supplementary European Search Report, issued in European Patent App. No. 01 989 130, mailed Aug. 9, 2007.
Supplementary European Search Report, issued in European Patent App. No. 03 729 681, mailed Aug. 3, 2006.
Syftestad et al., "The in vitro chondrogenic response of limb-bud mesenchyme to a water-soluble fraction prepared from demineralized bone matrix," *Differentiation*, 29:230, 1985.
Tempero et al., "Randomized phase II comparison of dose-intense gemcitabine: thirty-minute infusion and fixed dose rate infusion in patients with pancreatic adenocarcinoma," *J. Clin. Oncol.*, 21 (18): 3402-3408, 2003.
Tenenbaum and Heersche, "Differentiation of osteoblasts and formation of mineralized bone in vitro," *Calcif Tissue Int.*, 34:76, 1982.
Therasse et al., "New guidelines to evaluate the response to treatment in solid tumors. European Organization for Research and Treatment of Cancer, National Cancer Institute of the United States, National Cancer Institute of Canada," *J. Natl. Cancer Instit.*, 92 (3): 205, 2000.
Toriumi et al., "Mandibular reconstruction with a recombinant bone-inducing factor. Functional, histologic, and biomechanical evaluation," *Arch. Otolaryngol. Head Neck Surg.*, 117:1101-1112, 1991.

Tran et al., "The synthetic triterpenoid CDDO-methyl ester modulates microglial activities, inhibits TNF production, and provides dopaminergic neuroprotection," *Journal of Neuroinflammation*, 5:1-14, 2008.

Tsai et al., "Monoclonal antibody to human osteosarcoma: a novel Mr 26,000 protein recognized by murine hybridoma TMMR-2," *Cancer Res.*, 50:152-161, 1990.

Turksen et al., "Isolation of monoclonal antibodies recognizing rat bone-associated molecules in vitro and in vivo," *J. Histochem. Cytochem.*, 40:1339-1352, 1992.

U.S. Appl. No. 60/955,939, filed Aug. 15, 2007.

Veerman et al., "Antitumor activity of prolonged as compared with bolus administration of 2',2'-difluorodeoxycytidine in vivo against murine colon tumors," *Cancer Chemother. Pharmacol.*, 38 (4): 335-342, 1996.

Vukicevic et al., "Stimulation of the expression of osteogenic and chondrogenic phenotypes in vitro by osteogenin," *Proc. Natl. Acad. Sci. USA*, 86:8793-7, 1989.

Walsh et al., "Monoclonal antibodies with selective reactivity against osteoblasts and osteocytes in human bone," *J. Bone Miner Res.*, 9:1687-1696, 1994.

Yore et al., "The synthetic triterpenoid 1 -[2-cyano-3,12-dioxooleana-1,9(11)-dien-28-oyl]imidazole blocks nuclear factor-kappaB activation through direct inhibition of IkappaB kinase beta," *Mol. Cancer Ther.*, 5 (12): 3232-3239, 2006.

Yu and Kensler, "Nrf2 as a target for cancer chemoprevention," *Mutat. Res.*, 591 (1-2): 93-102, 2005.

Yue et al., "Depletion of intracellular glutathione contributes to JNK-mediated death receptor 5 upregulation and apoptosis induction by the novel synthetic triterpenoid methyl-2-cyano-3, 12-dioxooleana-1, 9-dien-28-oate (CDDO-Me).," *Cancer & Biology Therapy*, 5(5):492-497, 2006.

Zhou et al., "Carbon monoxide suppresses bleomycin-induced lung fibrosis," *Am. J. Pathol.*, 166 (1): 27-37, 2005.

Zhou et al., "Physical stability of amorphous pharmaceuticals: Importance of configurational thermodynamic quantities and molecular mobility," *J. Pharmaceutical Sciences*, 91(8): 1863-1872, 2002.

Finlay et al., "The effects of A and C ring modification of oleanolic and ursolic acid on the inhibition of nitric oxide formation in mouse macrophages," 213th ACS National Meeting, San Francisco, California, abstract, Apr. 13-17, 1997.

Finlay et al., "The effects of A and C ring modification of oleanolic and ursolic acid on the inhibition of nitric oxide formation in mouse macrophages," 213th ACS National Meeting, San Francisco, California, poster, Apr. 13-17, 1997.

Honda et al., "New synthetic oleanane and ursane triterpenoids as inhibitors of nitric oxide production in mouse macrophages," 5th Chemical Congress of North America Meeting, Cancun, Mexico, abstract, Nov. 11-15, 1997.

Honda et al., "New synthetic oleanane and ursane triterpenoids as inhibitors of nitric oxide production in mouse macrophages," 5th Chemical Congress of North America Meeting, Cancun, Mexico, slides from oral presentation and poster, Nov. 11-15, 1997.

Office Action, in Canadian Patent App. No. 2,335,505, mailed May 4, 2009.

Office Action, in European Patent App. No. 01 989 130, mailed Mar. 24, 2009.

Response to Office Action, in Canadian Patent App. No. 2,335,505, dated Mar. 23, 2009.

Suh et al., "New triterpenoids as cancer preventive and anti-inflammatory agents," 88th AACR Meeting, San Francisco, California, abstract No. 1457, Mar. 1997.

Suh et al., "New triterpenoids as cancer preventive and anti-inflammatory agents," 88th AACR Meeting, San Francisco, California, poster, Mar. 1997.

Suh et al., "Novel triterpenoids suppress inducible nitric oxide synthase (INOS) and inducible cyclooxygenase (COX-2)," 89th AACR Meeting, New Orleans, Louisiana, slides from oral presentation, Mar. 28-Apr. 1, 1998.

\* cited by examiner

FIG. 1. TBE-3 Suppress Formation of iNOS and COX-2 mRNA in RAW 264.7 Cells
Northern Blot
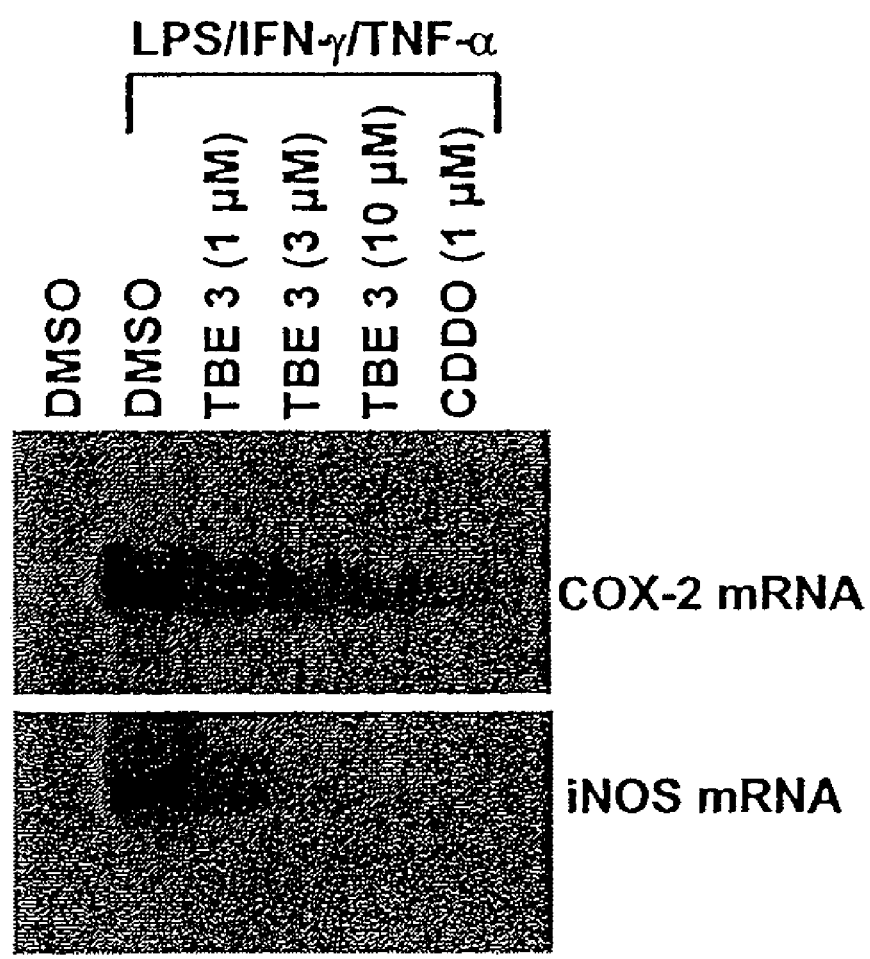

FIG. 2. Inhibition of Estrogen-Stimulated Growth of MCF-7 Breast Cancer Cells (ER-positive) by TBE-3 and 5
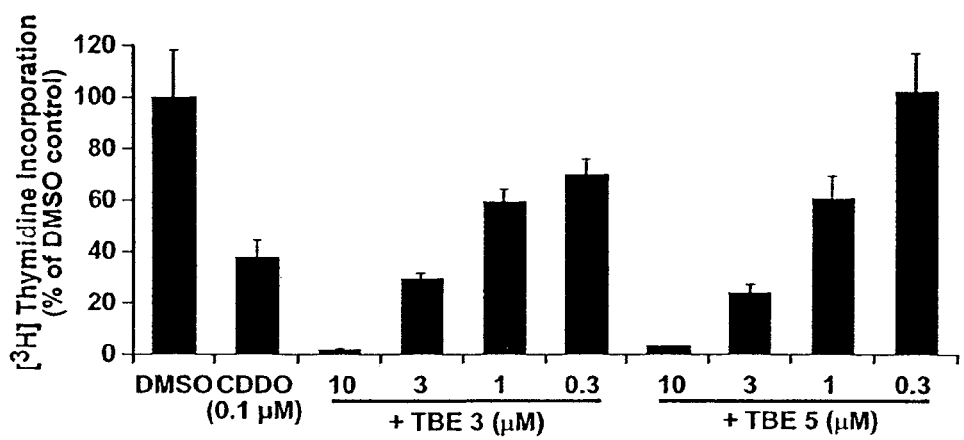

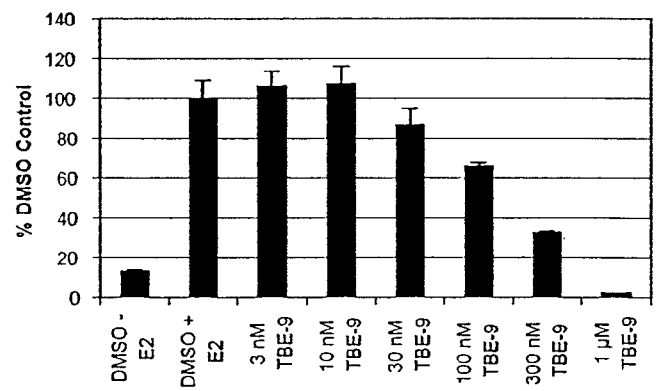
FIG. 3. Inhibition of Estrogen-Stimulated Growth of MCF-7 Breast Cancer Cells (ER-positive) by TBE-9

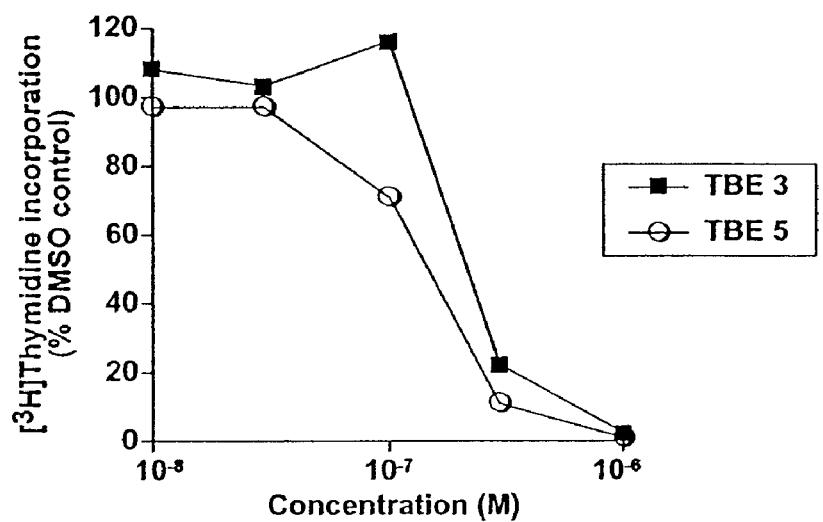
FIG. 4. TBE Compounds Inhibit Proliferation of NRP-152 Prostate Cells

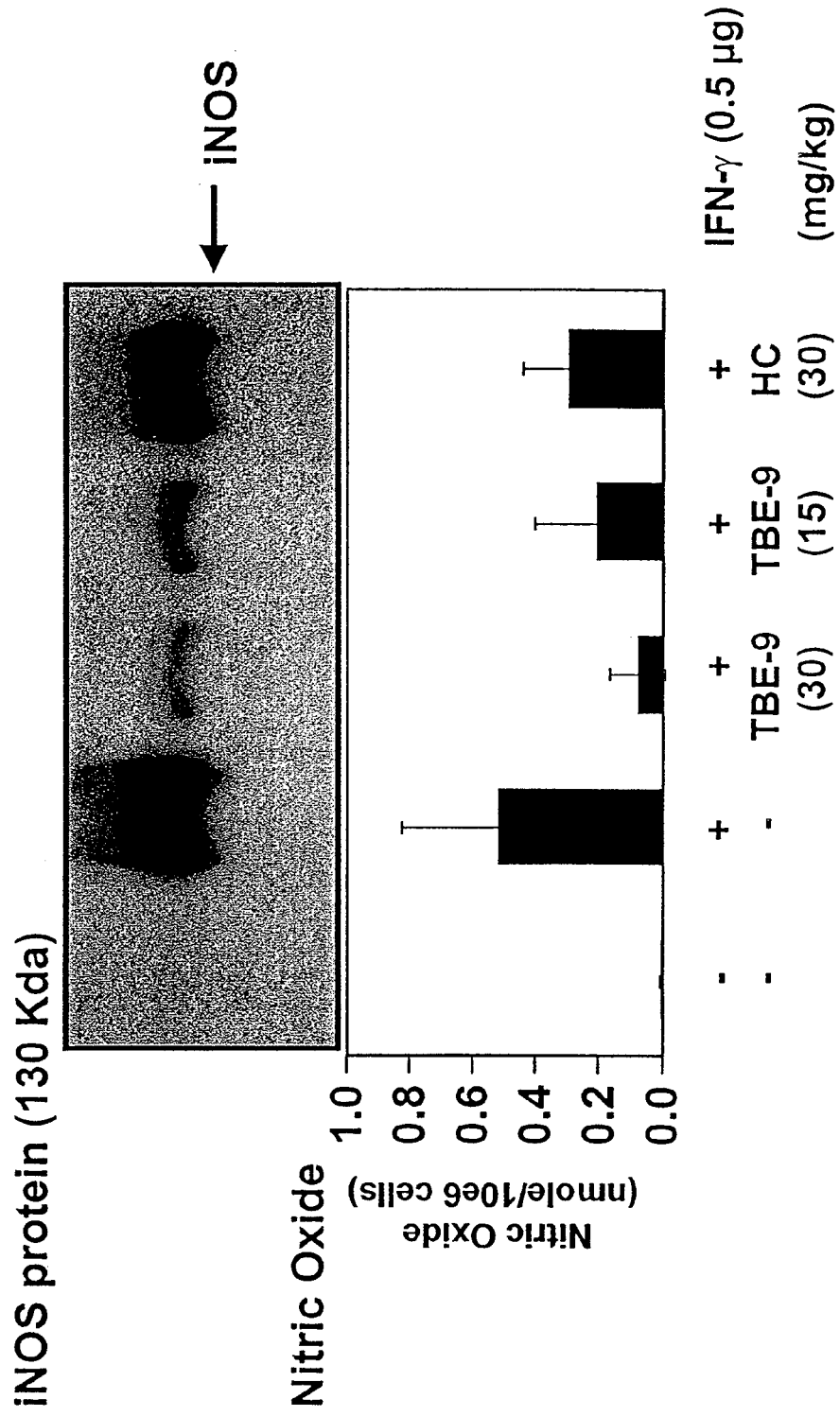
FIG. 5 In Vivo Anti-Inflammation Activity of TBE-9 in CD-1 Mice

TRICYCLIC-BIS-ENONE DERIVATIVES AND METHODS OF USE THEREOF

The present application is a divisional of U.S. Application Ser. No. 10/345,053 filed Jan. 15, 2003, now U.S. Pat. No. 7,176,237, which claims priority to provisional U.S. Patent Application Ser. No. 60/348,594 filed Jan. 15, 2002; provisional U.S. Patent Application Ser. No. 60/376,040, filed Apr. 26, 2002 and provisional U.S. Patent Application Ser. No. 60/402,966, filed Aug. 13, 2002. The entire text of each of the above referenced applications is incorporated herein by reference and without disclaimer.

This invention was made with government support under grant number 1R01CA78814 awarded by the National Institutes of Health and the National Foundation for Cancer Research. The government has certain rights in the invention.

BACKGROUND OF THE INVENTION

I. Field of the Invention

The present invention provides novel tricyclic-bis-enone derivatives (TBEs), as well as the process for the preparation of such TBEs, for prevention and/or treatment of cancer, Alzheimer's disease, Parkinson's disease, multiple sclerosis, amyotropic lateral sclerosis, rheumatoid arthritis, inflammatory bowel disease, and other diseases whose pathogenesis is believed to involve excessive production of either nitric oxide (NO) or prostaglandins.

II. Description of Related Art

One of the major needs in clinical oncology is the development of effective and safe new agents for chemoprevention. In particular, there is a need for chemopreventative agents targeted at mechanisms known to be involved in the process of carcinogenesis. In recent years, there has been a resurgence of interest in the study of mechanisms of inflammation that relate to carcinogenesis and in the use of such mechanisms as the basis for development of new chemopreventative agents.

The concept that inflammation and carcinogenesis are related phenomena has been the subject of many studies that have attempted to link these two processes in a mechanistic fashion (Sporn and Roberts, 1986; Ohshima and Bartsch, 1994). The enzymes that mediate the constitutive synthesis of NO and prostaglandins from arginine and arachidonate, respectively, have relative little significance for either inflammation or carcinogenesis. In contrast, inducible nitric oxide synthase (iNOS) and inducible cycloxygenase (COX-2) both have critical roles in the response of tissues to injury or infectious agents (Moncada et al., 1991; Nathan and Xie, 1994; Tamir and Tannebaum, 1996). These inducible enzymes are essential components of the inflammatory process, the ultimate repair of injury, and carcinogenesis. While physiological activity of iNOS and COX-2 may provide a definite benefit to the organism, aberrant or excessive expression of either iNOS or COX-2 has been implicated in the pathogenesis of many disease processes, particularly in chronic degeneration of the central nervous system, carcinogenesis, septic shock, cardiomyopathy, and rheumatoid arthritis.

The need for new agents to prevent and treat cancer is readily evident from the continuing high mortality rates for the common forms of epithelial cancer, such as carcinoma of the lung, colon, breast, and prostate. As methods of genetic testing can identify increasing numbers of people who are at high risk for the development of cancers, it becomes increasingly important to discover new pharmacologic agents that can be used interventionally to prevent this outcome, well before the occurrence of malignant invasive disease. The same is true for degenerative diseases, inflammatory diseases and immune diseases that involve increased NO or prostaglandin production. Therefore, the art lacks compounds for the chemoprevention of cancer and the other diseases or conditions described above that can be produced by efficient and cost effective methods and are also easy to administer.

SUMMARY OF THE INVENTION

The present invention overcomes defects in the art and provides compounds for the treatment as well as chemoprevention of cancer and the other diseases or conditions that result from the overproduction of nitric oxide (NO) or prostaglandins or the overexpression of iNOS and COX-2. The invention advantageously provides compounds and for use in the prevention and treatment of the above described conditions that are water soluble thereby allowing the preparation of pharmaceutical formulations that are easy to administer. The invention also provides methods for the synthesis of these compounds by that are efficient, cheap and amenable to scale up for large scale manufacturing.

Thus, in some embodiments of the present invention, there is provided a compound having the formula:

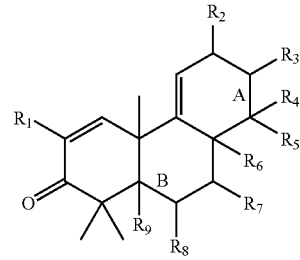

wherein $R_1$ is CN, or $CO_2H$; $R_2$ is =O; $R_3$ is H, $CH_3$, $CO_2H$, $CO_2Me$, $CONH_2$, CN, or $(CH_2)_n$—$R_{10}$; $R_4$ is H, OH, OAc, $CH_3$, $CO_2H$, $CO_2Me$, $CONH_2$, CN, or $(CH_2)_n$—$R_{10}$; $R_5$ is H, $CH_3$, $CH_2CH_3$, or part of a double-bond A; $R_6$ is H, $CH_3$, $CO_2H$, $CO_2Me$, $CONH_2$, CN, $CH_2X$, $CH_2OAc$, $CH_2OH$, CHO, $CH_2NH_2$, $(CH_2)_n$—$R_{10}$, $CO_2R$ (esters), —$CH_2OR$ (esters and ethers), $CH_2OSiMe_2$(t-Bu), —$CONR_{11}R_{12}$ (amides), $CH_2NHCOOR$ (carbamates) or $CH_2NHCOO$(t-Bu); $R_7$ is H, =O; $R_8$ is H, OH, forms an epoxide with $R_9$, or forms part of a double-bond B; $R_9$ is H, forms an epoxide with $R_8$, or forms part of a double-bond B; $R_{10}$ is $CH_3$, $CO_2H$, $CO_2CH_3$, $CO_2CH_2CH_3$, $CONH_2$, CN, $NH_2$, $CH(CH_3)_2$, $NR_{11}R_{12}$, pyrrolidine, piperidine, pyrazine, imidazole, pyrazole, triazole, tetrazole, substituted at N with $R_{13}$, or 1,4-oxazine, where $R_{11}$, $R_{12}$, and $R_{13}$ are alkyl; X is F, Cl, or Br; n is 0-20; and A & B independently signify a single-bond or double-bond; or any optically active form thereof such as optical isomers (−)-, (+)-; or a (±)-racemic compound; or a pharmaceutically acceptable salt thereof. These compounds, their derivatives or analogs, as well as their isomers, stereoisomers, optical isomers, racemic compounds, and mixtures thereof, are provided and called tricyclic-bis-enone (TBE) compounds and are also referred to as the "TBE compounds of the invention" or "compounds of the invention."

In some specific embodiments, the invention provides the following TBE compounds and pharmaceutically acceptable salts or formulations thereof:

(±)-TBE-1 which has the formula:

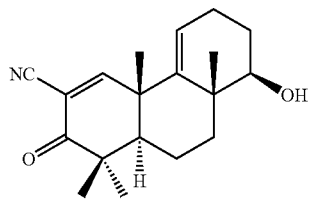

(±)-TBE-2 which has the formula:

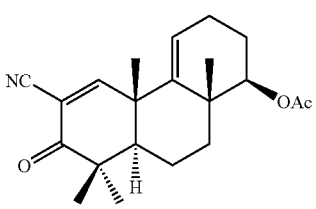

(±)-TBE-3 which has the formula:

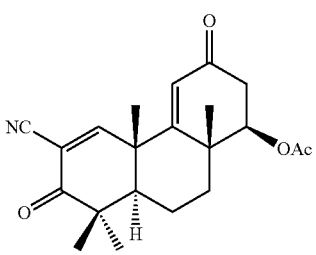

(±)-TBE-4 which has the formula:

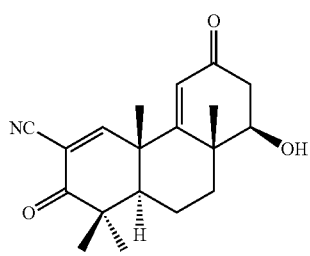

(±)-TBE-5 which has the formula:

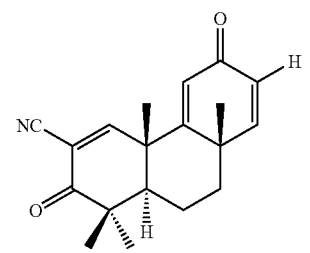

(−)-TBE-5 which has the formula:

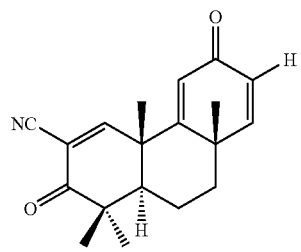

(+)-TBE-5 which has the formula:

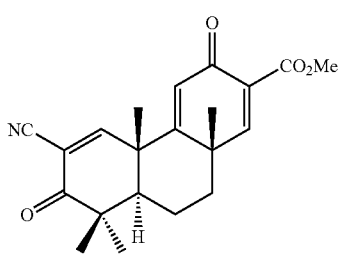

(±)-TBE-6 which has the formula:

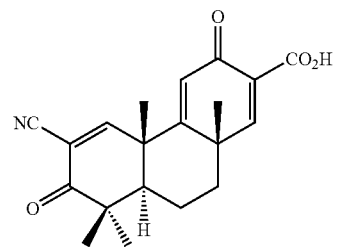

(±)-TBE-7 which has the formula:

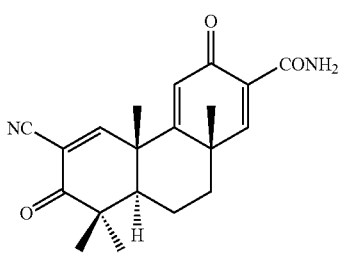

(±)-TBE-8 which has the formula (±)-TBE-9 which has the formula:

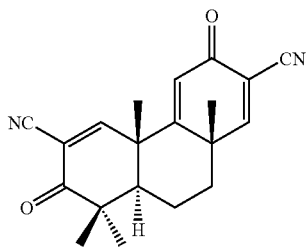

(±)-TBE-10 which has the formula:

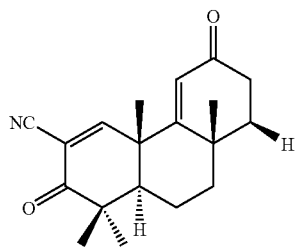

(±) TBE-12 which has the formula:

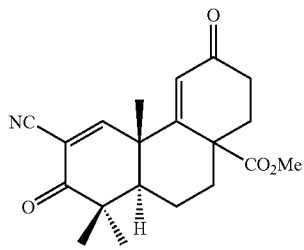

or a pharmaceutically acceptable salt or formulation thereof.

Further provided by the invention are TBE compounds, TBE-13-19, optical isomers, stereoisomers, racemic forms, enentiomers, and pharmaceutically acceptable salts and formulations thereof.

Thus, there is provided a compound (±)-TBE-13 which has the formula:

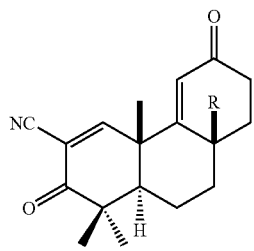

wherein R=CH$_2$OH, or a pharmaceutically acceptable salt thereof.

Compound (±)-TBE-14 which has the formula:

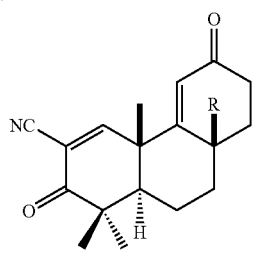

wherein R=CN or a pharmaceutically acceptable salt thereof.

Compound (±)-TBE-15 which has the formula:

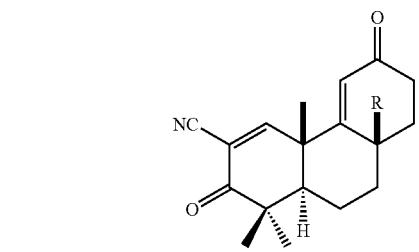

wherein R=CH$_2$OSiMe$_2$(t-Bu), or a pharmaceutically acceptable salt thereof.

Compound (±)-TBE-16 which has the formula:

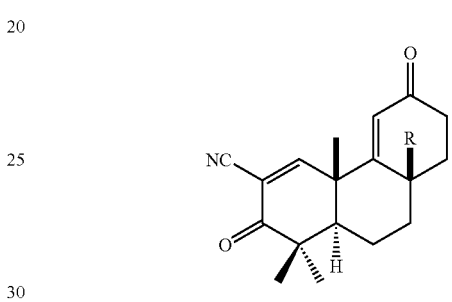

wherein R=CH$_2$NHCOO(t-Bu), or a pharmaceutically acceptable salt thereof.

Compound (±)-TBE-17 which has the formula:

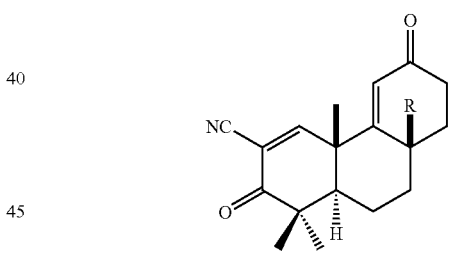

wherein R=CH$_2$NH$_2$, or a pharmaceutically acceptable salt thereof.

Compound (±)-TBE-18 is an example of a pharmaceutically acceptable salt of TBE 17 and has the formula:

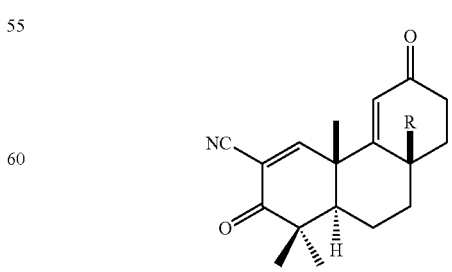

wherein R=CH$_2$NH$_2$.HCl.

Compound (±)-TBE-19 which has the formula:

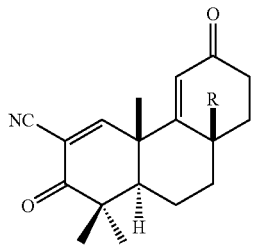

wherein R=$CO_2H$, or a pharmaceutically acceptable salt thereof.

One of skill in the art will recognize that or optically active forms such as the (−)-, and (+)-, forms; (+) and (−) enantiomers; (±) racemic forms of all the above TBE compounds and their derivatives are also provided. The invention also contemplates that all these TBE compounds and isomers and stereoisomers thereof can further be constituted into pharmaceutically acceptable formulations.

Also provided are various tricyclic-bis-enone compositions, comprising one or more of the compounds described above, effective for inhibiting IFN-γ-induced NO production in macrophages or RAW cells, the composition having an $IC_{50}$ value of at least less than about 0.7 μM. In specific embodiments, the compositions may have an $IC_{50}$ value of at least less than about 0.1, 0.05, 0.01, 0.005, or 0.001 μM, be optically pure, be predominantly the (+) enantiomer, predominantly the (−) enantiomer, or a racemic mixture. The composition may further be water soluble.

The invention also provides methods of treating a subject having a condition or disease that is characterized by the excess of NO or one or more prostaglandin comprising administering a therapeutically effective amount of one or more of the compounds set out above. The subject may be a human or an animal. In some embodiments, the disease may be a cancer such as, cancer of the brain, lung, liver, spleen, kidney, lymph node, small intestine, pancreas, blood cell, bone, colon, stomach, breast, endometrium, prostate, testicle, ovary, central nervous system, skin, head and neck, esophagus, or bone marrow. In other embodiments, the disease or condition that afflicts the subject may be an inflammatory disease, such as rheumatoid arthritis or inflammatory bowel disease. In yet other embodiments, the disease may be a neurodegenerative disease, such as Alzheimer's disease, Parkinson's disease, multiple sclerosis or amyotrophic lateral sclerosis. The subject may also be a human or an animal that may only be at risk for the development of cancer, inflammatory disease, or neurodegenerative disease and the treatment is therefore prophylactic. In general, the therapeutic and prophylactic methods of the invention are applicable to a subject that either has or has a propensity to develop a disease or a condition that may have a pathogenesis involving the excessive production of nitric oxide or prostaglandins or the excessive expression of the iNOS or the COX-2 genes.

In another embodiment, the invention provides methods for preventing or treating a disorder characterized by the overexpression of iNOS or COX-2 genes comprising administering to a subject or a patient with such a disorder a therapeutically effective amount of a pharmaceutical composition containing at least one or more of compounds described above.

Also provided are methods of modulating transcription or translation of iNOS or COX-2 genes in a subject comprising administering to the subject a pharmaceutically effective amount of a composition containing one or more of the compounds described above.

In yet other embodiments, the invention provides methods of modulating excessive nitric oxide or prostaglandin formation in a subject comprising administering to the subject an effective amount of a composition containing one or more of the compounds described above.

In yet other embodiments, the invention provides several methods for preparing the compounds described above. These methods are described in detail in the section entitled Examples. The methods of the invention for producing TBE compounds are cost-effective, efficient and amenable to large-scale manufacturing.

In still other embodiments, the invention provides yet other efficient and cost-effective methods comprising the use of novel tricyclic intermediates for the synthesis of the TBE compounds of the invention. These intermediates and their synthesis are described in detail in Example 2. Methods for synthesis of the TBE compounds using these intermediates are detailed in Examples 2 & 3. Thus, in some embodiments the following intermediates are provided:

Intermediate compound (23) of the formula:

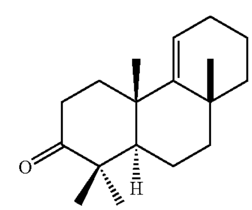

also called (±)-(4aβ,8aβ,10aα)-3,4,4a,6,7,8,8a,9,10,10a-Decahydro-1,1,4a,8a-tetramethylphenanthren-2(1H)-one.

Intermediate compound (29a) of the formula:

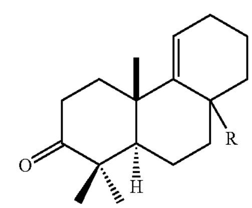

wherein R=$CO_2H$.

also called (±)-(4aβ,8aβ,10aα)-1,2,3,4,4a,6,7,8,8a,9,10,10a-Dodecahydro-1,1,4a-trimethyl-2-oxo-phenanthrene-8a-carboxylic acid, Intermediate compound (29b) of the formula:

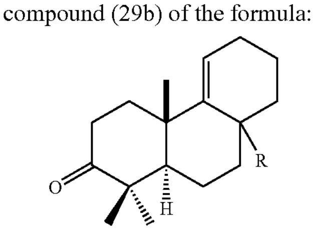

wherein R=$CO_2Me$.

also called methyl ester of (±)-(4aβ,8aβ,10aα)-1,2,3,4,4a,6,7,8,8a,9,10,10a-Dodecahydro-1,1,4a-trimethyl-2-oxo-phenanthrene-8a-carboxylic acid.

Intermediate compound (29c) of the formula:

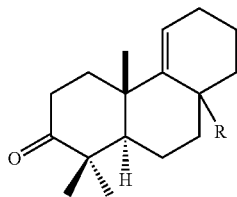

wherein R=CH$_2$OH.

also called (±)-(4aβ,8aβ,10aα)-3,4,4a,6,7,8,8a,9,10,10a-Decahydro-8a-hydroxymethyl-1,1,4a-trimethylphenanthren-2(1H)-one.

BRIEF DESCRIPTION OF THE DRAWINGS

The following drawings form part of the present specification and are included to further demonstrate certain aspects of the present invention. The invention may be better understood by reference to one of these drawings in combination with the detailed description of specific embodiments presented herein.

FIG. 1. TBE-3 Suppresses the Formation of iNOS and COX-2 mRNA in RAW 264.7 Cells FIG. 2. Inhibition of Estrogen-Stimulated Growth of MCF-7 Breast Cancer Cells (ER-positive) by TBE-3 and 5

FIG. 3. Inhibition of Estrogen-Stimulated Growth of MCF-7 Breast Cancer Cells (ER-positive) by TBE-9

FIG. 4. TBE Compounds Inhibit Proliferation of NRP-152 Prostate Cells

FIG. 5. In vivo Anti-Inflammation Activity of TBE-9 in CD-1 Mice

DESCRIPTION OF ILLUSTRATIVE EMBODIMENTS

I. The Present Invention

Within the past few years, there has been increasing interest in the development of selective COX-2 and iNOS inhibitors for prevention of cancer, especially in the colon. However, there are various types of cancers as well as inflammatory and neurodegenerative diseases characterized by COX-2 and iNOS overexpression and the art still lacks effective agents that can be synthesized by cost-effective methods and are suitable for pharmaceutical formulation. The present invention provides compounds that are tricyclic-bis-enone (TBE) derivatives that block the formation of the enzymes COX-2 and iNOS. The TBEs represent a novel class of agents capable of suppressing the expression of the COX-2 and iNOS genes. Thus, the use of these compounds for the treatment of cancer and other diseases characterized by COX-2 and iNOS overexpression are provided. In addition, the present invention also provides several novel and cost-effective methods for the synthesis of TBEs, some of which utilize novel intermediates.

II. Definitions

As used herein, the term "organic moiety" is intended to include carbon based functional groups such as alkyl, alkylamino, alkoxy, aryl, aralkyl, aryloxy, alkylthio, and alkylcarboxyl.

As used herein, the term "inorganic moiety" is intended to include non carbon-based groups or elements such as hydrogen, halo, amino, nitro, thiol, and hydroxyl.

As used herein, the term "electron withdrawing moiety" is known in the art, and refers to a group which has a greater electron-withdrawing than hydrogen. A variety of electron-withdrawing groups are known, and include halogens (e.g., fluoro, chloro, bromo, and iodo groups), nitro, cyano, —NR$_3^+$, —SR R$_2^+$, —NH R$_3^+$, —SO$_2$ R, —SO$_2$ Ar, —COOH, —OAr, —COOR, —OR, —COR, —SH, —SR, —OH, —Ar, and —CH$_2$CR$_2$, where Ar is aryl, and R represents any appropriate organic or inorganic moiety and, preferably, alkyl moiety.

As used herein, the term "halosubstituted alkyl moieties" is intended to include alkyl moieties which have halogen moieties in the place of at least one hydrogen. As used herein, the term "amino" means —NH$_2$; the term "nitro" means —NO$_2$; the term "halogen" designates —F, —Cl, —Br or —I; the term "thiol" means SH; and the term "hydroxyl" means —OH. Thus, the term "alkylamino" as used herein means an alkyl group, as defined above, having an amino group attached thereto. The term "alkylthio" refers to an alkyl group, as defined above, having a sulfhydryl group attached thereto. The term "alkylcarboxyl" as used herein means an alkyl group, as defined above, having a carboxyl group attached thereto.

The term "aromatic group" is intended to include unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —CF$_3$, —CN, or the like.

The term "alkyl" refers to the saturated aliphatic groups, including straight-chain alkyl groups, branched-chain alkyl groups, cycloalkyl (alicyclic) groups, alkyl substituted cycloalkyl groups, and cycloalkyl substituted alkyl groups.

Moreover, the term "alkyl" (including "lower alkyl") as used throughout the specification and claims is intended to include both "unsubstituted alkyls" and "substituted alkyls," the latter of which refers to alkyl moieties having moieties replacing a hydrogen on one or more carbons of the hydrocarbon backbone. Such moieties can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the moieties described above. An "aralkyl" moiety is an alkyl substituted with an aryl (e.g., phenylmethyl (benzyl)).

The term "alkoxy," as used herein, refers to a moiety having the structure —O-alkyl, in which the alkyl moiety is described above.

The term "aryl" as used herein includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. The aromatic ring can be substituted at one or more ring positions with such moieties, e.g., as described above for alkyl groups. Preferred aryl groups include unsubstituted and substituted phenyl groups.

The term "aryloxy," as used herein, refers to a group having the structure —O-aryl, in which the aryl moiety is as defined above.

The term "amino," as used herein, refers to an unsubstituted or substituted moiety of the formula —$NR_aR_b$, in which $R_a$ and $R_b$ are each independently hydrogen, alkyl, aryl, or heterocyclyl, or $R_a$ and $R_b$, taken together with the nitrogen atom to which they are attached, form a cyclic moiety having from 3 to 8 atoms in the ring. Thus, the term "amino" is intended to include cyclic amino moieties such as piperidinyl or pyrrolidinyl groups, unless otherwise stated. An "amino-substituted amino group" refers to an amino group in which at least one of $R_a$ and $R_b$, is further substituted with an amino group.

As used herein, the term "subject" or "patient" is intended to include living organisms in which certain conditions as described herein can occur or which are at a high-risk for the occurrence of such conditions. Examples include humans, monkeys, cows, sheep, goats, dogs, cats, mice, rats, and transgenic species thereof. In a preferred embodiment, the subject or patient is a primate. In an even more preferred embodiment, the primate is a human. A subject or patient can be a human suffering from or at a high-risk of developing a cancer, an inflammatory disease or a neurodegenerative disease. Other examples of subjects include experimental animals such as mice, rats, dogs, cats, goats, sheep, pigs, and cows. The experimental animal can be an animal model for a disorder, e.g., a transgenic mouse with an Alzheimer's-type neuropathology. As used herein, the term "pharmaceutically acceptable salt" refers to a composition in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

As used herein, the term "$IC_{50}$" refers to an inhibitory dose which is 50% of the maximum response obtained.

As used herein, the term "water soluble" means that the compound dissolves in water at least to the extent of 0.010 mole/liter or is classified as soluble according to literature precedence.

As used herein, predominantly one enantiomer means that the compound contains at least 95% of one enantiomer, or more preferably at least 98% of one enantiomer, or most preferably at least 99% of one enantiomer. For example, a compound may contain 99% (+) TBE-5 and 1% (−) TBE-5.

As used herein the specification, "a" or "an" may mean one or more. As used herein in the claim(s), when used in conjunction with the word "comprising," the words "a" or "an" may mean one or more than one. As used herein "another" may mean at least a second or more.

Other abbreviations used herein are as follows: DMSO, dimethyl sulfoxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFN-γ, interferon-γ; LPS, bacterial endotoxic lipopolysaccharide; TNF-α, tumor necrosis factor-α; IL-1β, interleukin-1β; GAPDH, glyceraldehyde-3-phosphate dehydrogenase; MTT, 3-[4,5-dimethylthiazol-2-yl]-2,5-diphenyltetrazolium bromide; TCA, trichloroacetic acid.

III. Synthesis of TBEs

Although triterpenoids are widely used for medicinal purposes in many Asian countries, this class of molecules has not had an impact on the practice of Western medicine. Triterpenoids are formed in nature by the cyclization of squalene with the retention of all 30 carbon atoms in molecules such as oleanolic acid (OA) and ursolic acid (UA). Although OA and UA are known to have numerous pharmacological activities, including chemoprevention of cancer and anti-inflammatory activity in experimental animals, the potency of these naturally occurring molecules is relatively weak. Chemical synthesis of new steroid analogs has provided many useful derivatives that are more potent and specific than the natural parent structures. With this as a model, and considering the known anti-inflammatory and anticarcinogenic activities of OA and UA (Huang et al., 1994; Nishino et al., 1988; Hirota et al., 1990; Singh et al., 1992), the present inventors have synthesized and characterized a series of synthetic triterpenoid analogs as potential inhibitors of inflammation and carcinogenesis, using inhibition of NO production induced by interferon-γ in mouse macrophages (iNOS assay) as a preliminary screening assay system (Ding et al., 1990; Bogdan et al., 1992).

TBEs can be synthesized from cheap commercially available reagents. TBEs with various functionalities at various positions can be designed rationally as shown in the Examples. Water-soluble TBEs can be designed and synthesized as described in Example 6, since the hydrophobic part of TBEs is smaller than that of triterpenoids. The use of water-soluble compounds would reduce undesirable pharmacokinetics, limitations of administration methods, and considerable difficulty in developing formulations for clinical use. Efficient methods of synthesis of TBE's utilizing novel intermediates 1, 2a, 2b and 2c are also provided in Examples 2 & 3.

IV. TBE Administration

The compounds of the present invention may be administered by a variety of methods, e.g., orally or by injection (e.g. subcutaneous, intravenous, intraperitoneal, etc.). Depending on the route of administration, the active compound may be coated in a material to protect the compound from the action of acids and other natural conditions which may inactivate the compound. In the case of cancer therapy, the agents may be administered intra-tumorally, circumferential to a tumor mass, locally to the tumor vasculature or lypmphatic system, regionally or systemically. They may also be administered to a resected tumor bed, for example, by syringing or by a post-operative catheter with continuous perfusion/infusion.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

Active compounds are administered at a therapeutically effective dosage sufficient to treat a condition associated with a condition in a patient. A "therapeutically effective amount" preferably reduces the amount of symptoms of the condition in the infected patient by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems shown in the examples and drawings.

V. TBE Uses and Mechanisms

The TBE compounds of the present invention have utility for prevention and treatment of cancer, Alzheimer's disease, Parkinson's disease, multiple sclerosis, amyotrophic lateral sclerosis, rheumatoid arthritis, inflammatory bowel disease, and all other diseases whose pathogenesis is believed to involve excessive production of either nitric oxide or prostaglandins.

In particular, the present invention may be applied to therapy of such cancers as breast, prostate, lung (SCLC and NSCLC), brain, head & neck, esophagus, trachea, stomach, colon, rectum, uterus, cervix, prostate, liver, pancreas, skin, blood and lymphatic system, testes and ovary.

The aberrant or excessive expression of either iNOS or COX-2 has been implicated in the pathogenesis of many disease processes, including carcinogenesis in the colon. Thus, overexpression of the gene for COX-2 is an early and central event in colon carcinogenesis (Prescott and White, 1996; Dubois et al., 1996). Mice with defects in the APC (adenomatous polyposis coli) gene develop large numbers of intestinal polyps at an early age, and marked elevations in COX-2 enzyme levels have been found in these polyps. These animal findings correlate with the finding of elevated levels of COX-2 mRNA and protein in many human primary colon cancers and colon cancer cell lines (Prescott and White, 1996), and it is believed that this elevation in COX-2 leads to a suppression of apoptosis, which would ordinarily lead to death of preneoplastic cells (Tsujii and DuBois, 1996).

The functional relevance of COX-2 to intestinal tumorigenesis has been demonstrated by knockout of the COX-2 gene and the subsequent mating of mice bearing this knockout with polyp-forming mice bearing lesions in the APC gene; the COX-2 knockout caused a dramatic diminution in the number of polyps in the offspring (Oshima et al., 1996). Furthermore, treatment of experimental animals with either selective COX-2 inhibitors or non-selective COX-1/COX-2 inhibitors has been reported to be a potent approach to chemoprevention of intestinal cancer (Marnett, 1992; Oshima et al., 1996; Boolbol et al., 1996; Reddy et al., 1996; Sheng et al., 1997). As for the role of iNOS in carcinogenesis, it is clear that NO is a potent mutagen (Tamir and Tannebaum, 1996), and that nitric oxide can also activate COX-2 (Salvemini et al., 1993; 1994). Furthermore, there is a marked increase in iNOS in rat colon tumors induced by the carcinogen, azoxymethane (Takahashi et al., 1997).

Numerous studies by others have suggested an important role of NF-κB in regulating genes involved in apoptosis, proliferation, and metastasis (Baeuerle et al., 1996; Baldwin, 1996; Bargou et al., 1997; Barnes et al., 1997; Ghosh et al., 1998; Barkett et al., 1999; Pahl et al., 1999; Rayet et al., 1999; Huang et al., 2000). Aberrant expression of genes of the NF-κB complex has been found in many human tumors. Most recently it has been suggested that NF-κB activity may lead to enhancement of the cell cycle by its ability to activate cyclin D1 (Guttridge et al., 1999; Hinz et al., 1999; Joyce et al., 1999).

Multiple sclerosis (MS) is known to be an inflammatory condition of the central nervous system (Williams, Ulvestad and Hickey, 1994; Merrill and Beneviste, 1996; Genain and Hauser, 1997). Inflammatory, oxidative, or immune mechanisms may be involved in the pathogenesis of Alzheimer's disease (AD), Parkinson's disease (PD), amyotropic lateral sclerosis (ALS), and MS (Bagasra et al., 1995; McGeer and McGeer, 1995; Simonian and Coyle, 1996; Kaltschmidt et al., 1997). Both reactive astrocytes and activated microglia have been implicated in causation of NDD/NID. There has been a particular emphasis on microglia as cells that synthesize both NO and prostaglandins as products of the respective enzymes, iNOS and COX-2. De novo formation of these enzymes may be driven by inflammatory cytokines such as interferon-γ or interleukin-1. In turn, excessive production of NO may lead to inflammatory cascades and/or oxidative damage in cells and tissues of many organs, including neurons and oligodendrocytes of the nervous system, with consequent manifestations in AD and MS, and possible PD and ALS (Coyle and Puttfarcken, 1993; Goodwin et al., 1995; Beal, 1996; Merrill and Benvenist, 1996; Simonian and Coyle, 1996; Vodovotz et al., 1996). Epidemiologic data indicate that chronic use of NSAID's which block synthesis of prostaglandins from arachidonate, markedly lower the risk for development of AD (McGeer et al., 1996; Stewart et al., 1997). Thus, agents that block formation of NO and prostaglandins, may be used in approaches to prevention and treatment of NDD.

Further disclosed herein are the synthesis and biological activities of new TBE compounds that have important properties including (1) the ability to induce and differentiate both malignant and non-malignant cells; (2) activity at sub-micromolar or nanomolar levels as an inhibitor of proliferation of many malignant or premalignant inhibitors of proliferation of many malignant or premalignant cells; (3) significantly greater activity than most compounds in suppressing the de novo synthesis of the inflammatory enzymes, iNOS and COX-2; (4) water solubility; and (5) cheap production. TBEs also are important for the development of new chemopreventative agents, as well as relevant to therapy of malignancy itself.

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, Sambrook, J. et al. (1989; Ausubel et al. 1995; Glover, 1985; Gait, 1984; U.S. Pat. No. 4,683,195; Hames and Higgins, 1984; the treatise, Mayer and Walker, 1987; Weir and Blackwell, 1986; Miller, 1972, the entire contents of which are incorporated herein by reference).

VI. Combination Therapies

In addition to being used as a monotherapy, the TBE's of the present invention will also find use in combination therapies. Such combination therapies may include the use of any other inhibitor(s) of COX-2 and/or iNOS, other anti-inflammatory agent(s) one or more anti-cancer therapies, or one or more drugs used to treat or prevent a neurodegenerative condition as discussed in detail below. Such medications and therapies are also well known to one of skill in the art.

An "anti-cancer" agent is capable of negatively affecting cancer in a patient, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the TBE and the other agent(s) at the same time. This may be achieved by contacting the cell with a single composition or pharmacological formulation that includes both agents, or by contacting the cell with two distinct compositions or formulations, at the same time, wherein one composition includes the TBE and the other includes the second agent(s).

Alternatively, the TBE therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and the TBE would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, TBE therapy is "A" and the secondary agent, such as an anti-inflammatory agent, an anti-cancer agent, or an agent used to treat a neurodegenerative condition, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Other combinations are also contemplated.

Administration of the TBE compounds of the present invention to a patient will follow general protocols for the administration of chemotherapeutics, taking into account the toxicity, if any, of the drug. It is expected that the treatment cycles would be repeated as necessary. It also is contemplated that various standard therapies, as well as surgical intervention, may be applied in combination with the described hyperproliferative cell therapies.

VII. Adjunct Cancer Therapies

In the case of cancer treatment with the TBE agents of the present invention, it is contemplated that other cancer therapies used in the art will be used in combination with the TBE compounds. Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that TBE therapy could be used similarly in conjunction with chemotherapeutic, radiotherapeutic, or immunotherapeutic intervention, in addition to other pro-apoptotic or cell cycle regulating agents, as discussed below.

a. Chemotherapy

Chemotherapies include the used of agents such as cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with TBE therapy. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

d. Gene Therapy

In yet another embodiment, the secondary treatment is a secondary gene therapy in which a therapeutic polynucleotide is administered before, after, or at the same time a TBE. Therapeutic genes may include an antisense version of an inducer of cellular proliferation (sometimes called an oncogene), an inhibitor of cellular proliferation (sometimes called a tumor suppressor), or an inducer of programmed cell death (sometimes called a pro-apoptotic gene).

e. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

f. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

VIII. Adjunct Therapies for Inflammatory Diseases and Neurodegenerative Conditions The TBE compounds and pharmaceutical formulations of the invention will also be sued in conjunction with agents used in the art to treat inflammatory and degenerative conditions that involve excessive NO and/or prostaglandins.

a. Anti-Inflammatory Agents

It is contemplated that other anti-inflammatory agents will be used in conjunction with the TBE derivatives of the current invention. Other COX inhibitors may be used, including arylcarboxylic acids (salicylic acid, acetylsalicylic acid, diflunisal, choline magnesium trisalicylate, salicylate, benorylate, flufenamic acid, mefenamic acid, meclofenamic acid and triflumic acid), arylalkanoic acids (diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin and sulindac) and enolic acids (phenylbutazone, oxyphenbutazone, azapropazone, feprazone, piroxicam, and isoxicam. (U.S. Pat. No. 6,025, 395)

Histamine H2 receptor blocking agents may also be used in conjunction with the TBE derivatives of the current invention, including cimetidine, ranitidine, famotidine and nizatidine.

b. Anti-Cholinesterase Inhibitors

Treatment with acetylcholinesterase inhibitors such as tacrine, donepizil, metrifonate and rivastigmine for the treatment of Alzheimers and other disease in conjunction with the TBE derivatives of the present invention is contemplated. Other acetylcholinesterase inhibitors may be developed which may be used once approved include rivastigmine and metrifonate. Acetylcholinesterase inhibitors increase the amount of neurotransmitter acetylcholine at the nerve terminal by decreasing its breakdown by the enzyme cholinesterase.

c. Estrogen Replacement Therapy

Estrogen replacement therapy (ERT) can be used in conjunction with the TBE derivatives of the current invention for the treatment of Alzheimer's and other diseases. Estrogen is an excellent neuroprotective agent and effects multiple pathways that are involved in the pathogenisis of diseases that also involve excessive production of either nitric oxide (NO) or prostaglandins.

d. MAO-B Inhibitors

MAO-B Inhibitors such as selegilene (Eldepryl or Deprenyl) may be used in conjunction with the TBE derivatives of the current invention. Selegilene is used for Parkinson's disease and irreversibly inhibits monoamine oxidase type B (MAO-B). Monoamine oxidase is an enzyme that inactivates the monoamine neurotransmitters norepinephrine, serotonin and dopamine.

e. Pharmaceutical Agents for MS

Common drugs for multiple sclerosis (MS) that can be used in combination with the triterpeonoid derivatives include immunosuppressive drugs such as azathioprine (Imuran), cladribine (Leustatin), and Clyclophosphamide (Cytoxan).

f. Supplements

Dietary and nutritional supplements with reported benefits for treatment or prevention of Parkinson's, Alzheimer's, multiple sclerosis, amyotropic lateral sclerosis, rheumatoid arthritis, inflammatory bowel disease, and all other diseases whose pathogenesis is believed to involve excessive production of either nitric oxide (NO) or prostaglandins, such as acetyl-L-carnitine, octacosanol, evening primrose oil, vitamin B6, tyrosine, phenylalanine, vitamin C, L-DOPA, or a combination of several antioxidants may be used in conjunction with the TBE derivatives of the current invention.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of TBE Compounds a. Synthesis of Racemic TBE-3-5

The inventors' initial targets were the simple structures, TBE-3-5. Racemic TBE-3-5 were prepared in several steps via known compounds 4 (Dutcher et al., 1976), 5 (Honda et al., 1981), and 6 (Hirota et al., 1988) from 1-chloro-3-pentanone (1) [or ethyl vinyl ketone (2)] and 2-methyl-1,3-cyclohexanedione (3) according to the synthetic route shown in Scheme 1.

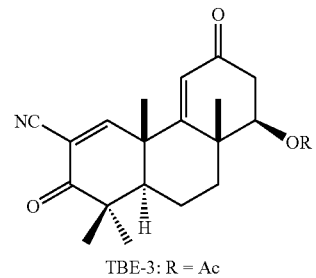

TBE-3: R = Ac
TBE-4: R = H

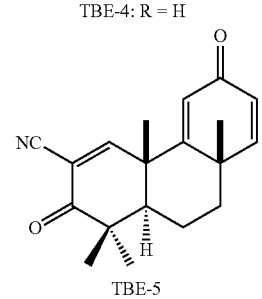

TBE-5

(±)-Bicyclic enone 4 was synthesized by Robinson annulation of 2-methyl-1,3-cyclohexanedione (3) with 1-chloro-3-pentanone (1) [or ethyl vinyl ketone (2)], followed by selective reduction with sodium borohydride (57% yield). Tricyclic enone 5 was obtained in 43% yield by Robinson annulation of 4 with ethyl vinyl ketone (2). Reductive methylation of 5 with methyl iodide in the presence of lithium in liquid ammonia gave 6 in 71% yield. Hydroxymethylene 7 was prepared in 92% yield from 6 with ethyl formate in the presence of sodium methoxide in benzene (Clinton et al., 1961). Isoxazole 8 was prepared in 73% yield by condensation of 7 and hydroxylamine hydrochloride in water and ethanol (Johnson et al., 1945). Cleavage of the isoxazole moiety of 8 with sodium methoxide gave nitrile 9 quantitatively. TBE-1 was prepared quantitatively by 2,3-dichloro-5,6-dicyano-1,4-benzoquinone (DDQ) oxidation of 9. Acetylation of TBE-1 gave TBE-2 in 97% yield. Initially, allylic oxidation of TBE-2 with chromium trioxide and pyridine complex in methylene chloride did not give the desired compound, TBE-3. After various oxidizing agents were surveyed, the inventors found that a catalytic amount of chromium trioxide and t-butyl hydroperoxide in methylene chloride (Muzart, 1987) afforded TBE-3 and epoxide 10 in 47% and 29% yield, respectively. Alkaline hydrolysis of TBE-3 gave TBE-4 and 5 in 50% and 46% yield, respectively.

TBE-3-5 show significant inhibitory activity ($IC_{50}$=0.01 μM level) on NO production induced by IFN-γ in mouse macrophages (see Table 1). The potency of TBE-3-5 is similar to that of hydrocortisone although they do not act through the glucocorticoid receptor (data not shown). TBE-3-5 were more potent than TBE-1 and 2. This result suggests that the bis-enone structure is very important for high potency in even relatively simple molecules.

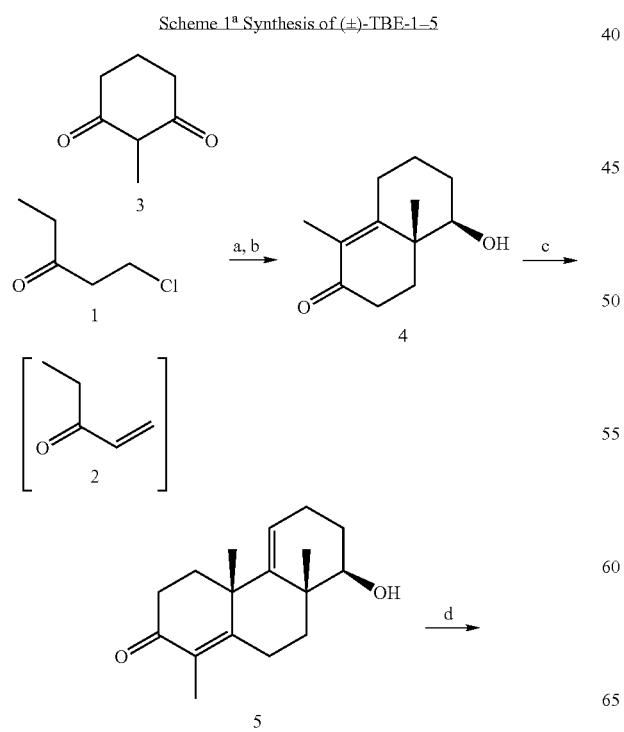

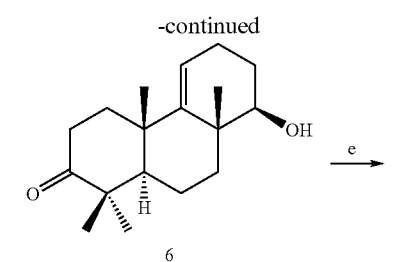

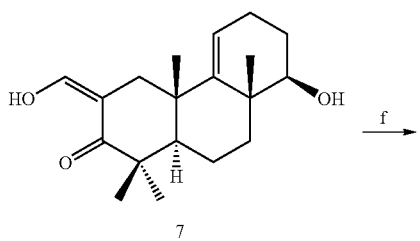

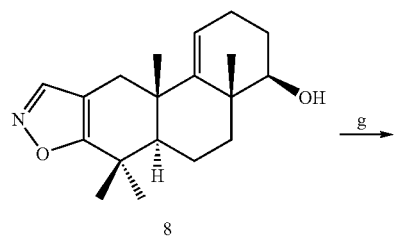

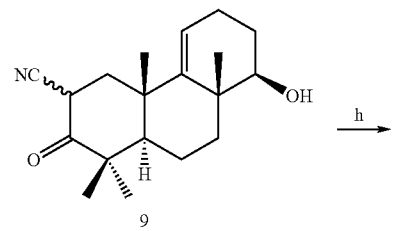

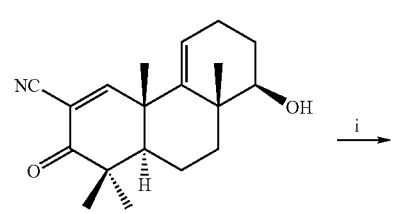

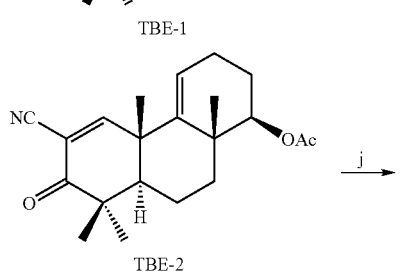

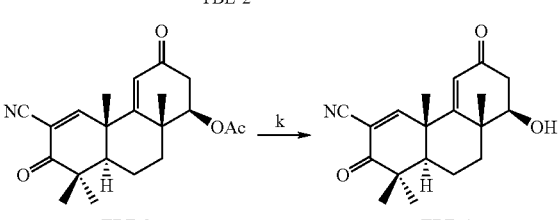

-continued

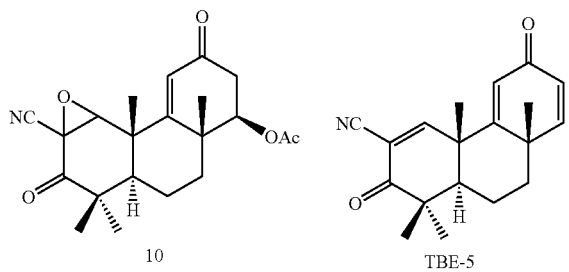

aReagents: (a) p-TsOH, PhH for 1; KOH, MeOH, pyrrolidine, PhH for 2; (b) NaBH$_4$, EtOH; (c) EVK (2), Na, MeOH; (d) Li, CH$_3$I, liq. NH$_3$; (e) HCO$_2$Et, NaOMe, PhH; (f) NH$_2$OH•HCl, aq EtOH; (g) NaOMe, Et$_2$O, MeOH; (h) DDQ, PhH; (i) Ac$_2$O, pyr.; (j) CrO$_3$, t-BuOOH, CH$_2$Cl$_2$; (k) KOH, aq MeOH b. Synthesis of Optically Pure (−)-TBE-5 with the Same Configuration of Naturally Occurring Triterpenoids and its Antipode, (+)-TBE-5

In many cases, one enantiomer has much more potency than the antipode. Therefore, one enantiomer of TBE-5 was expected to show more potency than racemic TBE-5. Moreover, it has become very important to create optically pure drugs rather than racemic ones to avoid undesired side effects that might be caused by the antipode. For both reasons, the inventors have synthesized optically pure (−)-TBE-5 with the same configuration of naturally occurring triterpenoids and its antipode, (+)-TBE-5. (Development of TBE-3 and 4 was excluded because they are expected to be unstable due to their β-hydroxy-ketone structures.)

Optically pure (4aS)-(+)- and (4aR)-(−)-1,4a-dimethyl-4,4a,7,8-tetrahydro-naphthalene-2,5(3H,6H)-dione [(+)- and (−)-12] were prepared via achiral intermediate 11 from ethyl vinyl ketone (2) and 2-methyl-1,3-cyclohexanedione (3) by a known method (Hagiwara et al., 1988). Enantiomer (+)-6 with the same configuration as naturally occurring triterpenoids and its antipode (−)-6 were synthesized from (−)- and (+)-12, respectively (Scheme 2) according to the same sequence as for racemic 6. The enantiomeric excess of each enantiomer was determined to be 90% by $^1$H and $^{19}$F NMR of the (−)-R-MTPA ester (Dale et al., 1969) derived from each enantiomer.

Scheme 2a

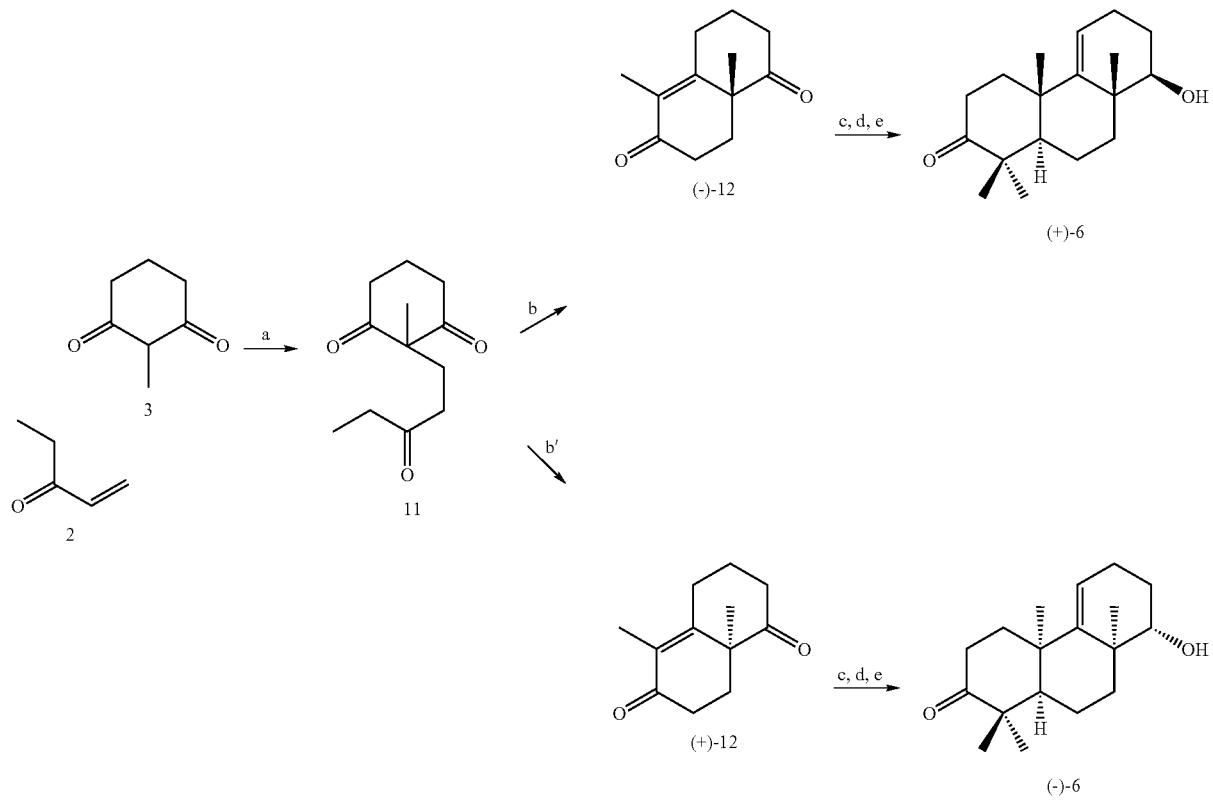

Both enantiomers of TBE-5 were synthesized from (+)- and (−)-6 according to the alternative route shown in Scheme 3. Acetylation of (+)-6 gave (+)-13 in quantitative yield. Allylic oxidation of (+)-13 gave (+)-14 in 79% yield. Deacetylation of (+)-14 with DBU gave (−)-15 in 97% yield (Srikrishna et al., 1998). Cyanation of the enolate of (−)-15 with p-TsCN in THF gave (−)-16 in 93% yield (Kahne et al., 1981). DDQ oxidation of (−)-16 gave (−)-TBE-5 ([α]$_D$ −115°, CHCl$_3$) in 73% yield. Overall yield of (−)-TBE-5 from (+)-6 was 52%. Because, in the former route (Scheme 1), the overall yield of TBE-5 from 6 was only 14%, the yield was much improved by this route. (+)-TBE-5 ([α]$_D$ +115°, CHCl$_3$) was also synthesized by this sequence.

Scheme 3$^a$

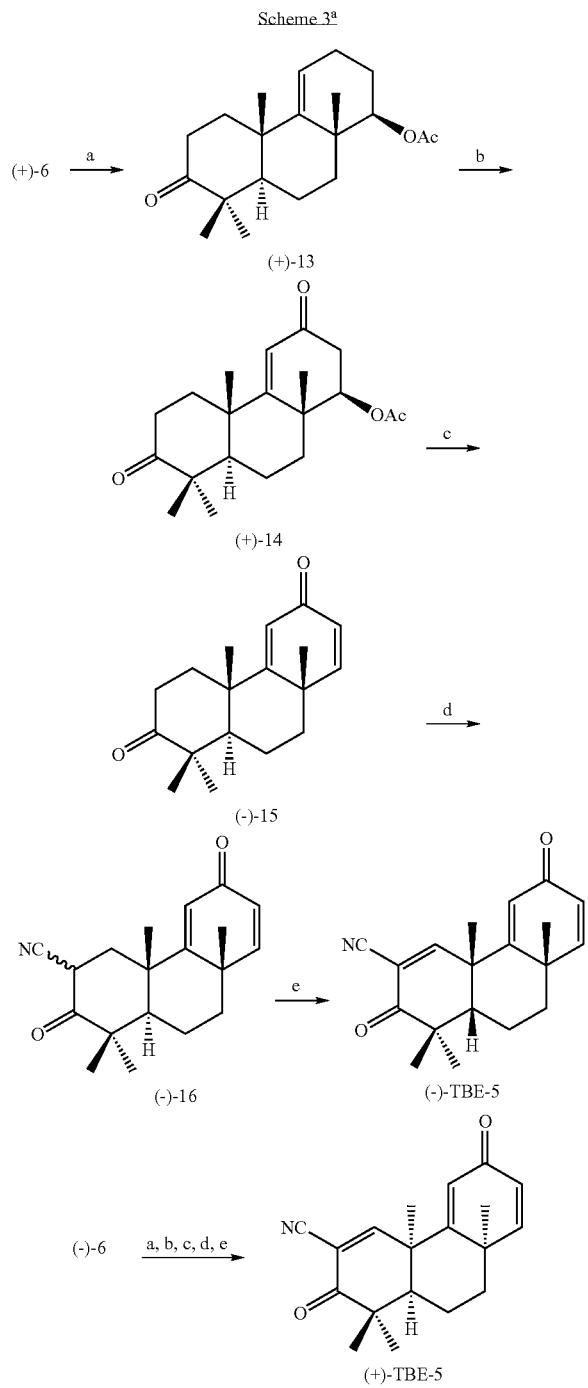

Surprisingly, both enantiomers (−)- and (+)-TBE-5 show the same potency in iNOS assay (see Table 1). They also showed the same inhibitory activity against several cancer cell lines (data not shown). These results cannot be explained by racemization of both enantiomers in the living cells because it is chemically impossible for them to racemize. One possibility is that TBE-5 does not have enough potency for the comparison of both enantiomers.

c. Synthesis of Racemic TBE-6-9, TBE-5 Analogs with Electron-Withdrawing Groups at C-13

As TBE-5 shows good potency (0.01 μM level, similar in potency to hydrocortisone), the inventors contemplated that TBE-5 is a good scaffold from which to discover new, more potent TBE compounds. Thus, the inventors initially designed TBE-5 analogs having general formula I to discern the influence of substituents at C-13 on potency. Among them, TBE-6-9 and TBE-5 analogs with electron-withdrawing groups at C-13 have been synthesized according to the synthetic route shown in Scheme 4.

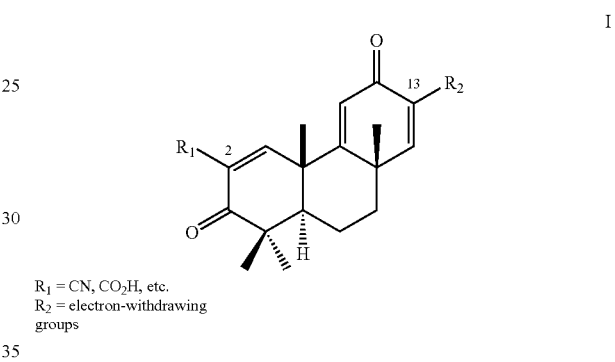

$R_1$ = CN, CO$_2$H, etc.
$R_2$ = electron-withdrawing groups

Ketal 17 was synthesized in 93% yield by ketalization of 6, followed by oxidation. Ester 18 (a mixture of two epimers) was prepared in 71% yield from 17 by methylation with Stiles' reagent (Finkbeiner et al., 1963) and subsequent methylation, followed by reduction with NaBH$_4$. Deketalization of 18, subsequent mesylation of the hydroxyl group at C-14, followed by dehydration with DBU gave 19 in 74% yield (Hirota et al., 1991). Isoxazole 20 was obtained in 97% yield by formylation at C-2 of 19, followed by condensation with hydroxylamine. Allylic oxidation of 20 gave dienone 21 in 58% yield. TBE-6 was obtained in 81% yield by cleavage of the isoxazole moiety of 21 with basic conditions, followed by DDQ oxidation. TBE-6 was synthesized in 13 steps (overall yield, 22%; average yield, 89% per step) from 6. Hydrolysis of TBE-6 with basic conditions gave TBE-7 in 77% yield. Amidation of TBE-6 with saturated ammonia in methanol gave TBE-8 in 64% yield. Dehydration of TBE-8 with thionyl chloride in toluene gave TBE-9 in 40% yield.

Scheme 4$^a$

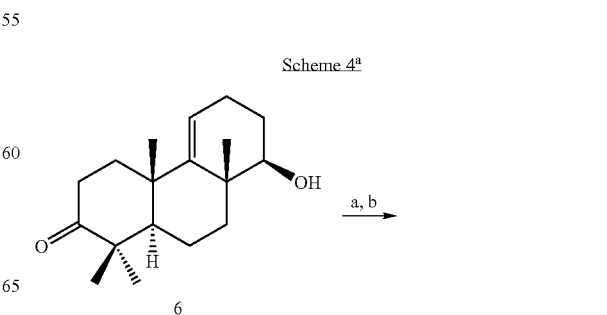

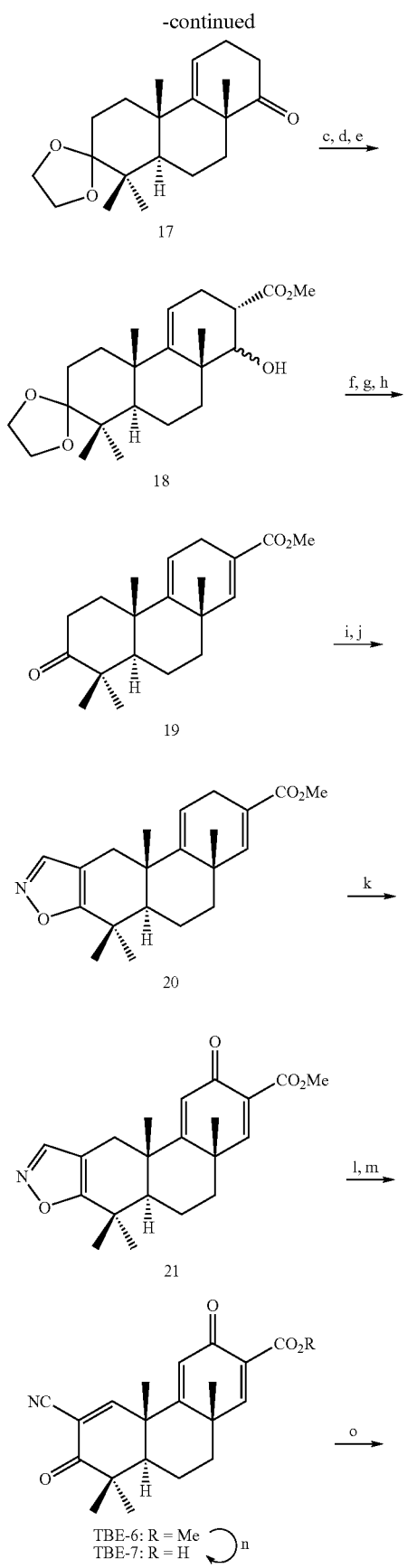

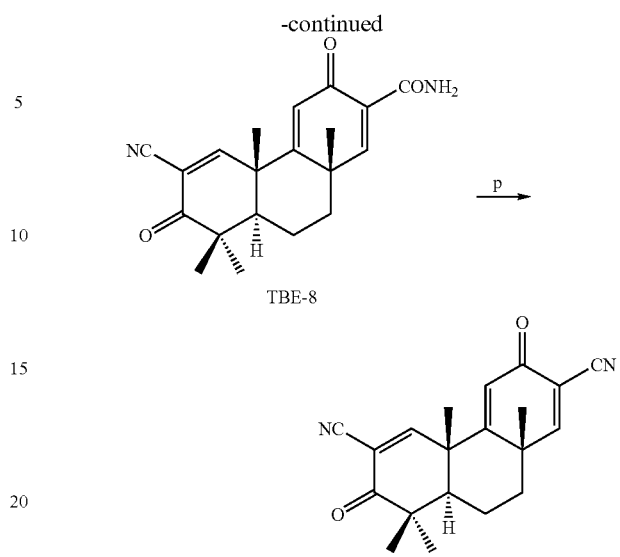

aReagents: (a) HOCH2CH2OH, PPTS, PhH; (b) CrO3 (6 equiv.), pyr. CH2Cl2; (c) MMC, DMF; (d) CH2N2, Et2O, THF; (e) NaBH4, EtOH, CH2Cl2; (f) PPTS, acetone, H2O; (g) MsCl, pyr, CH2Cl2; (h) DBU, THF; (i) HCO2Me, NaOMe, PhH; (j) NH2OH·HCl, H2O, EtOH; (k) CrO3 (21 equiv.), pyr., CH2Cl2; (l) NaOMe, Et2O, MeOH; (m) DDQ, PhH; (n) KOH, H2O, MeOH; (o) NH3, MeOH; (p) SOCl2, toluene.

The inventors found that TBE-9 attains the initial target potency (IC$_{50}$, 1 NM level) in the iNOS assay (Table 1). TBE-9 is about 5 and 30 times more potent than hydrocortisone and TBE-5, respectively. Further testing of TBE-9 indicates that the compound is orally active at 15 and 30 mg/kg in in vivo studies using mouse peritoneal inflammation induced by thioglycollate and IFN-gamma and shows no signs of toxicity at either dose (FIG. 5). These test also revealed that TBE-9 is much more potent than hydrocortisone.

d. Synthesis of Racemic TBE-10, Simpler Structure without the Double-Bond at C-13

It is important to examine whether or not a double-bond at C-13 is necessary for the biological potency because an additional Michael acceptor (13-en-12-one) might cause toxicity. Thus, racemic TBE-10 has been synthesized from 6 according to the synthetic route shown in Scheme 5. The inventors adopted a radical deoxygenation to remove the hydroxyl group at C-13 of 6 (Rasmussen et al., 1981). N,N-Thiocarbonyldiimidazole (TCDI) gave 22 in 75% yield. Tributyltin hydride gave new tricyclic ketone 23 in 88% yield. Isoxazole 24 was prepared in 2 steps (59% yield) from 23. Allylic oxidation of 24 gave 25 in 62% yield. TBE-10 was obtained in 66% yield by cleavage of the isoxazole with sodium methoxide, followed by DDQ oxidation.

Scheme 5a

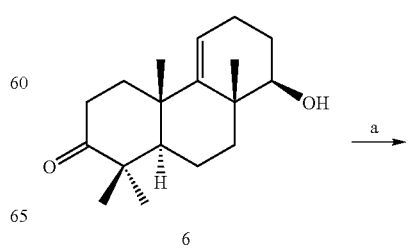

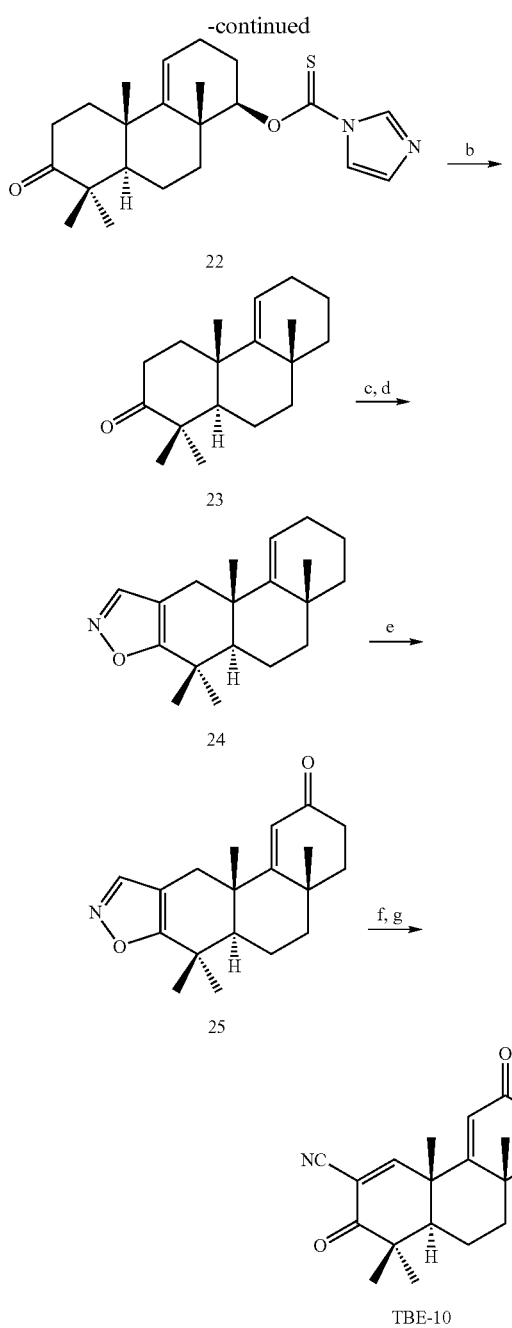

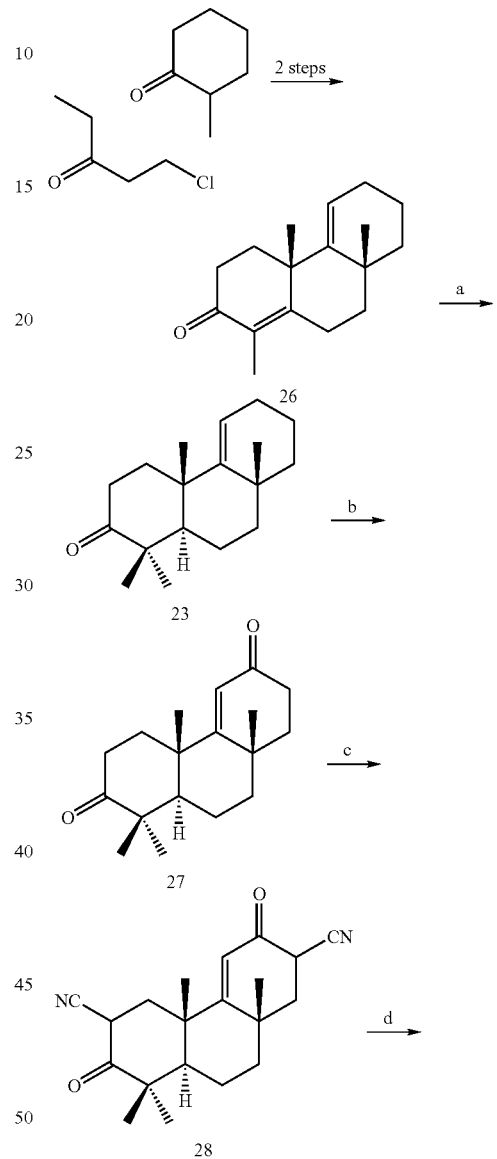

[a]Reagents: (a) TCDI, THF; (b) (n-Bu)₃SnH, toluene; (c) HCO₂Et, NaOMe, PhH; (d) NH₂OH·HCl, aq EtOH; (e) t-BuOOH, CrO₃, CH₂Cl₂; (f) NaOMe, Et₂O, MeOH; (g) DDQ, PhH Interestingly, TBE-10 is about 3 times more potent than TBE-5. This result is very important because it suggests that the 13-en-12-one functionality is not always necessary for potency.

e. Efficient Alternative Synthesis of TBE-9

Because generally, in in vitro assays using cells, a potency at the 1 nM level is enough to examine in vivo activity, the initial target potency for the TBE compounds was the 1 nM level. In order to test TBE-9 in in vivo assays it is necessary to synthesize more than 1 g of TBE-9. TBE-9 was synthesized in 19 steps from commercially available simple compounds by the synthetic route shown in Scheme 4. Unfortunately, this route is not suitable for the practical synthesis of TBE-9.

Thus, a new efficient synthesis of TBE-9 was investigated. Eventually, the inventors succeeded in preparing TBE-9 in 6 steps from commercially available simple compounds (Scheme 6). This route is 13 steps less than the former route. This success indicates that the inventors could supply a large amount of useful TBE compounds at low cost.

[a]Reagents: (a) Li (4.5 eq.), H₂O (1 eq.), liq. NH₃, THF, CH₃I; (b) t-BuOOH, CrO₃, CH₂Cl₂; (c) p-TsCN (4 eq.), LDA (2.4 eq.), THF; (d) DDQ (2.5 eq.), PhH The improvement on the reductive methylation incorporating 1 equivalent of water gave 23 in 63% yield from 26, a known compound which is easily synthesized in 2 steps and good yield from 2-methylcyclohexanone and 1-chloro-3-pentanone (Heathcock et al., 1984), although the conventional reductive methylation procedure with 26 did not give 23 at all. Allylic oxidation of 23 gave 27 in 64% yield. Double cyanation of the enolate of 27 with p-TsCN in THF successfully gave dinitrile 28 (a mixture of at least three isomers). TBE-9 was prepared in 67% yield (from 27) by DDQ oxidation.

Establishment of a synthetic method to convert 26 to 23 is pivotal because the inventors can shorten the synthetic paths of various analogs using 23 instead of 6 as a starting material. For example, TBE-10 can be synthesized in 8 steps via 23, although 11 steps were necessary when TBE-10 was prepared as shown in Scheme 5.

Example 2
Novel Tricyclic Intermediates and Methods for Synthesis

The inventors have also synthesized new tricyclic compounds 23 and 29a, 29b, and 29c, which are useful and important intermediates for the synthesis of various TBE compounds having general formula II and the following example describes efficient methods for their preparation.

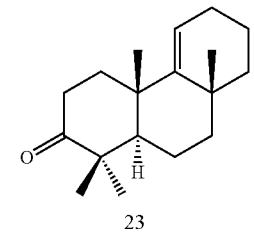

23

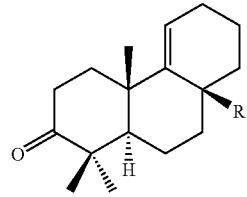

29a: R = CO$_2$H
29b: R = CO$_2$Me
29c: R = CH$_2$OH

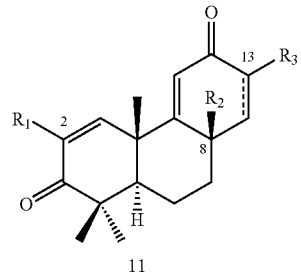

11

R$_1$ = CN, CO$_2$H, etc.
R$_2$ = CH$_3$, CO$_2$R$_3$, CONHR$_3$, CHO, CN, CH$_2$NHR$_4$, CH$_2$OR$_4$, CH$_2$X (X = F, Cl, Br), etc.
R$_3$ = H, CN, CH$_2$NR$_6$R$_7$ (CH$_2$)$_n$CO$_2$R$_4$ etc.

New tricyclic compounds 23 and 29a-29c are very useful and important intermediates for the synthesis of various TBE compounds in a few steps at low cost. For example, the synthesis of TBE-9 requires 9 steps via known compound 6 from commercially available 1-chloro-3-pentanone and 2-methyl-1,3-cyclohexadione. However, TBE-9 can be synthesized in only six steps via new compound 23 from commercially available 1-chloro-3-pentanone and 2-methylcyclohexanone (Scheme 7). Also, TBE-12 can be synthesized in a few steps via new compound 29b from commercially available 1-chloro-3-pentanone and 2-carbomethoxycyclohexanone (Scheme 8). In addition to the synthesis of TBE-9 and 12, various other TBE compounds can be synthesized from intermediates 23 and 29a-29c (see EXAMPLES 4 and 6).

Scheme 7.$^a$ Synthesis of TBE-9 Using the Intermediates

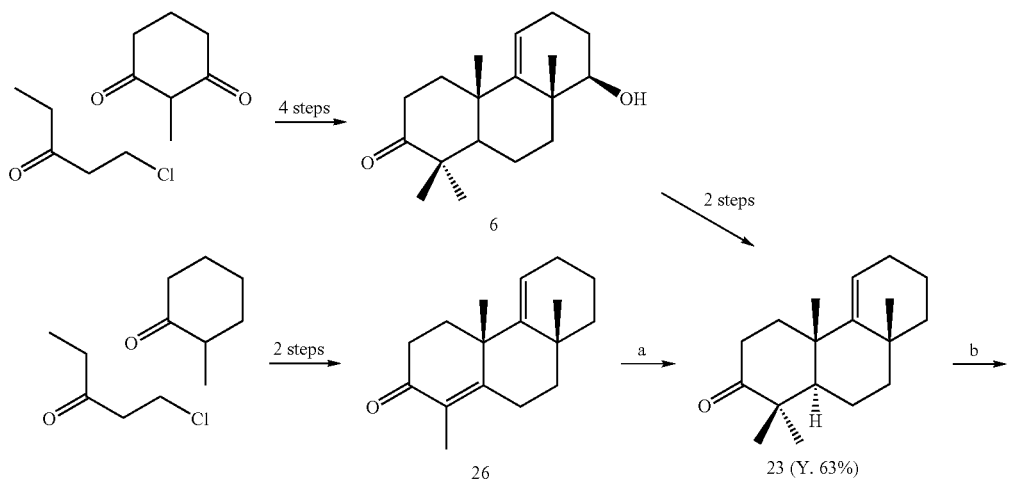

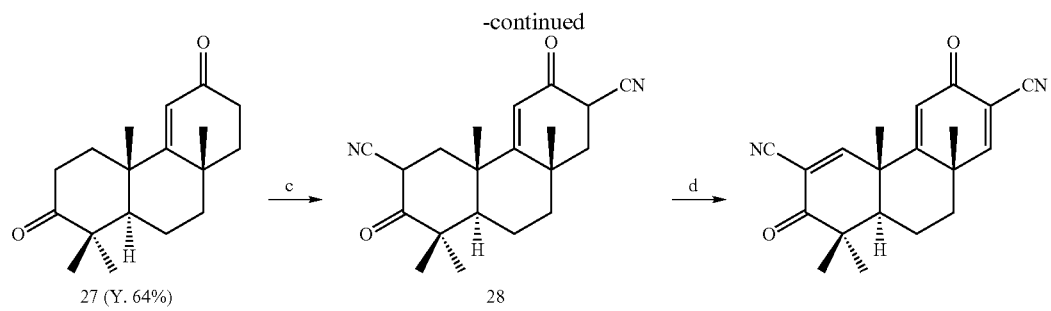

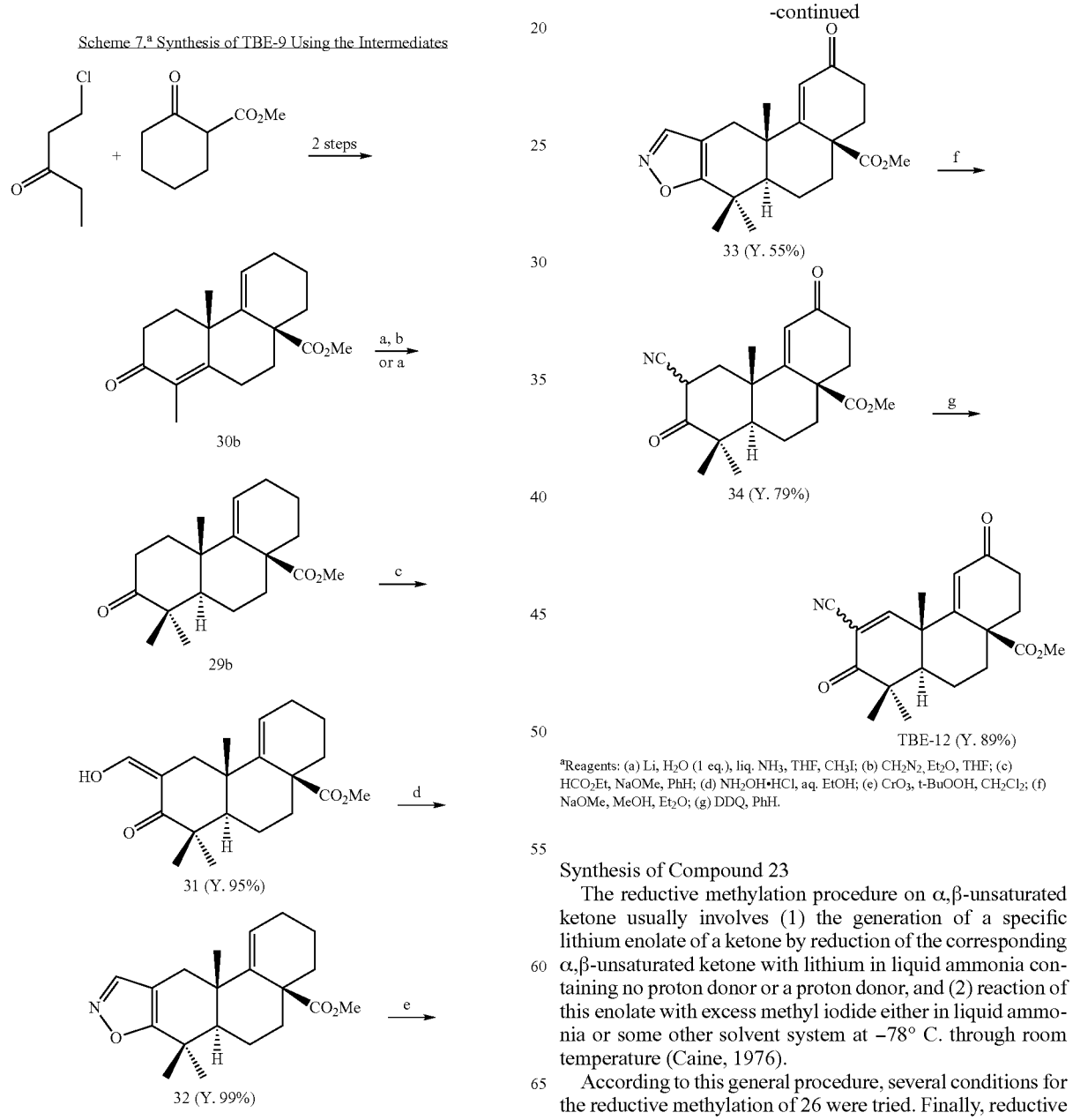

Synthesis of Compound 23

The reductive methylation procedure on α,β-unsaturated ketone usually involves (1) the generation of a specific lithium enolate of a ketone by reduction of the corresponding α,β-unsaturated ketone with lithium in liquid ammonia containing no proton donor or a proton donor, and (2) reaction of this enolate with excess methyl iodide either in liquid ammonia or some other solvent system at −78° C. through room temperature (Caine, 1976).

According to this general procedure, several conditions for the reductive methylation of 26 were tried. Finally, reductive methylation of 26 using 4.5 equivalents of lithium and one equivalent of water and quenching the excess lithium with isoprene, followed by the addition of methyl iodide at 0° C. (see the detailed procedure in the EXAMPLE 3) gave the new compound 23 in 63% yield (Scheme 9).

Scheme 9.ª Synthesis of Compound 23

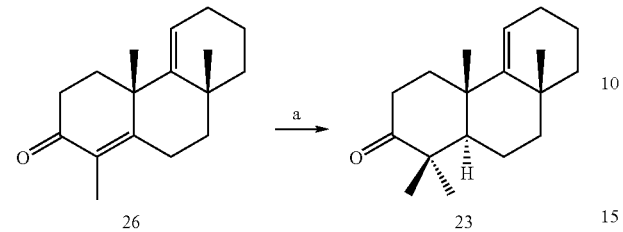

ªReagents: (a) Li (4.5 eq.), H₂O (1 eq.), liq. NH₃, THF, CH₃I.

Interestingly, the reductive methylation of 26 without a proton donor or with proton donors other than water does not give 23. For example, an attempt with about 3.3 equivalents of lithium in liquid ammonia containing no proton donor did not give 23 but only 35 in 44% yield. The other attempt with 4.3 equivalents of lithium containing t-butanol as a proton donor gave only 35 in moderate yield (Scheme 10).

Scheme 10.ª

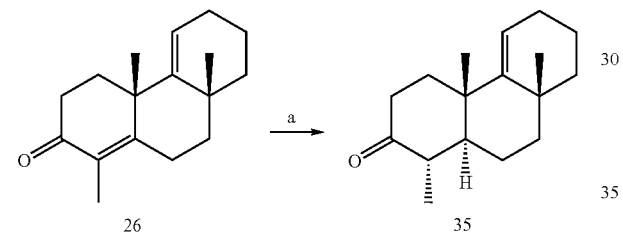

ªReagents: (a) Li (3.3 eq.), liq. NH₃, THF, CH₃I or Li (4.3 eq.), t-butanol (1 eq.), liq. NH₃, THF, CH₃I, etc.

Synthesis of Compounds 29a-29c (1) Synthetic Approach Towards Compound 29b from Acid 30a Attempts of reductive methylation of a known compound 30a, which is prepared in good yield from commercially available 2-carbomethoxycyclohexanone and 1-chloro-3-pentanone by Heathcock's method (Kerwin et al., 1987), with about 5-7 equivalents of lithium in liquid ammonia containing no proton donor, followed by methylation with diazomethane gave 29b in 30% yield (average of 7 experiments) and many by-products. These by-products caused serious difficulty for the purification of 29b. An attempt with one equivalent of water also gave similar results as without a proton donor.

Scheme 11.ª

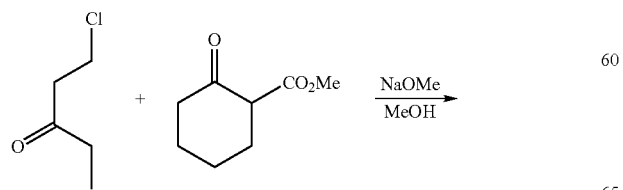

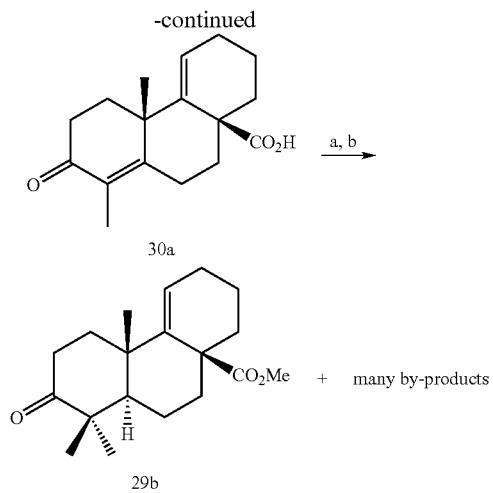

ªReagents: (a) Li, liq. NH₃, THF, CH₃I; (b) CH₂N₂, Et₂O, THF.

(2) Synthetic Approach Towards Compounds 29a-29c from Methyl Ester 30b

Attempts of reductive methylation of 30b, which is prepared from 30a with diazomethane, with about 10 equivalents of lithium in liquid ammonia containing no proton donor gave the desired compounds 29a-29c in low yield and some by-products including enones 30a and 30c. These by-products caused serious difficulty for the purification of 29a-29c.

Scheme 12.ª

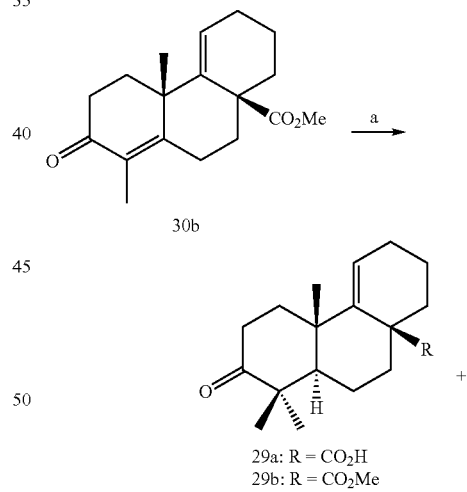

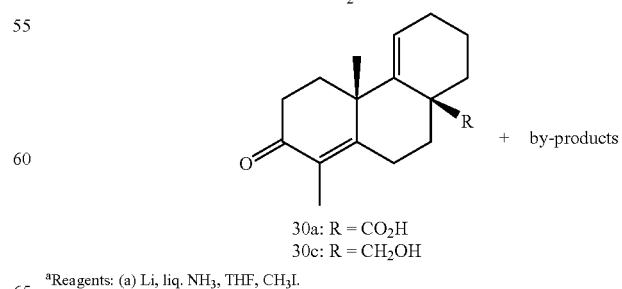

ªReagents: (a) Li, liq. NH₃, THF, CH₃I.

(3) Synthesis of Compounds 29a-29c from Methyl Ester 30b

Reductive methylation of 30b using 7.2 equivalents of lithium and one equivalent of water and quenching the excess lithium with isoprene, followed by the addition of methyl iodide at −78° C. (see the detailed procedure in the EXAMPLE 3) produced the new compounds 29a, 29b, and 29c in 38%, 15%, and 36% yields, respectively. These compounds can be easily separated by a participation method between an organic solvent and basic medium, followed by column chromatography.

Scheme 13.[a] Synthesis of Compounds 29a–29c

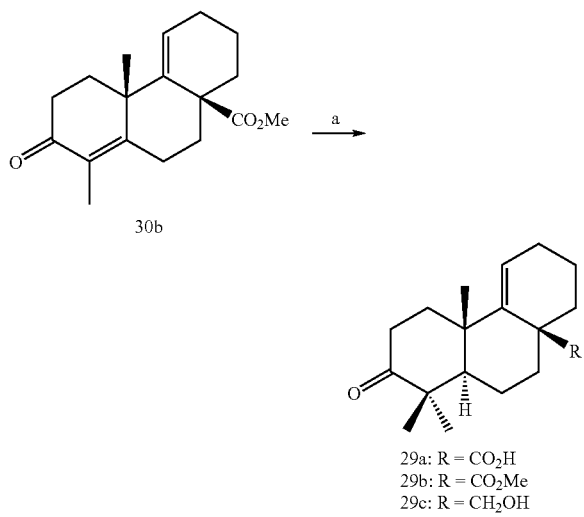

29a: R = CO$_2$H
29b: R = CO$_2$Me
29c: R = CH$_2$OH

[a]Reagents: (a) Li, H$_2$O (1 eq.), liq. NH$_3$, THF, CH$_3$I.

Example 3

Detailed Experimental Procedures for the Synthesis of Compounds 23 and 29a-29c

General Procedures. Melting points were determined on a Thomas-Hoover capillary melting point apparatus and are uncorrected. IR spectra were recorded on a Perkin-Elmer 600 series FTIR spectrophotometer. $^1$H (300 MHz) and $^{13}$C (75 MHz) NMR spectra were recorded on a Varian XL-300 Fourier transform spectrometer. The chemical shifts are reported in δ (ppm) using the δ 7.27 signal of CHCl$_3$ ($^1$H NMR) and the δ 77.23 signal of CDCl$_3$ ($^{13}$C NMR) as internal standards. Low-resolution mass spectra and high-resolution MS data were obtained on a Micromass 70-VSE. Elemental analyses were performed by Atlantic Microlab Inc. All samples prepared for elemental analysis or supplied for biological evaluation were dried at 50-60° C. at reduced pressure (≦0.1 Torr) in a National Appliance Company model 5831 vacuum oven. TLC was performed with Merck precoated TLC plates silica gel 60 F$_{254}$. Flash column chromatography was done with Select Scientific silica gel (230-400 mesh).

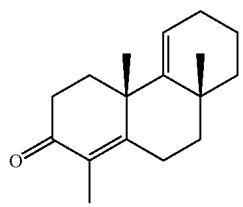

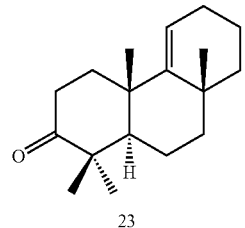

23

(±)-(4aβ,8aβ,10aα)-3,4,4a,6,7,8,8a,9,10,10a-Decahydro-1,1,4a,8a-tetramethylphenanthren-2(1H)-one (23)

Ammonia gas was directed through a KOH drying tube into a 250 mL three-neck round bottom flask equipped with a stopper, dry ice/i-PrOH condenser connected to a nitrogen line, stir bar and dry ice/i-PrOH bath. The flow of gas was stopped after approximately 50 mL had been collected. Lithium (255 mg, 37 mmol, 4.5 eq, sliced ribbon), was washed with hexanes and added to the stirring solution, turning it a deep blue color. The solution was stirred at −78° C. for 20 min. Compound 26 (2.0 g, 8.2 mmol, 1 eq) and water (147 mg, 8.2 mmol, 1 eq) in freshly distilled THF (27 mL) were added dropwise and the solution was stirred at −33° C. (bp of ammonia) (with the aid of a CCl$_4$ bath) for 1 h. The solution was cooled to −78° C. and isoprene was injected until the blue color disappeared (approx 0.5 mL, 5.0 mmol, 0.6 eq), turning the solution white, followed by additional THF (10 mL). The dry ice condenser and bath was then removed from the system and as the reaction mixture rose to room temperature (RT), the ammonia was blown into a 5% HCl (aq.) trap solution as it evaporated with the aid of a nitrogen stream. To the remaining mixture were added iodomethane (10 mL, 160 mmol, 20 eq, d=2.28) and THF (10 mL) successively and the solution was stirred at 0° C. in an ice bath for 1 h. The solution was neutralized with 10% HCl (aq.) (20 mL) and the aqueous layer was extracted with CH$_2$Cl$_2$ (4×50 mL). The combined organic extracts were washed with brine (1×25 mL), dried over MgSO$_4$, filtered and concentrated in vacuum to give 2.16 g of crude material. This off-white solid was purified by flash column chromatography [hexanes:EtOAc 7:1] to give compound 23 (1.34 g, 63%) as a colorless oil that gave semi solids upon standing: mp 34.5-35.5° C.; TLC [hexanes:EtOAc, 7:1] R$_f$ 0.56; IR (KBr): 3049, 2929, 2864, 1707 cm$^{-1}$; $^1$H NMR (CDCl$_3$) δ 5.37 (1H, t, J=3.8 Hz), 2.71 (1H, ddd, J=6.7, 12.6, 15.9 Hz), 2.41 (1H, ddd, J=3.1, 6.0, 15.8 Hz), 2.09-2.03 (3H, m), 1.82-1.28 (10H, m), 1.25, 1.22 (3H each, s), 1.08 (6H, s); $^{13}$C NMR (CDCl$_3$) δ 217.4, 152.0, 118.1, 54.4, 48.0, 43.0, 42.9, 39.2, 37.9, 35.0, 34.5, 28.6, 26.4, 25.9, 22.8, 21.8, 19.8, 18.3; EIMS (70 eV) m/z: 260 [M$^+$] (48), 245 (70), 203 (36), 175 (42), 147 (52), 125 (100), 109 (83); HREIMS Calculated for C$_{18}$H$_{28}$O 260.2140, found: 260.2134.

Li (4.5 eq), NH$_3$ (l), H$_2$O (1 eq)
THF, MeI
63%

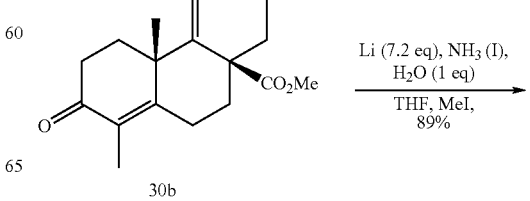

Li (7.2 eq), NH$_3$ (l), H$_2$O (1 eq)
THF, MeI
89%

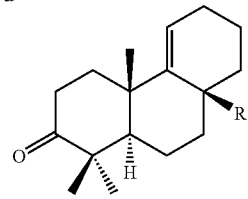

29a: R = CO₂H (Y. 38%)
29b: R = CO₂Me (Y. 15%)
29c: R = CH₂OH (Y. 36%)

(±)-(4aβ,8aβ,10aα)-1,2,3,4,4a,6,7,8,8a,9,10,10a-Dodecahydro-1,1,4a-trimethyl-2-oxo-phenanthrene-8a-carboxylic acid (29a), its methyl ester (29b), and (+)-(4aβ,8aβ,10aα)-3,4,4a,6,7,8,8a,9,10,10a-Decahydro-8a-hydroxymethyl-1,1,4a-trimethylphenanthren-2(1H)-one (29c)

To liquid ammonia (100 mL) was added lithium (600 mg, 86 mmol, 7.2 eq, sliced ribbon), The solution was stirred at −78° C. for 40 min. Compound 30b (3.5 g, 12 mmol) and water (218 mg, 12 mmol, 1 eq) in freshly distilled THF (47 mL) was added dropwise and the solution was stirred at −33° C. (bp of ammonia) (with the aid of a CCl₄ bath) for 1 h. The solution was cooled to −78° C. and isoprene (approx. 1.25 mL,) was injected until the blue color disappeared turning the solution white. Subsequently, to the solution were added THF (17.5 mL) and iodomethane (17.5 mL) dropwise. The reaction mixture was stirred at −33° C. (bp of ammonia) for 1 h. The dry ice condenser and bath were then removed from the system and as the reaction mixture rose to rt, the ammonia was blown into a 5% HCl (aq.) trap solution as it evaporated with the aid of a nitrogen stream. The solution was neutralized with 10% HCl (aq.) and the aqueous layer was extracted with CH₂Cl₂ (4×50 mL). The combined organic extracts were washed with brine (1×25 mL), dried over MgSO₄, filtered and concentrated in vacuo to give 3.8 g of crude material. A solution of the material in methylene chloride (100 mL) was extracted with 5% aqueous NaOH solution (2×25 mL) and water (1×25 mL). To acidify the aqueous extract was added 10% aqueous HCl solution. A colorless solid was precipitated. The acidic aqueous mixture was extracted with methylene chloride (3×25 mL). The extract was washed with water (3×25 mL), brine (1×25 mL), dried over MgSO₄, and filtered. The filtrate was evaporated in vacuo to give acid 29a as an amorphous solid (1.33 g, 38%) The methylene chloride layer including neutral compounds was washed with saturated aqueous ammonium chloride solution (2×25 mL), brine (2×25 mL), dried over MgSO₄, and filtered. The filtrate was evaporated in vacuo to give a residual oil (2.33 g). It was purified by flash column chromatography [hexanes:EtOAc 3:1, followed by 2:1] to give methyl ester 29b (547 mg, 15%) and alcohol 29c (1.21 g, 36%) as crystalline solids.

Acid 29a: TLC: hexanes:EtOAc (2:1), $R_f$ 0.37. IR (KBr): 3200, 2943, 1691, 1457 cm⁻¹. ¹H NMR (CDCl₃): δ 5.72 (1H, dd, J=3.1, 4.6 Hz), 2.73 (1H, ddd, J=6.3, 13.6, 15.8 Hz), 2.58 (1H, dt, J=3.2, 13.4 Hz), 2.41 (1H, ddd, J=3.0, 5.2, 15.8 Hz), 1.16, 1.06, 1.04 (3H each, s) ¹³C NMR (CDCl₃): δ 217.0, 183.3, 144.5, 122.4, 54.5, 48.0, 45.5, 40.2, 38.34, 38.27, 36.8, 35.0, 25.8, 25.5, 22.2, 21.04, 21.03, 18.0. EIN4S (70 eV) m/z: 290 [M⁺] (20), 245 (26), 91 (100). HREIMS: Calcd for C₁₈H₂₆O₃ 290.1882. Found: 290.1880.

Methyl ester 29b: mp 90-92° C. TLC: hexanes:EtOAc (4:1), $R_f$ 0.56. IR (KBr): 2941, 2858, 1716, 1445 cm⁻¹. ¹H NMR (CDCl₃): δ 5.68 (1H, dd, J=3.5, 4.6 Hz), 3.70 (3H, s), 2.73 m(1H, ddd, J=6.4, 13.6, 16.0 Hz), 2.60 (1H, dt, J=3.3, 13.3 Hz), 2.41 (1H, ddd, J=3.0, 5.2, 16.0 Hz), 1.06 (6H, s), 1.03 (3H, s). ¹³C NMR (CDCl₃): δ 216.7, 177.4, 145.1, 121.8, 54.6, 51.9, 47.9, 45.6, 40.1, 38.6, 38.3, 36.8, 35.0, 25.8, 25.6, 22.1, 21.0, 20.0, 18.2. EIMS (70 eV) m/z: 304 [M⁺] (31), 245 (100), 159 (33). HREIMS: Calcd for C₁₉H₂₈O₃ 304.2038. Found: 304.2039.

Alcohol 29c: mp 109-110° C. TLC: hexanes:EtOAc (2:1), $R_f$ 0.43. IR (KBr): 3454, 2931, 2859, 1645, 1448 cm⁻¹. ¹H NMR (CDCl₃): δ 5.67 (1H, t, J=3.8 Hz), 3.68 (2H, s), 2.68 (1H, ddd, J=6.6, 12.5, 15.7 Hz), 2.43 (1H, ddd, J=3.3, 5.9, 15.7 Hz), 1.20 (1H, d, J=0.6 Hz), 1.08 (3H, s), 1.06 (3H, s). ¹³C NMR (CDCl₃): δ 217.0, 148.0, 123.0, 67.0, 54.1, 47.9, 39.7, 39.0, 38.0, 37.1, 36.7, 34.9, 26.1, 26.0, 22.6, 21.8, 19.7, 18.1. EIMS (70 eV) m/z: 276 [M⁺] (6.1), 245 (100), 227 (10), 203 (6.1). HREIMS: Calcd for C₁₈H₂₈O₂ 276.2089. Found: 276.2082.

Example 4

Design and Synthesis of TBE Compounds with Functionalities at C-8

Synthesis of TBE-12-19

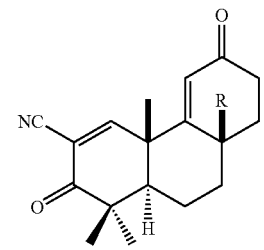

(±)-TBE-12: R = CO₂Me
(±)-TBE-13: R = CH₂OH
(±)-TBE-14: R = CN
(±)-TBE-15: R = CH₂OSiMe₂(t-Bu)
(±)-TBE-16: R = CH₂NHCOO(t-Bu)
(±)-TBE-17: R = CH₂NH₂
(±)-TBE-18: R = CH₂NH₂·HCl
(±)-TBE-19: R = CO₂H

36: R = CONH₂
37: R = CH₂X
[X = F(37f), Cl, Br]
38: R = CH₂OAc
39: R = CHO

The inventors are interested in TBEs with functionalities at C-8 as shown above for the following reasons: (1) Starting materials 29a-29c for their syntheses can be easily made (see EXAMPLES 2 and 3) and (2) insertion of functionalities at C-8 of TBEs is expected to improve their potency and pharmacokinetics because the balance between hydrophilicity and hydrophobicity is shifted. Particularly, because TBEs with CO₂Na and NH₃Cl moieties at C-8 (e.g., sodium salt of TBE-19, TBE-18, etc.) would be water-soluble compounds, they strongly affect such parameters. The inventors have synthesized novel TBE compounds, called TBE-12-19 (Schemes 1418). Also compounds 36-39 would be synthesized as shown in Schemes 19-21.

Synthesis of (±)-TBE-13 and 15

Scheme 14.

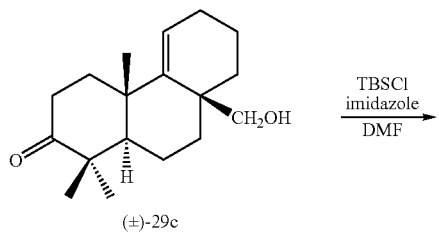
(±)-29c

TBSCl
imidazole
DMF
→

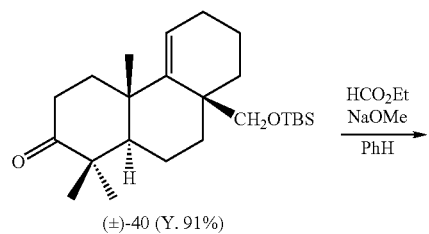
(±)-40 (Y. 91%)

HCO₂Et
NaOMe
PhH
→

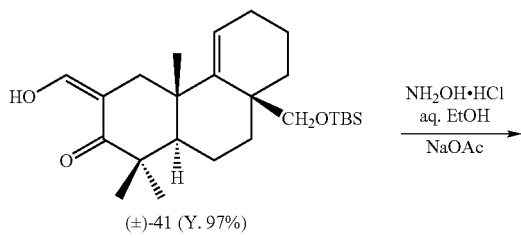
(±)-41 (Y. 97%)

NH₂OH·HCl
aq. EtOH
NaOAc
→

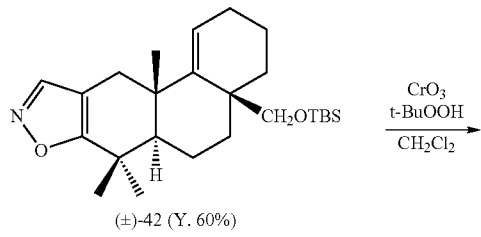
(±)-42 (Y. 60%)

CrO₃
t-BuOOH
CH₂Cl₂
→

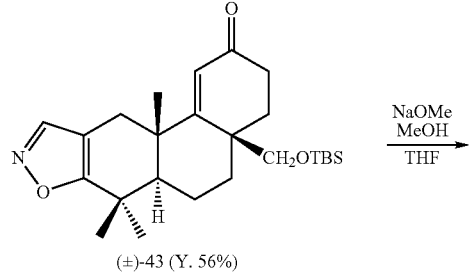
(±)-43 (Y. 56%)

NaOMe
MeOH
THF
→

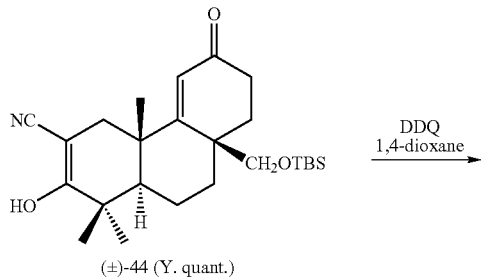
(±)-44 (Y. quant.)

DDQ
1,4-dioxane
→

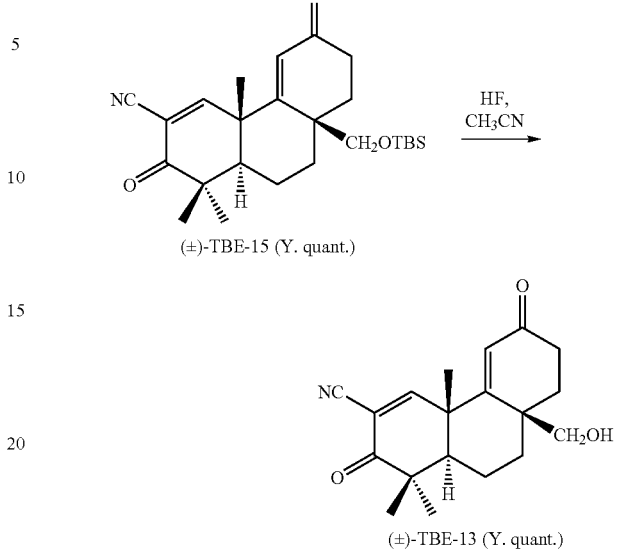

(±)-TBE-15 (Y. quant.)

HF,
CH₃CN
→

(±)-TBE-13 (Y. quant.)

Protected alcohol 40 was obtained from 29c in 91% yield. Formylation of 40 gave 41 in 97% yield. Condensation of 41 with hydroxylamine hydrochloride gave 10 isoxazole 42 in 60% yield. Allylic oxidation of 42 gave 43 in 56% yield. Cleavage of isoxazole ring of 43 gave 44 in quantitative yield. DDQ oxidation of 44 gave TBE-15 quantitatively. Removal of TBS group with aqueous HF in acetonitrile gave TBE-13 quantitatively.

Synthesis of TBE-14

Scheme 15.

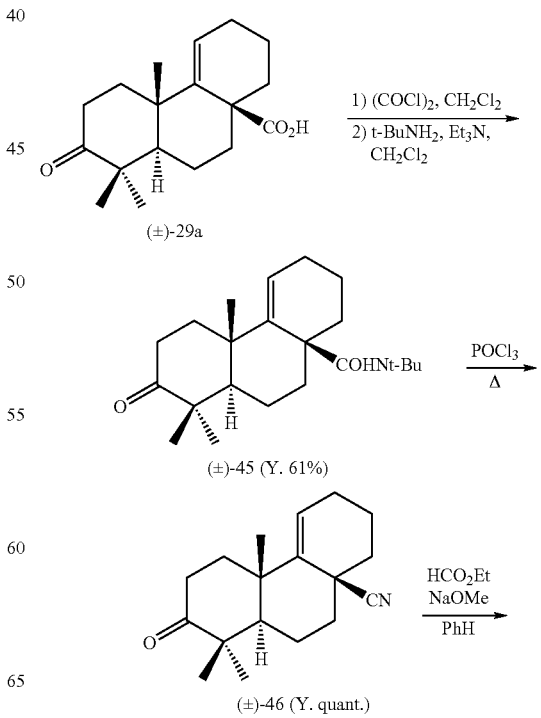

(±)-29a 1) (COCl)₂, CH₂Cl₂
2) t-BuNH₂, Et₃N, CH₂Cl₂
→

(±)-45 (Y. 61%)

POCl₃
Δ
→

(±)-46 (Y. quant.)

HCO₂Et
NaOMe
PhH
→

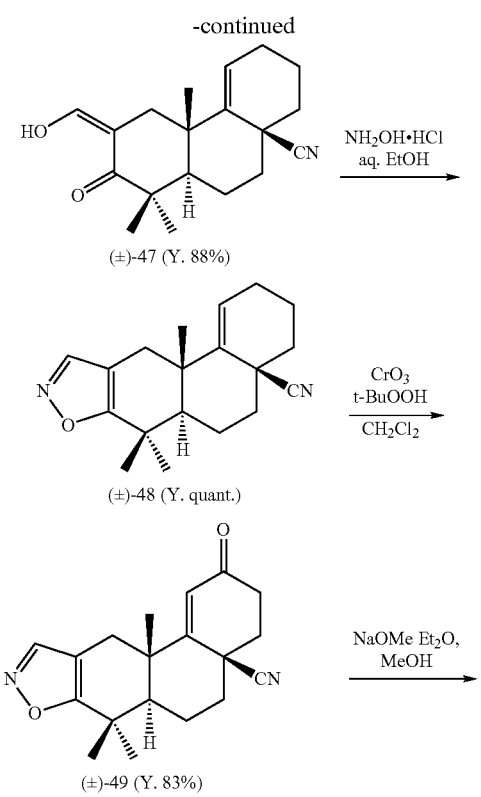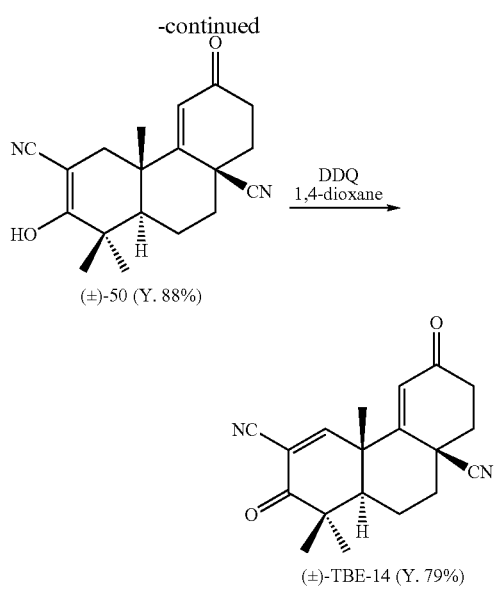
Tert-butyl amide 45 was obtained in two steps from 29a in 61% yield. Neat POCl$_3$ gave 46 quantitatively. Formylation of 46 gave 47 in 88% yield. Isoxazole 48 was obtained from 47 in quantitative yield. Allylic oxidation of 48 gave 49 in 83% yield. Cleavage of isoxazole of 49 gave 50 in 88% yield. DDQ oxidation of 50 gave TBE-14 in 79% yield.
Synthesis of TBE-16-18
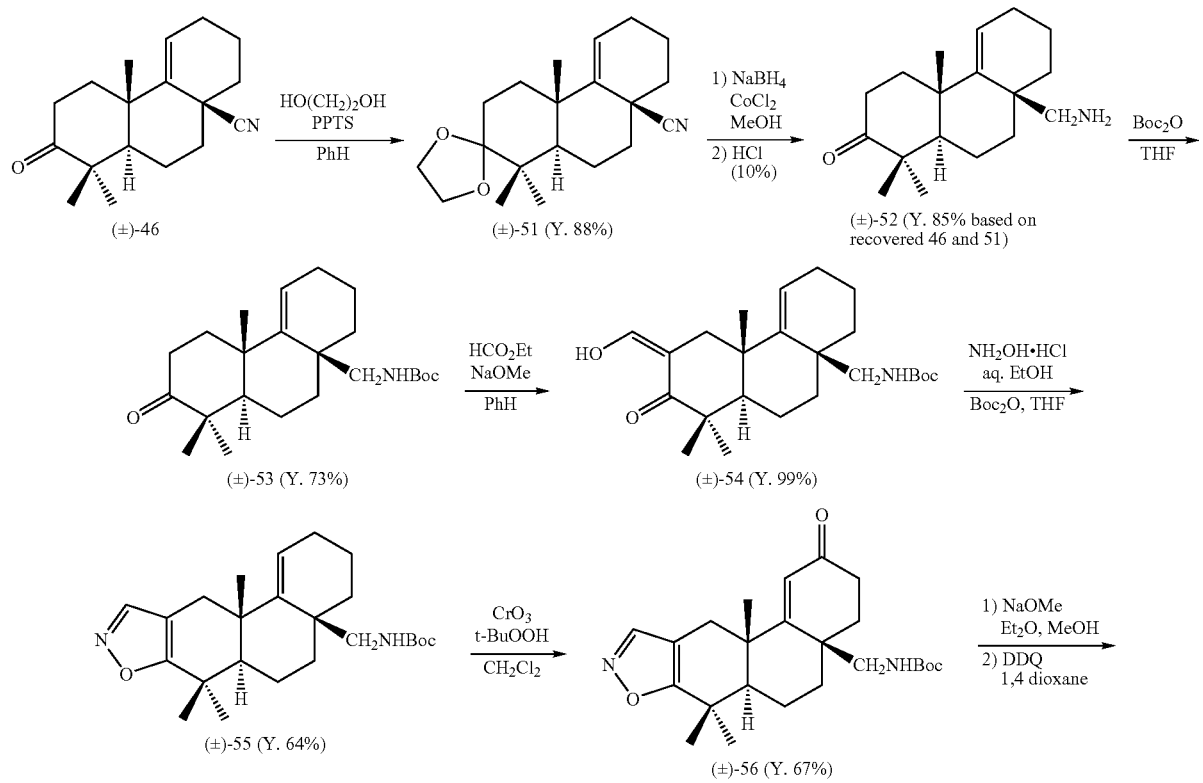

-continued

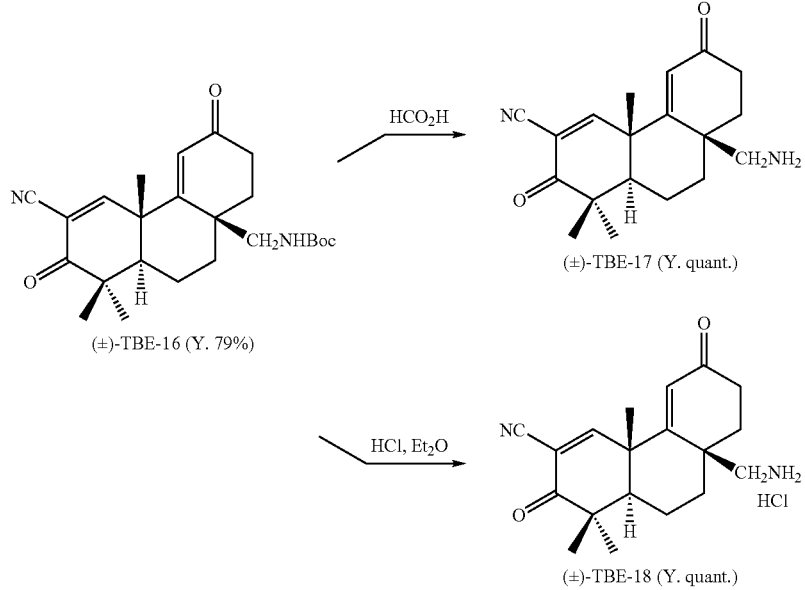

Ketalization of 46 gave 51 in 88% yield. Reduction of nitrile group of 51 with a mixture of NaBH$_4$ and CoCl$_2$ in methanol, followed by acidification with 10% aqueous HCl solution, gave 52 (yield based on recovered 46 and 51, 85%). Boc$_2$O gave protected amine 53 in 73% yield. Formylation of 53 gave 54 in 99% yield. Condensation of 54 with hydroxylamine hydrochloride gave isoxazole 55 in 64% yield. Allylic oxidation of 55 gave 56 in 67% yield. TBE-16 was synthesized in two steps from 56 in 79% yield. Deprotection of TBE-16 with formic acid gave TBE-17, quantitatively. Deprotection of TBE-16 with hydrogen chloride in ether gave TBE-18, TBE-17 hydrochloride, quantitatively. TBE-18 should be soluble in water.

Synthesis of TBE-12 and 19

-continued

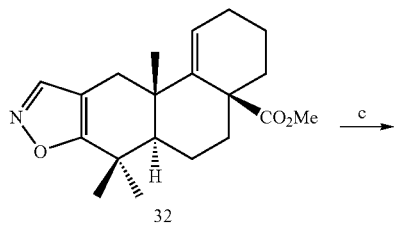

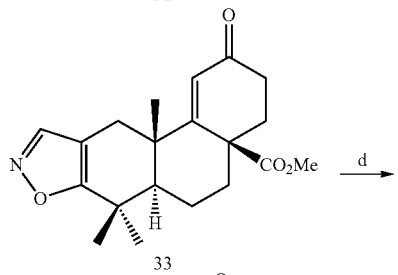

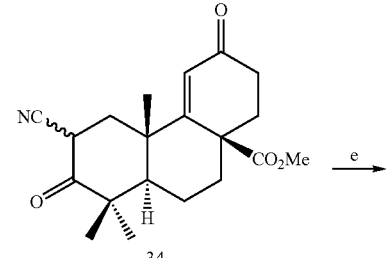

Scheme 17.$^a$

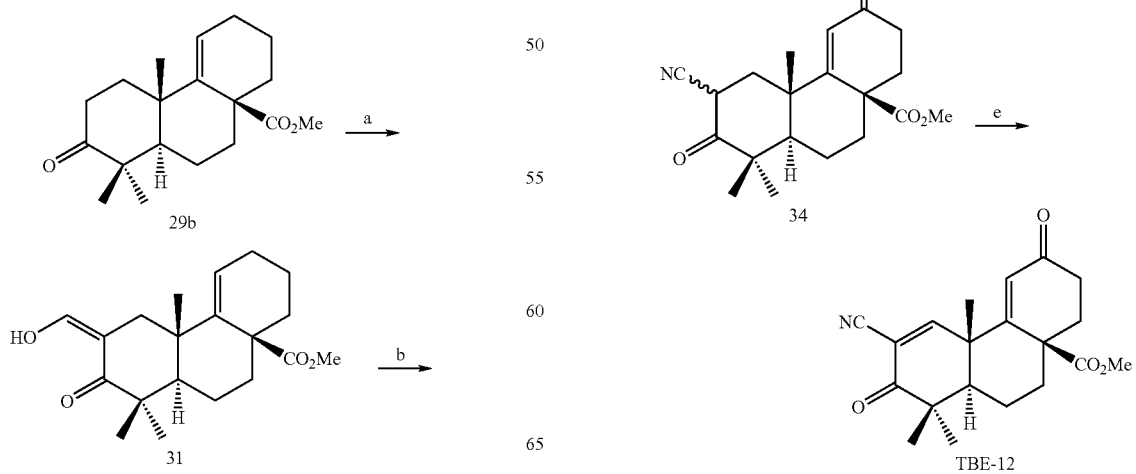

Formylation of 29b gave 31 in 95% yield. Isoxazole 32 was obtained in 99% yield by condensation of 31 with hydroxylamine. Allylic oxidation of 32 with a catalytic amount of $CrO_3$ and t-BuOOH gave enone 33 in 55% yield. Nitrile 34 was prepared in 79% yield by cleavage of isoxazole with sodium methoxide. DDQ oxidation of 34 gave TBE-12 in 89% yield.

Scheme 18.

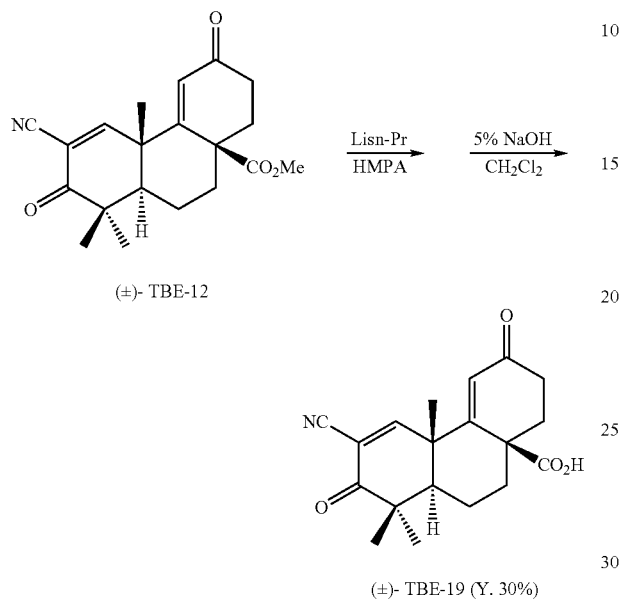

Treatment of TBE-12 with lithium n-propylmercaptide in HMPA, followed by treatment of 5% aqueous NaOH solution, gave TBE-19 in 30% yield.

Synthesis of TBE Compounds 36-39

Scheme 19.[a]

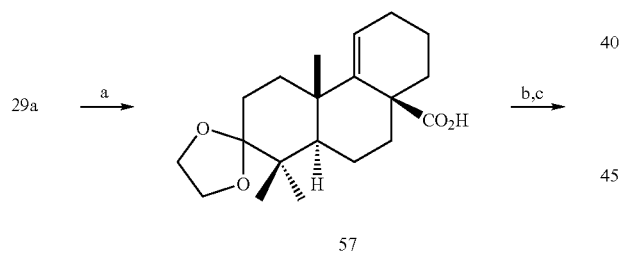

[a] Reagents: (a) ethylene glycol, PPTS, PhH; (b) (COCl)$_2$, CH$_2$Cl$_2$; (c) NH$_3$, PhH; (d) PPTS, aq acetone; (e) LDA, p-TsCN; (f) DDQ, PhH; (g). CrO$_3$, t-BuO$_2$H.

Scheme 20.[a]

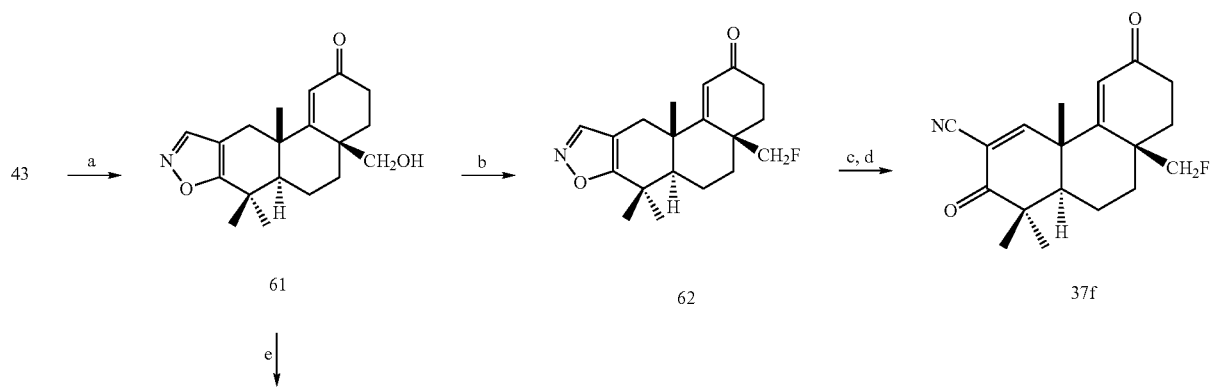

-continued

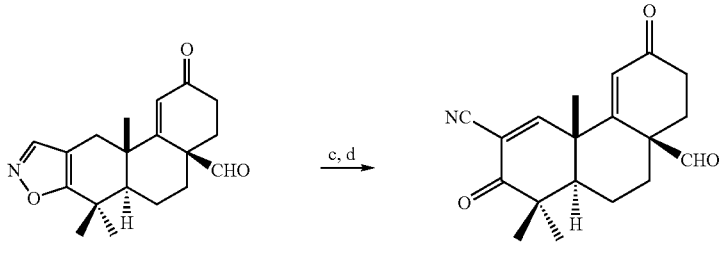

a Reagents: (a) aqueous HF, CH$_3$CN; (b) DAST, CH$_2$Cl$_2$; (c) NaOMe, MeOH, Et$_2$O; (d) DDQ, PhH; (e) (COCl)$_2$, DMSO, CH$_2$Cl$_2$.

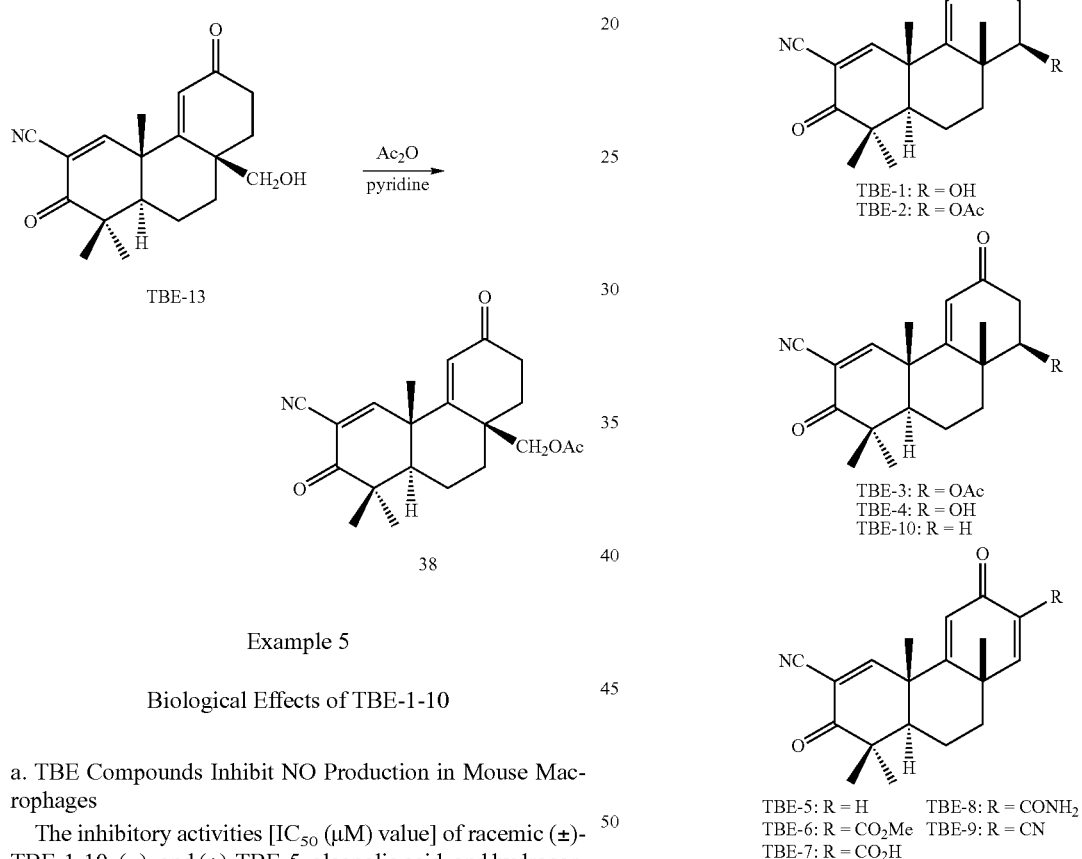

Example 5

Biological Effects of TBE-1-10 a. TBE Compounds Inhibit NO Production in Mouse Macrophages

The inhibitory activities [IC$_{50}$ (μM) value] of racemic (±)-TBE-1-10, (−)- and (+)-TBE-5, oleanolic acid, and hydrocortisone (a positive control) on NO production induced by IFN-γ in mouse macrophages are shown in Table 1. The following results were obtained: (1) TBE-9 showed the highest potency in this assay. The potency of TBE-9 is about 5 and 30 times more than hydrocortisone and TBE-5, respectively. (2) TBE-10 is about 3 times more potent than TBE-5. This result is very important as it indicates that the 13-en-12-one functionality is not always necessary for potency. (3) As TBE-3 and 4 are more potent than TBE-1 and 2, the bis-enone structure is very important for high potency even in relatively small molecules. (4) Both enantiomers, (−)- and (+)-TBE-5 show the same potency. (5) It was also found that these TBE compounds do not act through the glucocorticoid receptor (data not shown).

TABLE 1

Inhibitory Activity of TBE-1–10 in iNOS Assay (blocking of induction of iNOS by IFN-γ)

| Compound | Activity IC$_{50}$ (μM) |
| --- | --- |
| (±)-TBE-1 | 0.31 |
| (±)-TBE-2 | 0.48 |
| (±)-TBE-3 | 0.053 |
| (±)-TBE-4 | 0.075 |
| (±)-TBE-5 | 0.061 |
| (−)-TBE-5 | 0.064 |
| (±)-TBE-5 | 0.058 |
| (±)-TBE-6 | 0.091 |

TABLE 1-continued

Inhibitory Activity of TBE-1–10 in iNOS Assay (blocking of induction of iNOS by IFN-γ)

| Compound | Activity IC$_{50}$ (μM) |
|---|---|
| (±)-TBE-7 | 1.60 |
| (±)-TBE-8 | 0.061 |
| (±)-TBE-9 | 0.0021 |
| (±)-TBE-10 | 0.019 |
| Oleanolic acid | >40 |
| Hydrocortisone | 0.01 | b. TBE Compounds Suppress iNOS and COX-2 mRNA in RAW 264.7 Cells

TBE-3 suppresses the formation of iNOS and COX-2 mRNA at 1 μM in RAW cells. Both potencies were about 10 times less than CDDO (see FIG. 1, data for TBE-4 and 5 not shown. TBE-9 has not yet been examined.

c. TBE Compounds Inhibit Growth of MCF-7 Breast Cancer Cells

TBE-3 and 5 inhibit estrogen-stimulated growth of MCF-7 breast cancer cells (ER-positive) in a dose-dependent manner, over a range of 0.3-10 μM (see FIG. 2).

TBE-9 inhibits estrogen-stimulated growth of MCF-7 breast cancer cells (ER-positive) in a dose-dependent manner, over a range of 10-1000 nM. The potency is about 30 times more than TBE-5 (see FIG. 3).

d. TBE Compounds Inhibit Proliferation of NRP-152 Prostate Cells

TBE-3 and 5 inhibit proliferation of NRP-152 prostate epithelial cells at the IC$_{50}$ $10^{-7}$ M level (FIG. 4).

e. TBE-9 is Orally Active in an In Vivo Model of Inflammation

TBE-9 is orally active at 15 and 30 mg/kg (administered once) in in vivo studies using mouse peritoneal inflammation induced by thioglycollate and IFN-γ and shows no signs of toxicity at either dose. These studies also revealed that TBE-9 is much more potent than hydrocortisone (FIG. 5).

Example 6

Design and Synthesis of TBE Analogs

This example provides methods for the design and synthesis of various TBE analogs.

a. Design and Synthesis of Racemic TBE-9 Analogs

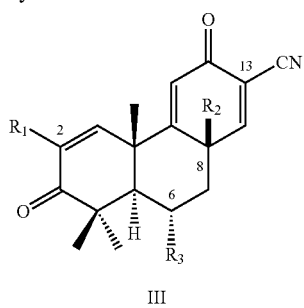

III

R$_1$ = CN, CO$_2$H, etc.
R$_2$ = CH$_3$, CO$_2$R$_4$, CONHR$_4$, CHO, CN, CH$_2$NHR$_5$, CH$_2$OR$_5$, CH$_2$X (X = F, Cl, Br), etc.
R$_3$ = H, OH

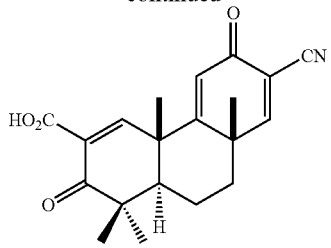

64

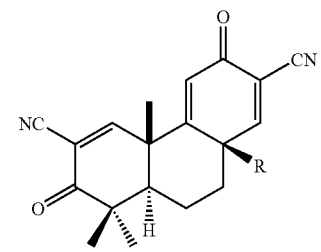

65: R = CO$_2$H
66: R = CN
67: R = CH$_2$NH$_2$
68: R = CH$_2$F

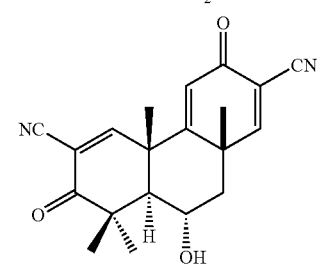

69

As TBE-9 shows excellent potency (1 nM level) in the iNOS assay, the present inventors contemplate that TBE-9 is a new lead compound and a good scaffold from which to discover new, more potent TBE compounds. Thus, the inventors have initially designed TBE-9 analogs having general formula III as shown above.

Specific target compounds 64-69 are also shown above. Acid 64 was designed as the inventors previous work revealed that a carboxyl group at C-2 also shows good potency in the iNOS assay (Honda and Gribble et al., 2000; Honda and Rounds et al., 2000). Salts of 64 are expected to have good solubility in water. Acid 64 can be synthesized 11 steps via 23 from commercial compounds by the synthetic route shown in Scheme 22.

Scheme 22.$^a$

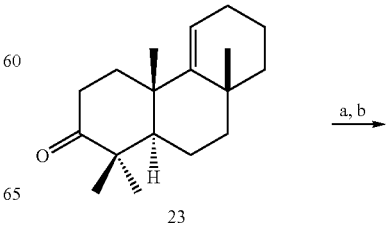

23

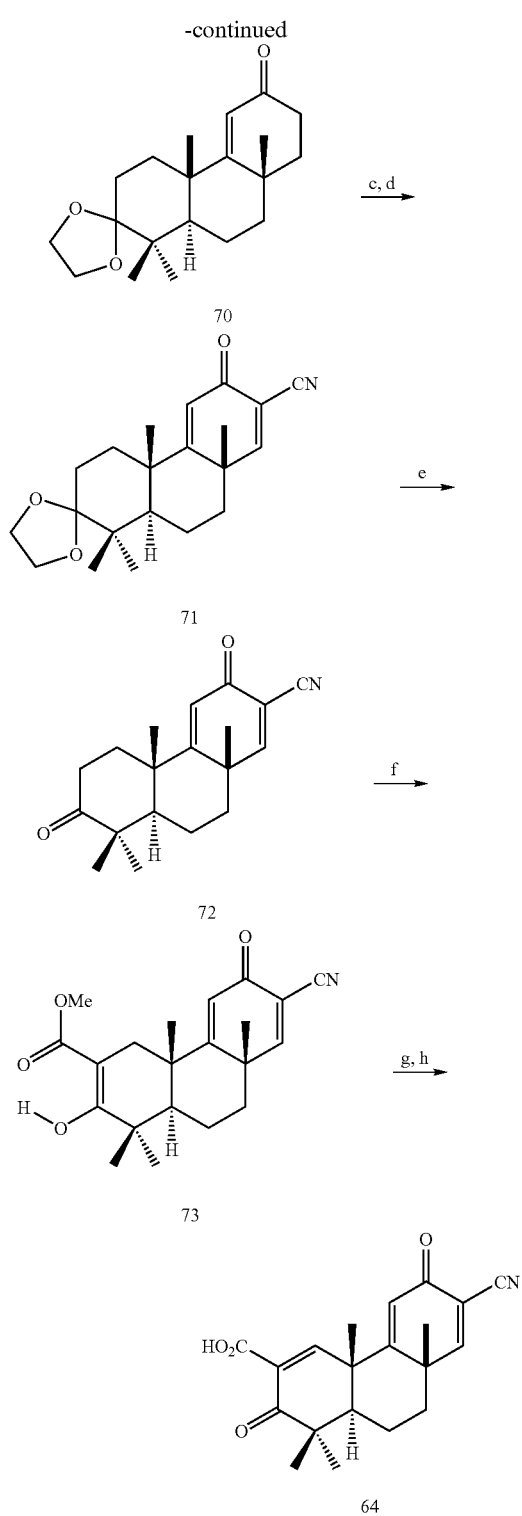

[a] Reagents: (a) HOCH$_2$CH$_2$OH, PPTS, PhH; (b) CrO$_3$, t-BuOOH, CH$_2$Cl$_2$; (c) LDA, p-TsCN, THF; (d) DDQ, PhH; (e) PPTS, aq. acetone; (f) NaH, KH, Me$_2$CO$_3$, THF; (g) PhSeCl, pyr., CH$_2$Cl$_2$; 30%H$_2$O$_2$; (h) KOH, aq. MeOH.

Acid 65 and amine 67 were designed because their salts would have good solubility in water. Nitrile 66 was designed by analogy because a cyano group always enhances potency against inhibition of NO production induced by IFN-γ in these triterpenoids and TBE compounds. Fluoride 68 was designed because there are many examples that fluorine enhances potency. Compounds 65-68 can be synthesized from the same intermediate 29b (or 29a), whose synthesis is described in EXAMPLES 2 and 3. As 65-68 have two cyano groups at C-2 and 13, both cyano groups can be introduced at the same time by double cyanation. Therefore, they can be synthesized in a few steps from commercially available compounds. Compounds 65 and 66 can be synthesized by the sequence shown in Scheme 23. Amine 67 and fluoride 68 can be synthesized by the sequence shown in Schemes 24 and 25, respectively. Likewise, compounds with the other substituents at C-8 can be synthesized according to a similar sequence.

Scheme 23.[a]

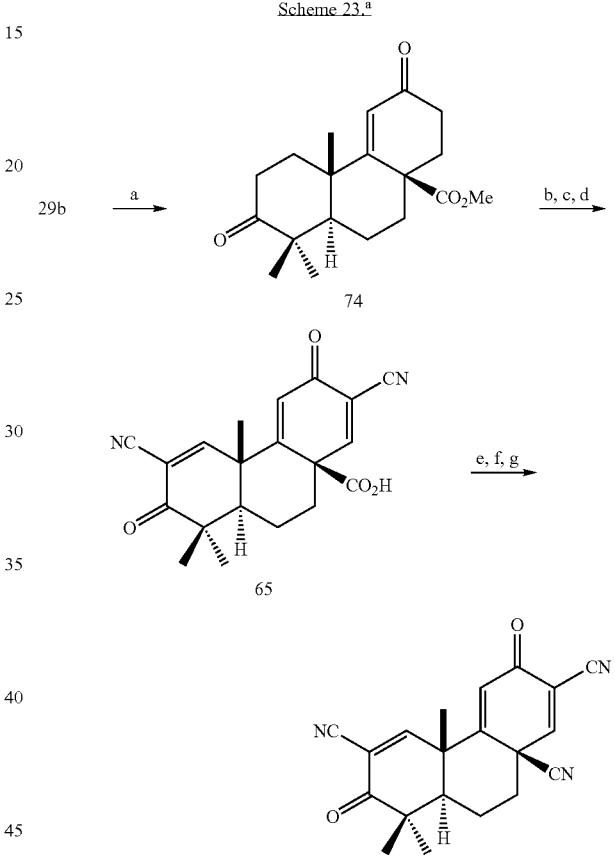

[a] Reagents: (a) CrO$_3$, t-BuOOH, CH$_2$Cl$_2$; (b) LDA, p-TsCN; (c) DDQ, PhH; (d) LiI, DMF; (e) (COCl)$_2$, CH$_2$Cl$_2$; (f) t-BuNH$_2$; (g) POCl$_3$, toluene Scheme 24[a]

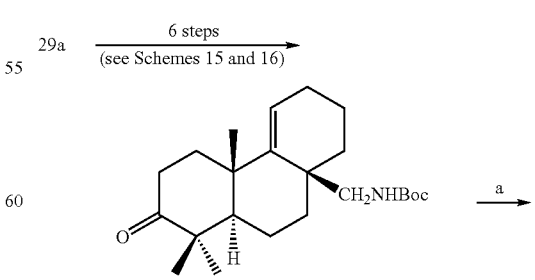

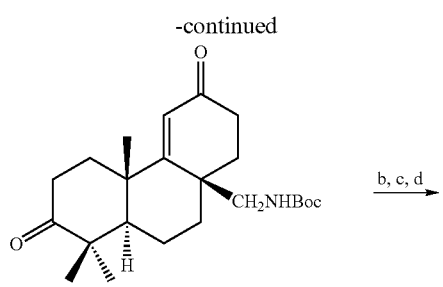

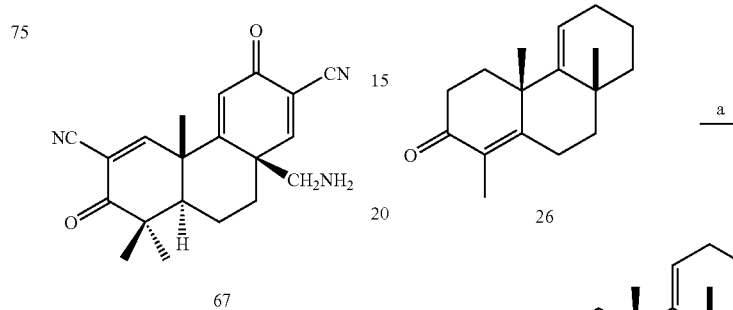

a Reagents: (a) CrO₃, t-BuOOH, CH₂Cl₂; (b) LDA, p-TsCN; (c) DDQ, PhH; (d) HCl, EtOAc.

Scheme 25ᵃ

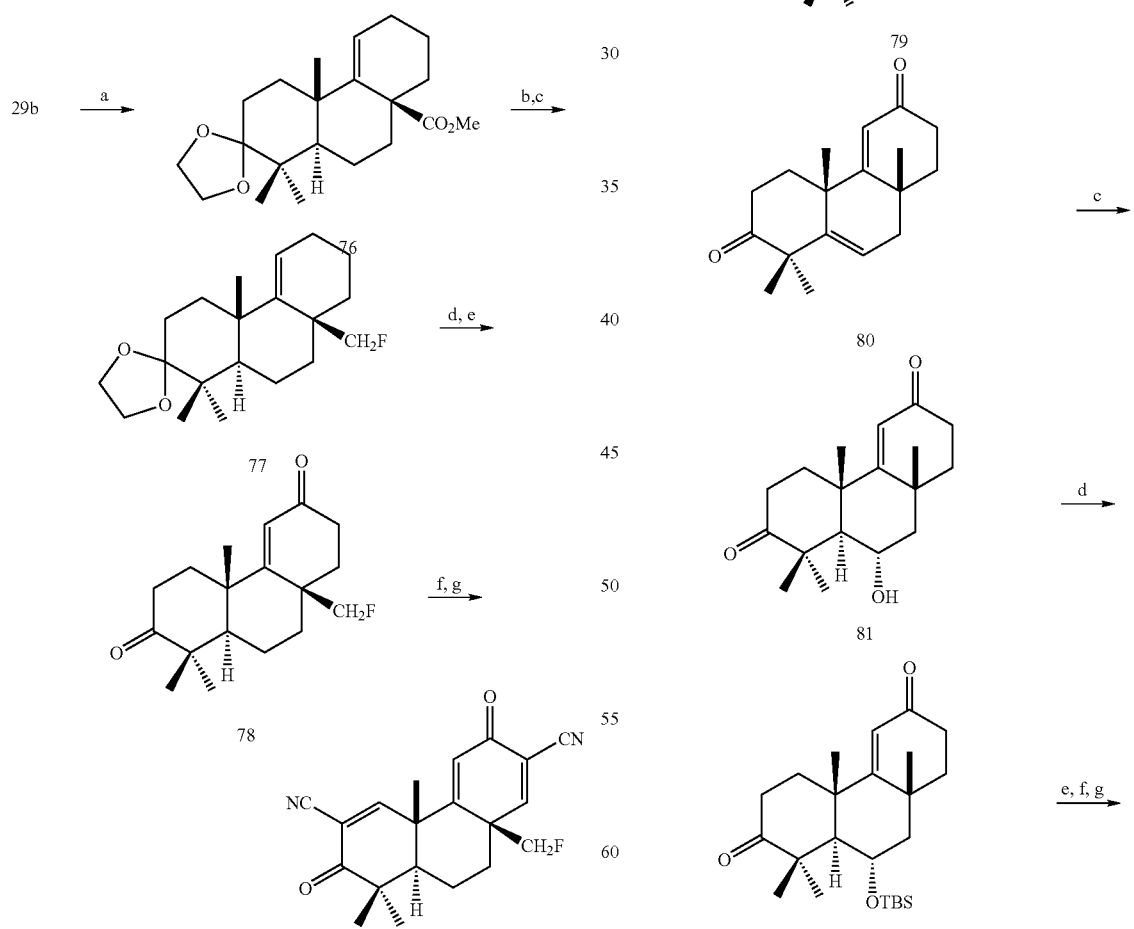

a Reagents: (a) HOCH₂CH₂OH, PPTS, PhH; (b) LAH; (c) DAST; (d) PPTS, aq. acetone; (e) CrO₃, t-BuOOH, CH₂Cl₂; (f) LDA, p-TsCN; (g) DDQ, PhH.

Alcohol 69 can be synthesized from 26 according to the synthetic route shown in Scheme 26. Compound 79 can be obtained from 26 with CH₃I in the presence of t-BuOK (for example, Snitman et al., 1978). It has been reported that allylic oxidation at C-7 is very slow (Honda et al., 1981; Hirota et al., 1991), thus, enone 80 can be prepared selectively. Hydroboration would give 81 mainly because the β-face of the Δ⁵ double-bond is more hindered than the α-face.

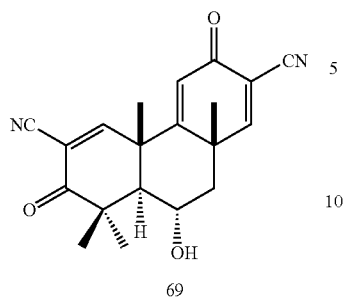

69

[a] Reagents: (a) t-BuOK, t-BuOH, CH$_3$I; (b) CrO$_3$, t-BuOOH, CH$_2$Cl$_2$; (c) B$_2$H$_6$, THF; NaOH aq.; (d) t-Butyldimethylsilyl chloride, imidazole, DMF; (e) LDA, p-TsCN; (f) DDQ, PhH; (g) (n-Bu)$_4$NF.

b. Design and Synthesis of Racemic TBE-10 Analogs

The inventors have also used TBE-10 as a lead compound for synthesis of analogs for the following reasons: 1) TBE-10 is about 3 times more potent than TBE-5. 2) This indicates that the 13-en-12-one functionality is not always necessary for potency. 3) Diminution of a Michael acceptor might reduce the possibility of toxicity. The inventors have designed TBE-10 analogs having general formula IV, which can be derived in relatively few steps from intermediates 23 and 29c, see scheme below.

Racemic TBE-10 Analogs

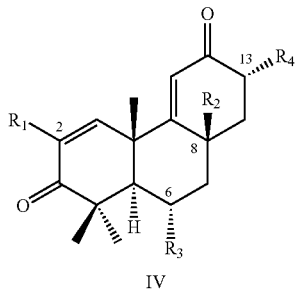

IV

R$_1$ = CN, CO$_2$H, etc.
R$_2$ = CH$_3$, CO$_2$R$_5$, CONHR$_5$, CHO, CN, CH$_2$NHR$_6$, CH$_2$OR$_6$, CH$_2$X (X = F, Cl, Br), etc.
R$_3$ = H, OH
R$_4$ = H, CN, CH$_2$NR$_7$R$_8$ (CH$_2$)$_n$CO$_2$R$_5$ etc.

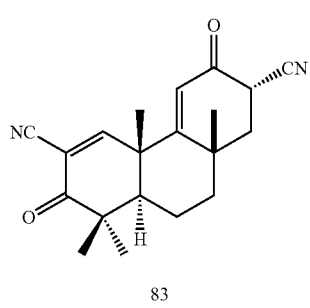

83

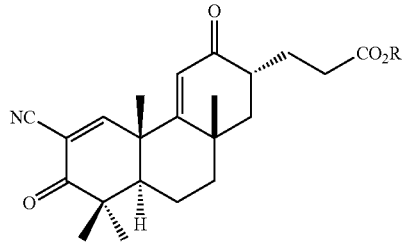

84: R = Et, H, etc.

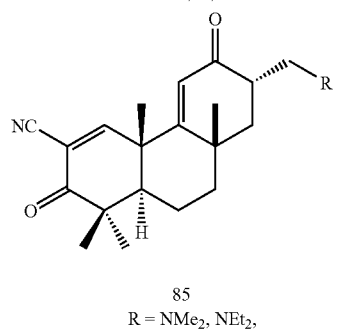

85
R = NMe$_2$, NEt$_2$,

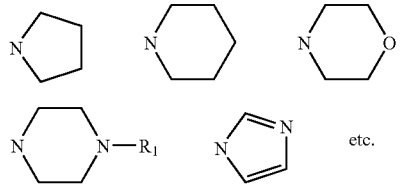

etc.

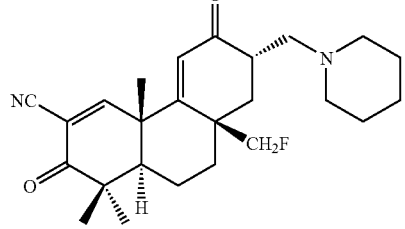

86

Specific target compounds 83-85 are shown above. Dinitrile 83 (TBE-9 without a double-bond at C-13) was designed because TBE-10 (TBE-5 without a double-bond at C-13) is more potent than TBE-5. This compound can be produced predominantly by cyanation of TBE-10 because the α-cyano group (equatorial) is more stable (9 steps from commercial compounds) (Scheme 27).

Scheme 27[a]

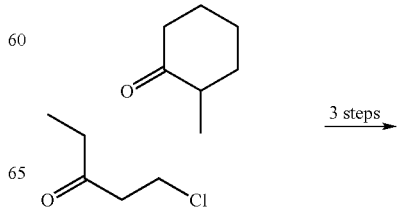

3 steps

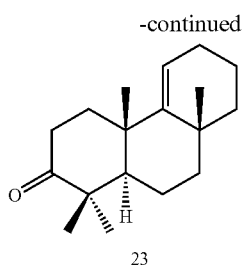

23

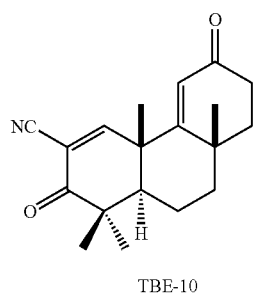

TBE-10

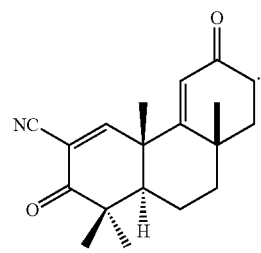

84

<sup>a</sup>Reagents: (a) LDA, p-TsCN.

A series of compounds 84 can be synthesized via enamine 87 (Stork et al., 1963) from TBE-10 (10-11 steps from commercial materials) (Scheme 28).

Scheme 28<sup>a</sup>

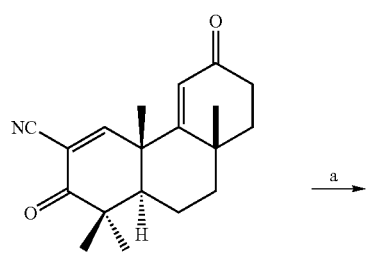

TBE-10

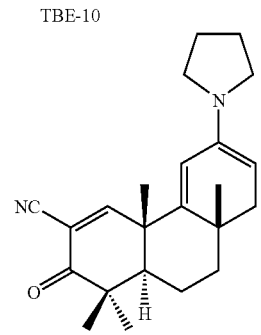

87

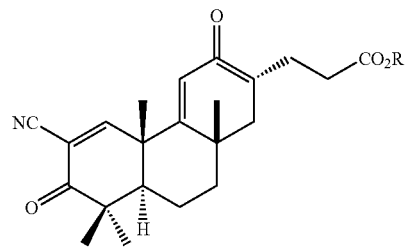

84: R = Et
R = H } c

<sup>a</sup>Reagents: (a) pyrrolidine, PhH; (b) $CH_2$═CH—$CO_2Et$, dioxane; (c) KOH, aq. MeOH.

A series of amines 85 was designed for the following reasons: 1) In many cases, amine side chains like pyrrolidine, piperidine, imidazole, etc. affect biological properties, i.e., potency and pharmacokinetics, etc. of the mother compounds. 2) Salts of these amines are soluble in water. They would be easily synthesized from TBE-10 by Mannich reactions with amines and formaldehyde under basic or acidic conditions (9 steps from commercially available materials) (Scheme 29). If, for example, a fluoromethyl group enhances the potency of TBE-9 in the series of TBE-9 analogs with functionalites at C-8, and a piperidinomethyl group at C-13 enhances the potency of TBE-10 in the series of amines 85, compound 86 can be designed with both functionalities. Compound 86 can be synthesized from 37f (Scheme 30). Similarly, if other functionalities at C-8 and methylamine side chains at C-13 enhance the potency of TBE-9 and 10, respectively, the inventors can design and synthesize compounds with the relevant combinations.

Scheme 29<sup>a</sup>

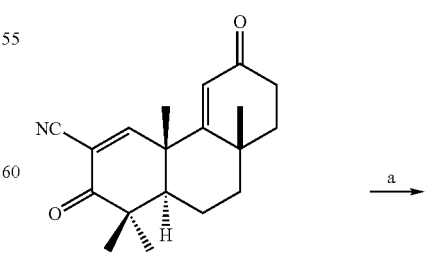

TBE-10

-continued

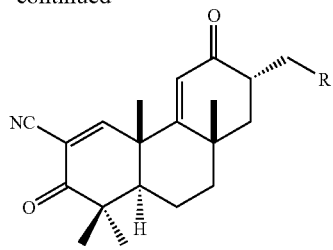

85

R = NMe₂, NEt₂,

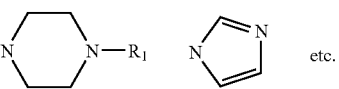  etc.

ᵃReagents: (a) HCHO, amines.

Scheme 30ᵃ

29c $\xrightarrow[\text{(see Scheme 14 and 20)}]{\text{8 steps}}$

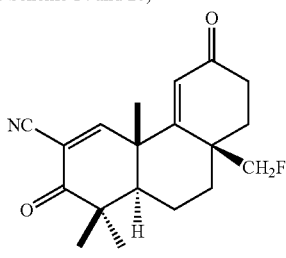

37f a →

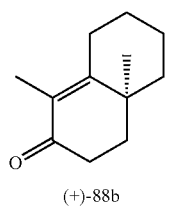

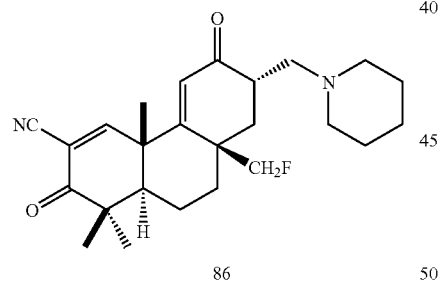

86

ᵃReagents: (a) HCHO, piperidine.

c. Synthesis of Optically Pure TBE-9 and 10 Analogs

Surprisingly, both enantiomers (−)- and (+)-TBE-5 show the same potency in the iNOS assay (see Table 1). They also showed the same inhibitory activity against several cancer cell lines (data not shown). These results cannot be explained by racemization of both enantiomers in living cells because it is chemically impossible for them to racemize. One possibility is that TBE-5 does not have enough potency for the comparison of both enantiomers. Therefore, if analogs more potent than TBE-5 can be obtained among the TBE-9 and 10 analogs as shown above in Example 5-a and b, the inventors contemplate the preparation of optically pure enantiomers to compare them in biological assays. For these purposes, optically pure intermediates 23 and 29a-29c must be synthesized. Optically pure enantiomers 23a and 23b can be synthesized from known optically active compounds (−)-88a and (+)-88b (Jabin et al., 1997) by the sequence shown in Scheme 31, respectively. Because TBE-9 is much more potent than TBE-5, optically pure TBE-9 is one of the target compounds. Optically pure TBE-9 can be synthesized from optically pure 23 by the same synthetic route as for racemic TBE-9 (see Scheme 6) [5 steps from (−)-88a or (+)-88b].

Scheme 31ᵃ

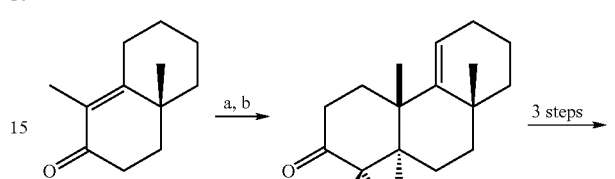

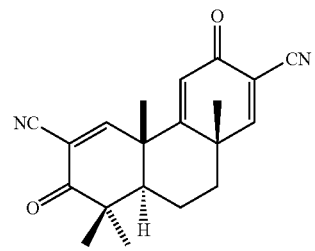

TBE-9

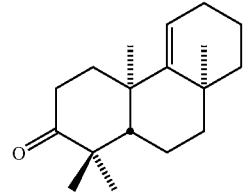

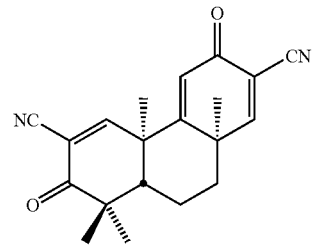

TBE-9

ᵃReagents: (a) NaH, DMSO, 1-chloro-3-pentanone; KOH, aq. MeOH;
(b) Li (4.5 eq.), H₂O (1 eq.), liq. NH₃, THF, CH₃I.

More recently, it has been reported that diastereomers 91a and 91b, resulting from ketalization of racemic 90 with 2(R), 3(R)-2,3-butanediol, are readily separable by column chromatography (Grieco et al., 1998). It is contemplated that optically pure 29c can be obtained via diastereomers 89a and 89b from racemic 29c using the same method (Scheme 32).

d. Design and Synthesis of Tricyclic Bis-Enones with Side Chains at C-13 and/or C-14

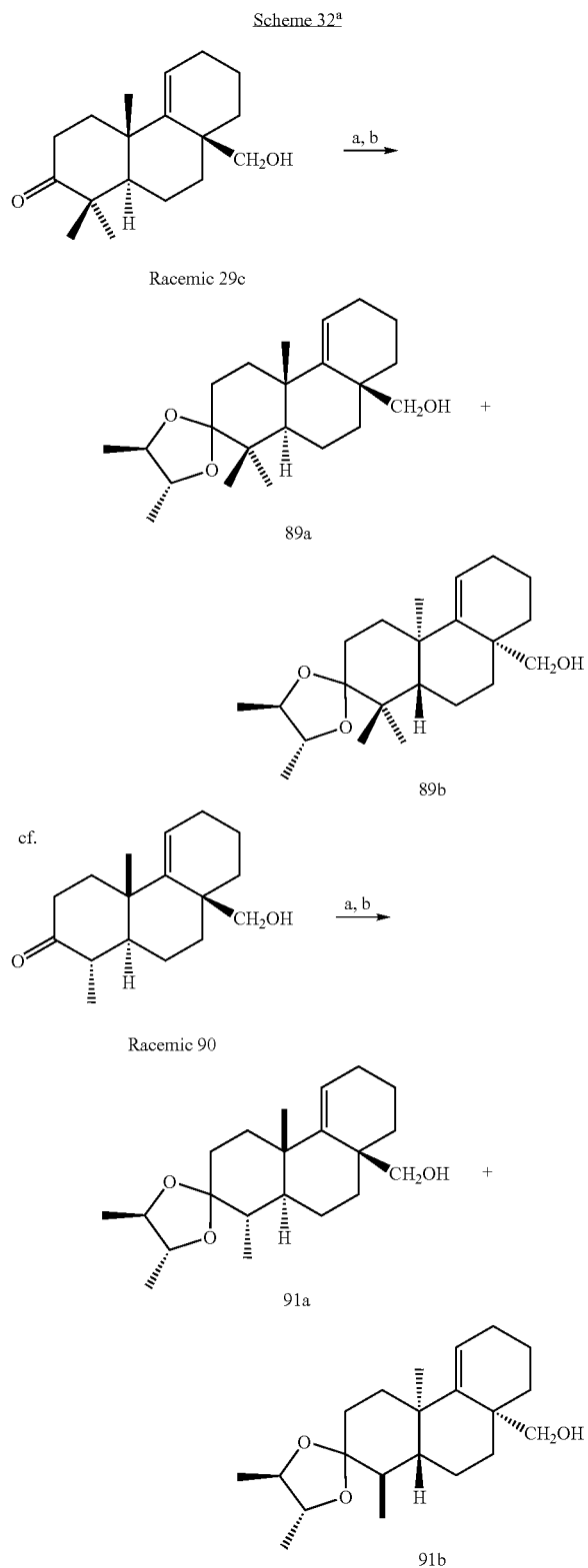

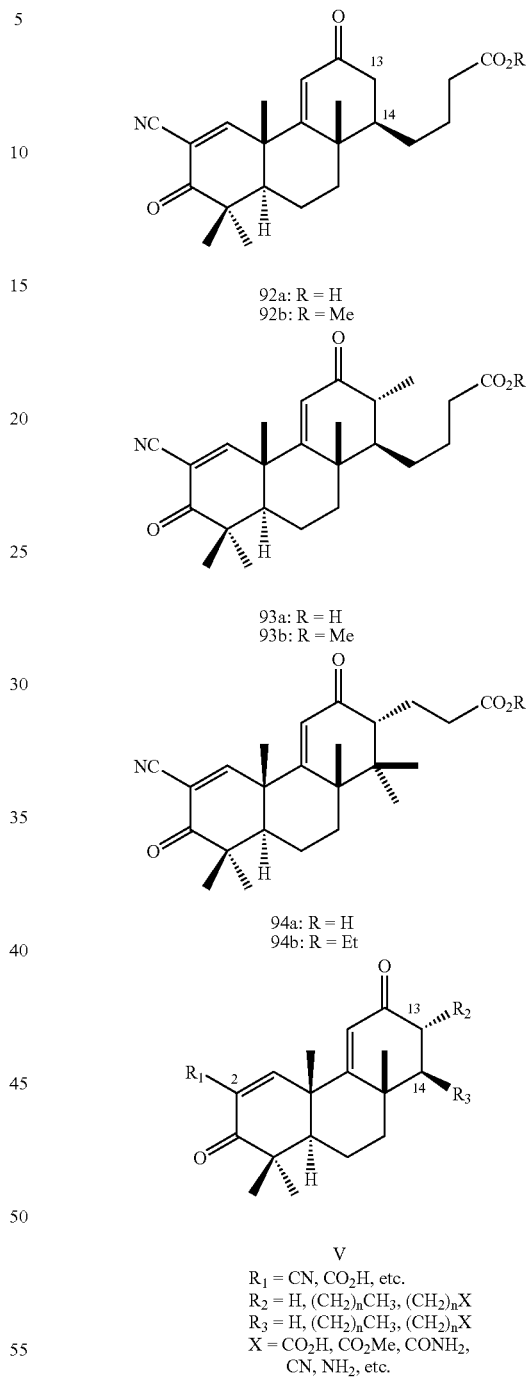

The inventors have designed TBEs 92-94 with side chains at C-13 and/or C-14. The specific synthetic routes of 92-94 are shown in Schemes 33-35. In Scheme 33, hydrogenation should take place from the α-face at the side chain double-bond of compound 95 due to steric hindrance. Therefore, compound 96 would be the predominant product. Similarly, in Scheme 34, compound 101 would be the predominant product. In Scheme 35, geminal methyl groups of 94 can be introduced by Simmons-Smith reaction, followed by hydrogenolysis (Oppolzer et al., 1978). It is contemplated that the sodium salts of 92a, 93a, and 94a will be water-soluble compounds.

Moreover, to optimize the length and functionality of the side chains at C-13 and/or C-14, TBEs of the general formula V are envisioned based on the structures of 92-94.

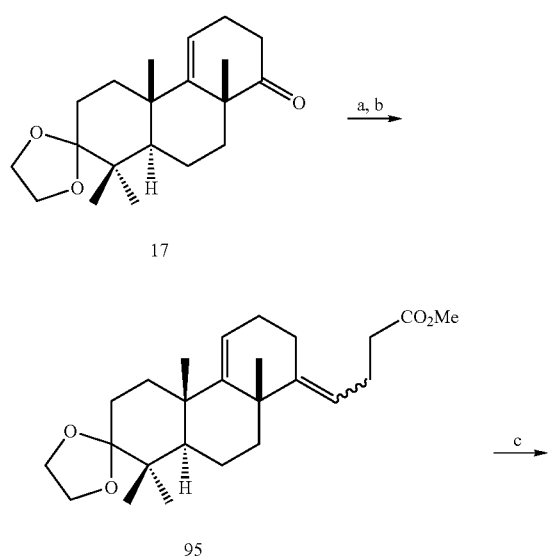

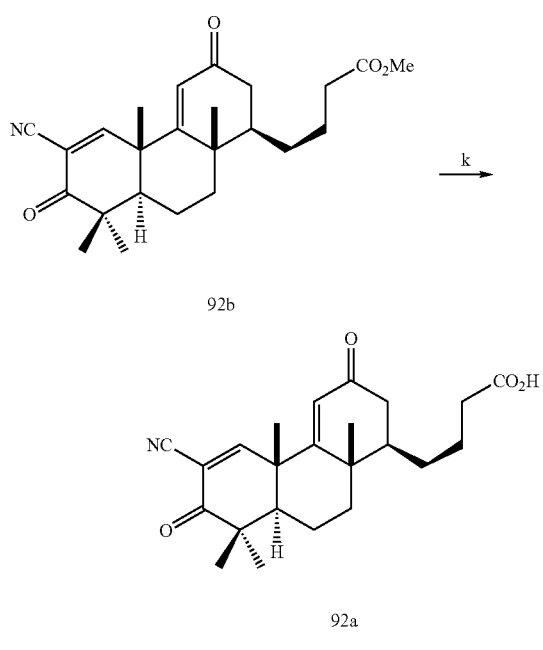

<sup>a</sup>Reagents: (a) Ph₃P(CH₂)₃CO₂HBr, NaH, DMSO; (b) CH₂N₂, Et₂O; (c) H₂, Pd/C; (d) PPTS, acetone, H₂O; (e) HCO₂Et, NaOMe, PhH; (f) NH₂OH·HCl, H₂O, EtOH; (g) NaOMe, Et₂O, MeOH; (h) LDA, p-TsCN; (i) DDQ, PhH; (j) CrO₃, t-BuO₂H; (k) KOH, H₂O, MeOH.

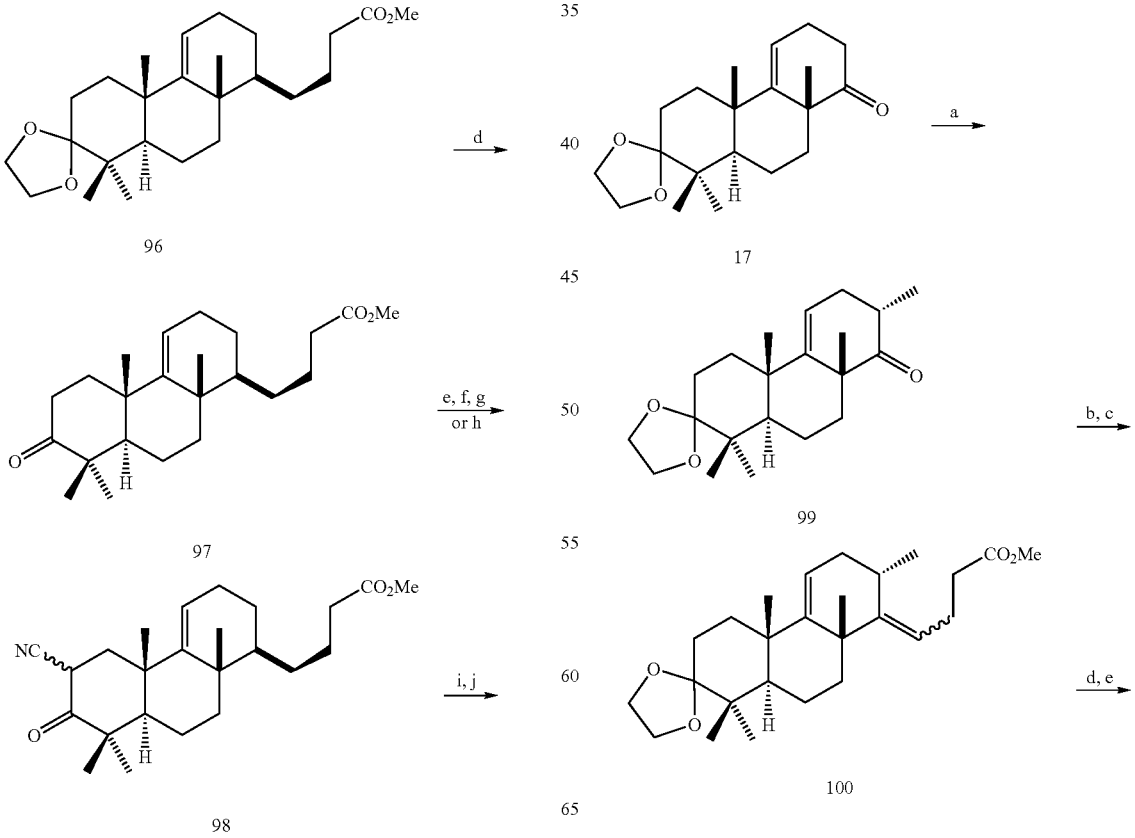

-continued
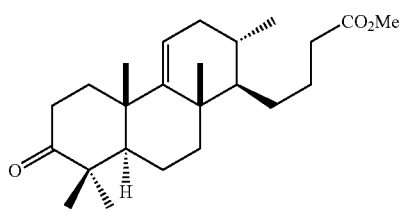
101
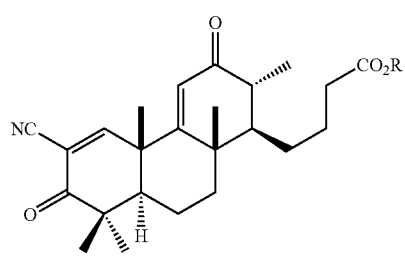
93b: R = Me
93a: R = H
aReagents: (a) CH₃I, LDA; (b) Ph₃P(CH₂)₃CO₂HBr, NaH, DMSO; (c) CH₂N₂, Et₂O; (d) H₂, Pd/C; (e) PPTS, acetone, H₂O; (f) LDA, p-TsCN; (g) DDQ, PhH; (h) CrO₃, t-BuO₂H; (i) KOH, H₂O, MeOH.
Scheme 35[a]
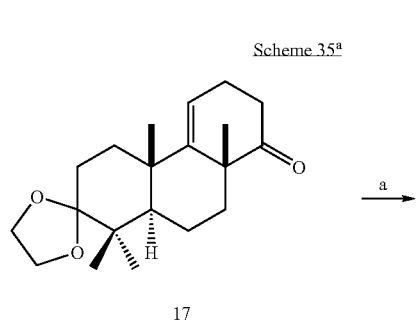
17
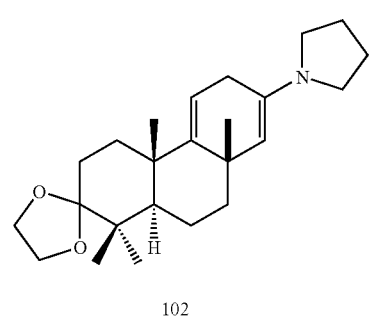
102
-continued
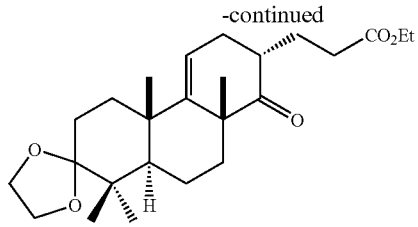
103
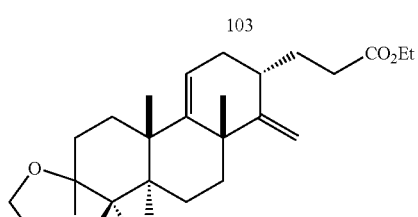
104
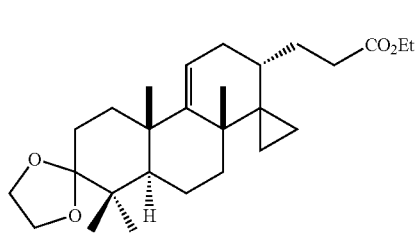
105
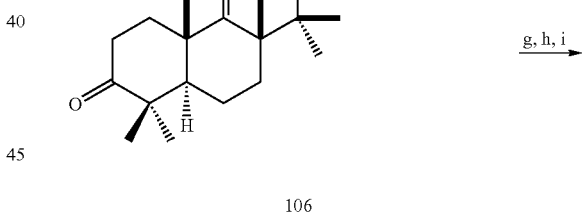
106
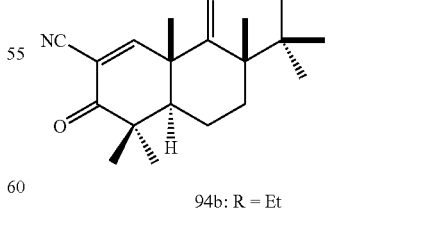
94a: R = H
94b: R = Et
[a] Reagents: (a) pyrrolidine, PhH; (b) CH₂=CH—CO₂Et, dioxane; (c) Ph₃PCH₂, (d) CH₂I₂, Zn-Cu; (e) H₂, PtO₂ (f) PPTS, acetone, H₂O; (g) LDA, p-TsCN; (h) DDQ, PhH; (i) CrO₃, t-BuO₂H; (j) KOH, H₂O, MeOH.

e. Design and Synthesis of TBEs with Modified Ring B

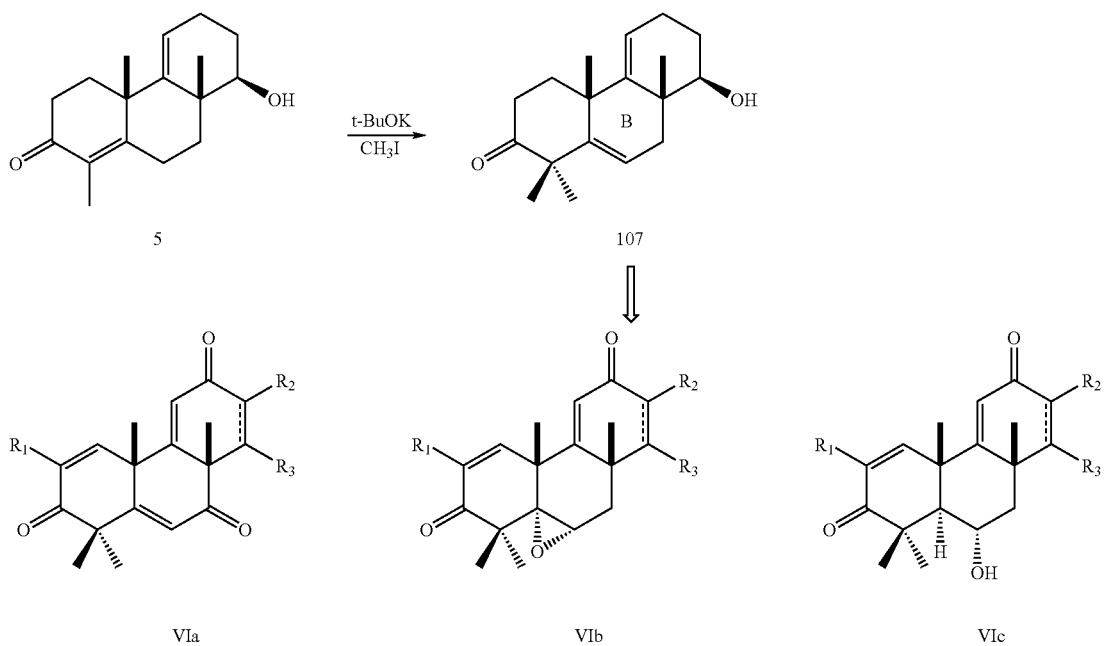

Using intermediate 107, which is synthesized from 5 with methyl iodide and potassium t-butoxide, TBEs with oxygenated functionalities in ring B having general formula VIa-c as shown above are envisioned and can be synthesized as discussed below. Insertion of oxygenated functionalities into ring B of TBEs is expected to improve their potency and pharmacokinetics because the balance between hydrophilicity and hydrophobicity is shifted. Proposed synthetic routes to specific compounds 108-110 are shown in Schemes 36 and 37. The inventors contemplate preparing both compounds 112 and 113 by selecting oxidation conditions. Compound 108 can be synthesized from 112. Epoxide 109 can be prepared by the same sequence using 113, followed by mCPBA oxidation. The mCPBA oxidation would give 109 predominantly because β-face of the $\Delta^5$ double-bond of 117 is more hindered than the α-face. In Scheme 37, hydroboration would give 119 mainly because the $\Delta^{9(11)}$ double-bond of 118 is seriously hindered and the β-face of the $\Delta^5$ double-bond is more hindered than the α-face. If these modifications increase the potency, the inventors contemplate designing and synthesizing water-soluble derivatives of these compounds with carboxyl and amino groups.

Scheme 36<sup>a</sup>

-continued

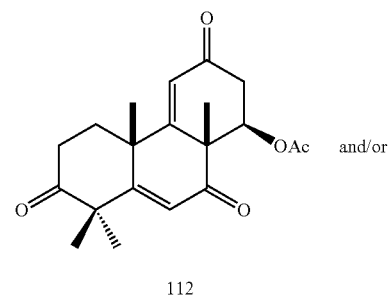 and/or

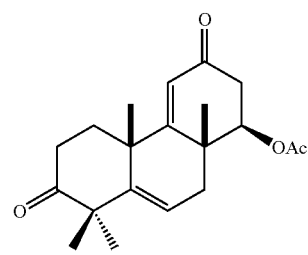

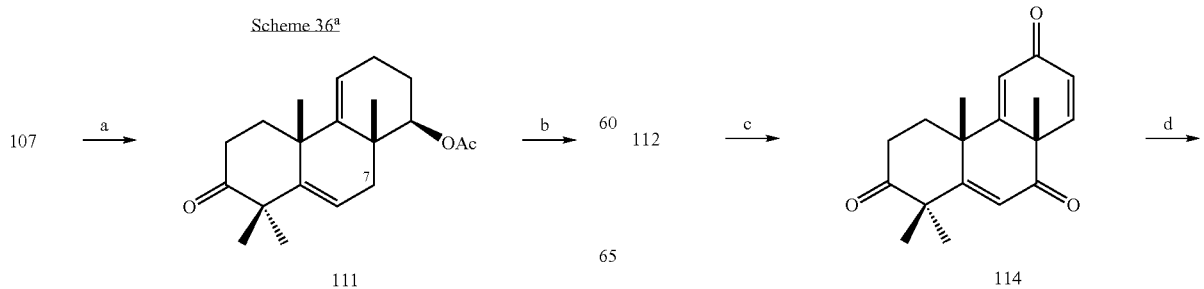

71

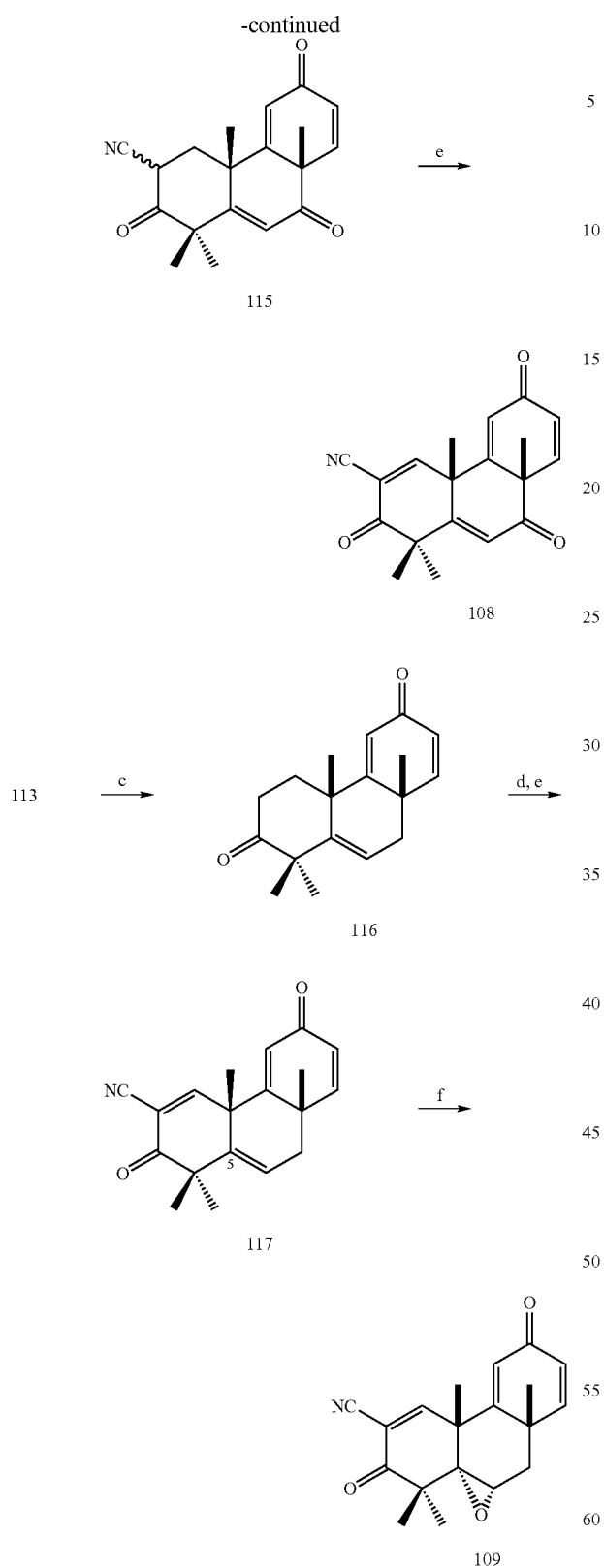

a Reagents: (a) Ac₂O, pyr.; (b) CrO₃, t-BuOOH, CH₂Cl₂ or CrO₃, pyr. CH₂Cl₂; (c) DBU, CH₂Cl₂; (d) p-TsCN, LDA; (e) DDQ, PhH (f) mCPBA

72

Scheme 37[a]

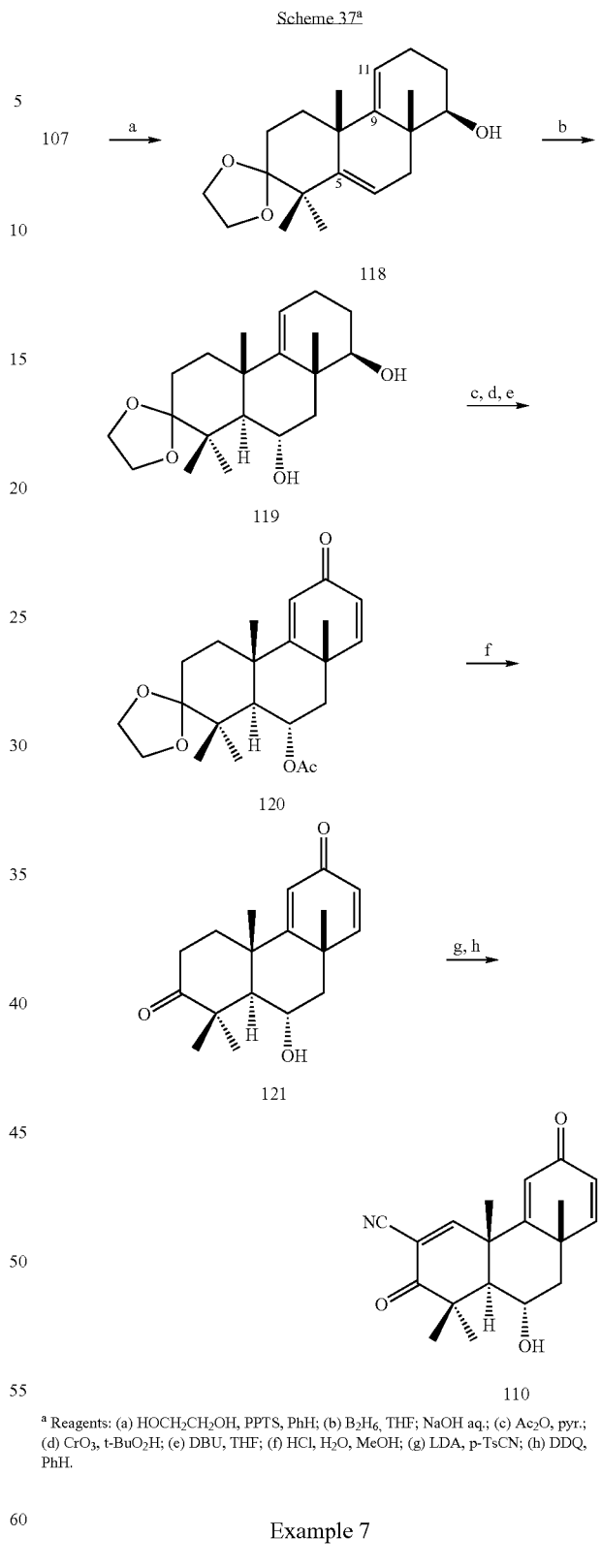

[a] Reagents: (a) HOCH₂CH₂OH, PPTS, PhH; (b) B₂H₆, THF; NaOH aq.; (c) Ac₂O, pyr.; (d) CrO₃, t-BuO₂H; (e) DBU, THF; (f) HCl, H₂O, MeOH; (g) LDA, p-TsCN; (h) DDQ, PhH.

Example 7

Biological Evaluation of iNOS Activation a. Reagents

Recombinant mice IFN-γ (LPS content, <10 pg/mL) were purchased from R & D systems (Minneapolis, Minn.). Polyclonal iNOS, IgG and peroxidase-conjugated secondary antibody were obtained from Santa Cruz (Santa Cruz, Calif.). All other chemicals were purchased from Sigma Chemical Co. (St. Louis, Mo.). Inhibitory test compounds were dissolved in DMSO before addition to cell cultures; final concentrations of inhibitory test compounds in DMSO were 0.1% or less. Controls with just DMSO were run in all cases.

b. Cell Culture

Female CD-1 mice, 5-10 weeks of age were obtained from the Charles River Breeding Laboratories (Wilmington, Mass.). To obtain primary macrophages, female CD-1 mice were injected intraperitoneally with 2 mL of 4% thioglycollate broth (Difco Laboratories, Detroit, Mich.). Four days after injection, peritoneal macrophages were harvested and processed according to Bogden et al. (1992). Cells were seeded in 96-well plates at $2 \times 10^5$ cells/well and incubated for 48 h with 10 ng/mL of IFN-γ in the presence or absence of inhibitory test compounds.

c. Measurement of Nitric Oxide (NO) Production in Mouse Macrophages

Nitrite accumulation was used as an indicator of NO production in the medium and was assayed by the Griess reaction. One hundred μL of Griess reagent was added to 100 μL of each supernatant from IFN-γ or inhibitory test compound-treated cells in triplicate. The plates were read at 550 nm against a standard curve of sodium nitrite. The protein determination was performed by Bradford protein assay (Ding et al., 1990).

d. SDS-PAGE and Western Blot Analyses of iNOS Protein in Primary Macrophages

For the evaluation of iNOS activation in vivo, female CD-1 mice were injected with 2 mL of 4% thioglycollate broth 3 days before IFN-γ stimulation. On day 3, test compounds were prepared in 0.1 mL volume of solvent mixture (DMSO: Ethanol:Water=2:2:1) and gavaged once to mice (6 per group). Then, 1 hr later, IFN-γ (0.5 μg/mouse) was given intraperitoneally. Ten hours after IFN-γ stimulation, mice were sacrificed, and peritoneal macrophages were collected and plated in 6-well plates. Cells were kept in incubators with 5% $CO_2$ at 37° C. for 12 hrs. The accumulation of nitric oxide in the supernatant was measured by the Griess reaction, as described above. To obtain total proteins, cells were washed and scraped into cold PBS, and then centrifuged at 500 g for 10 min at 4° C. The cell pellets were resuspended in 50 mM Tris-buffer (pH 7.4), and 100 mM NaCl, containing 0.5% of NP-40, 5 μg/mL of aprotinin, 10 μg/mL of leupeptin and 100 μM of PMSF, and then centrifuged to obtain whole cell lysates. The proteins (20-50 μg) were electrophoresed on 7.5% reducing SDS-PAGE and transferred in 20% methanol, 25 mM Tris, 192 mM glycine (pH 8.3) to 0.2 micron nitrocellulose membranes. The membranes were blocked with 5% non-fat milk in Tris-buffered saline (25 mM Tris, pH 7.5, 150 mM NaCl, 0.02% $NaN_3$) with 0.2% Tween-20 (Tween-TBS) for 1 h, then incubated with antibody to iNOS for 2-3 h, washed and finally incubated for 45 min with a 1:10,000 dilution of secondary antibody conjugated with horseradish peroxidase. The membranes were washed and then developed using a chemiluminescence system (enhanced chemiluminescence detection reagents; Amersham).

FIG. 5 shows the in vivo anti-inflammation activity of TBE-9 in CD-1 mice and demonstrates that TBE-9 blocks the activation of macrophages in mice.

Example 8

Biological Evaluation In Vitro and In Vivo of TBEs

Standard methodology already in place in the inventors laboratory (Suh et al., 1998, 1999, incorporated herein by reference) can be used to evaluate the biological activity of newly synthesized TBEs using suppression of de novo synthesis of iNOS and COX-2 as endpoints. Briefly, primary mouse macrophages or RAW264.7 cells can be cultured under standard conditions and stimulated with either interferon-γ or lipopolysaccharide (LPS). TBEs are added to cell cultures at the same time as inducers. Nitric oxide production in cell culture supernatants can be measured as nitrite accumulation by the Griess reaction. Analysis of levels of iNOS protein in lysates of primary macrophages or RAW cells can be done by Western blot analysis, while levels of iNOS mRNA can be done by routine Northern blot analysis. Prostaglandin E2 production is measured with a commercially available ELISA assay kit, and COS-2 protein and mRNA levels can measured by routine Western and Northern blot analysis, respectively. All these methods are well known in the art.

Assays are available to show activity in suppressing inflammation in vivo (ip, po and iv). The simplest assay for this purpose is to demonstrate that a new TBE can block the activation of macrophages (induced by interferon-γ) in the peritoneal cavity of mice. Mice will be injected ip with thioglycollate to stimulate the formation of macrophages, and these will be activated by ip injection of interferon-γ. A second in vivo system in which to text TBEs for suppression of macrophage activation is the granulomatous hepatitis model that has been used by Nathan and colleagues (Nicholson et al., 1999; MacMicking et al., 1995, all incorporated herein by reference). In this model, mice are injected ip with heat killed bacteria (*Proionabacterium acnes*), which results in the recruitment and activation of macrophages in the liver to form a granulomatous lesion. If such mice are challenged with LPS a week after injection with *Propionobacterium acnes*, they show a greatly enhanced response to LPS, as can be measured by high serum levels of nitrate plus nitrite (products of iNOS activity). The inventors will use TBEs to block the original formation of lesions in the liver as well as to block the response of activated liver macrophages to LPS. A third in vivo test is to evaluate the potency of TBEs against lethal inflammation of C57BL/6 mice caused by oral infection with *Toxoplasma gondii*. This model has been used by Dr. Kasper, Department of Medicine and Microbiology, Dartmouth Medical School, and colleagues (for example, Khan et al., 1997; Lee et al., 1999; Buzoni-Gatel et al., 1999; 2001, all incorporated herein by reference). Because overproduction of IFN-γ and synthesis of NO mediate this inflammation, inhibitors of production of NO like TBEs are expected to prevent early death in these mice.

Inhibitors of cell proliferation are known to be useful cancer chemopreventive and chemotherapeutic agents. The inventors contemplate testing TBE compounds for inhibition of proliferation of many malignant or premalignant cells (in vitro), e.g., human MCF-7 breast carcinoma, mouse L1210 leukemia, mouse B16 melanoma, and rat NRP-152 nonmalignant prostate epithelium. Furthermore, the inventors contemplate testing the TBE compounds in L1210 leukemia and B16 melanoma in vivo.

The inventors also contemplate long term in vivo assays of suppression of mammary or colon carcinogenesis in rats. The inventors have been actively engaged for the past 20 years in the rat model for breast cancer that employs nitrosomethylurea (NMU) as the carcinogen and it would be straightforward to determine if any new TBEs were active in this model.

Example 9

TBE Suppression of NF-κB Activation

Suppression of NF-κB activation by TBEs can be determined according to the methods described in Suh et al., (1998), incorporated herein by reference, using standard gel shift assays (EMSAs). Briefly, nuclear proteins can be extracted from macrophages or other cells by detergent lysis and then incubated with a $^{32}$P-labeled NF-κB oligonucleotide probe containing an NF-κB response element, followed by gel shift analysis. For the new TBEs, one can determine dose-response, kinetics of action, and interactions with other known effectors. Ability to block specific inducers of NF-κB activation, such as interferon-γ, TNF-α, LPS, phorbol ester, etc. can be measured. The inventors contemplate adopting two approaches in the study of effects of TBEs on events leading to the degradation of IκB and activation of NF-κB. These two well characterized kinases that lead to the phosphorylation of IκB, namely IKK (IκB kinase), which phosphorylates IκB directly, and NIK (NF-κB inducing kinase), which can phosphorylate IKK to enhance its kinase activity.

The first approach is to use natural inducers such as IL-1β, TNF-α, or LPS to treat different cell lines. Lysates can be harvested and IKK will be immunoprecipitated. Using an in vivo kinase assay, recombinant GST-IκB (1-62) protein can be used to detect the activity of IKK, with or without treatment with TBEs.

Phosphorylated GST-IκB can be detected either using $^{32}$P-labeled ATP in kinase assay, or using a phospho-IκB specific antibody through Western analysis.

The second approach is to transfect IKK expression vectors in HeLa cells, with or without added NIK expression vectors. After immunoprecipitation with an antibody against HA, IKK activities in the absence (basal activity) or presence (induced activity) of NIK can be measured as detailed above. The inventors also contemplate studying the effects of TBEs on these transfected kinase activities. Detailed methods for all of the above have been published by Rossi et al. (2000), the entire contents of which are incorporated herein by reference.

Example 10

Clinical Trials

This example is concerned with the development of human treatment protocols using the TBE compounds and analogs and especially the pharmaceutical formulations thereof. These compositions will be of use in the clinical treatment of various cancers, neurodegenerative diseases or inflammatory diseases. Although, the section below discusses cancers, one of skill in the art will recognize that this general scenario can be used for any of the diseases described in the specification that involve excessive NO or prostaglandin production.

The various elements of conducting a clinical trial, including patient treatment and monitoring, will be known to those of skill in the art in light of the present disclosure. The following information is being presented as a general guideline for use in establishing clinical trials using the compositions of the present invention.

Candidates for the phase 1 clinical trial will be patients on which all conventional therapies have failed. Pharmaceutical formulations of the TBE compounds will be administered to them intravenously on a tentative schedule of 5 days every 4 weeks. One of skill in the art will appreciate that one may administer the therapeutic formulation of the invention by any alternative route that is suitable depending on the nature of the lesion including administration by any method including local, regional, or systemic administration. Oral and topical applications are also contemplated. A composition of the present invention is typically administered orally or parenterally in dosage unit formulations containing standard, well known non-toxic physiologically acceptable carriers, adjuvants, and vehicles as desired. The term parenteral as used herein includes subcutaneous injections, intravenous, intramuscular, intra-arterial injection, or infusion techniques.

To monitor disease course and evaluate the anti-tumor responses, it is contemplated that the patients should be examined for appropriate tumor markers every month. To assess the effectiveness of the drug, the following parameters will be monitored: tumor size and/or bone marrow infiltration of the cancer cells. Tests that will be used to monitor the progress of the patients and the effectiveness of the treatments may include: physical exam, X-ray, blood work and other clinical laboratory methodologies. The doses given in the phase 1 study will be escalated as is done in standard phase 1 clinical phase trials, i.e. doses will be escalated until maximal tolerable ranges are reached.

Clinical responses may be defined by acceptable measure. For example, a complete response may be defined by complete disappearance of evidence of cancer cells for at least 2 months. Whereas a partial response may be defined by a 50% reduction of cancer cells for at least 2 months.

The clinical trials may be performed with the therapeutic agents of the invention alone or in combination with other anti-cancer drugs and other standard cancer therapies used in the art. The therapeutic compositions of the invention may be delivered to the patient before, after or concurrently with the other anti-cancer agents.

The typical course of treatment will vary depending upon the individual patient and disease being treated in ways known to those of skill in the art. For example, a patient with leukemia might be treated in four week cycles, although longer duration may be used if adverse effects are observed with the patient, and shorter terms of treatment may result if the patient does tolerate the treatment as hoped. Each cycle will consist of 5 individual doses, although this too may be varied depending on the clinical situation. Upon election by the clinician the regimen may be continued with 5 doses every three weeks or on a less frequent basis. Of course, these are only exemplary times for treatment, and the skilled practitioner will readily recognize that many other time-courses are possible.

Patients may, but need not, have received previous chemo-, radio- or gene therapeutic treatments. Optimally the patient will exhibit adequate bone marrow function (defined as peripheral absolute granulocyte count of >2,000/mm3 and platelet count of 100,000/mm3, adequate liver function (bilirubin 1.5 mg/dl) and adequate renal function (creatinine 1.5 mg/dl).

In one embodiment, administration simply entails injection of the therapeutic composition into the tumor. In another embodiment, a catheter is inserted into the site of the tumor and the cavity may be continuously perfused for a desired period of time.

Of course, the above-described treatment regimes may be altered in accordance with the knowledge gained from preclinical trials. Those of skill in the art will be able to take the information disclosed in this specification and optimize treatment regimes based on the clinical trials described in the specification.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, and those listed in the Appendix, to the extent that they provide exemplary procedural or other details supplementary to those set forth herein, are specifically incorporated herein by reference.

U.S. Pat. No. 4,395,423
U.S. Pat. No. 4,683,195
U.S. Pat. No. 6,025,395
U.S. Pat. No. 6,326,507
Ausubel et al., In: *Current Protocols in Molecular Biology*, John, Wiley & Sons, Inc, NY, 1994.
Baeuerle, *Cell*, 87:13-20, 1996.
Bagasra et al., *Proc. Natl. Acad. Sci. USA*, 92(26):12041-12045, 1995.
Baldwin, *Annu. Rev. Immunol.*, 14649-681, 1996.
Bargou et al., *J. Clin. Invest.*, 100:2961-2969, 1997.
Barkett and Golmore, *Oncogene*, 18:6910-6924, 1999.
Barnes and Karin, *N. Engl. J. Med.*, 336:1066-1071, 1997.
Beal, *Curr. Opin. Neurobiol.*, 6(5):661-666, 1996.
Bogdan et al., *J. Biol. Chem.*, 267:23301-23308, 1992.
Boolbol et al., *Cancer Res.*, 56(11):2556-2560, 1996.
Buzoni-Gatel et al., *Gastroenterology*, 120:914-924, 2001.
Buzoni-Gatel et al, *J. Immunol.*, 162:5846-5852, 1999.
Caine, In: *Organic Reactions*; John Wiley & Sons, Inc., NY, 23:258, 1976.
Clinton et al., *J. Am. Chem. Soc.*, 83:1478-1491, 1961.
Coyle and Puttfarcken, *Science*, 262(5134):689-695, 1993.
Culver et al., *Science*, 256(5063):1550-1552, 1992.
Dale et al., *J. Org. Chem.*, 34:2543-2549, 1969.
Dean et al., *Lancet*, 2(7416):769-770, 1965.
Ding et al., *J. Immunol.*, 940-944, 1990.
DuBios et al., *Gastroenterology*, 110:1259-1262, 1996.
DuBois et al., *Cancer Res.*, 56(4):733-737, 1996.
Dutcher et al., *J. Org. Chem.*, 41:2663-2669, 1976.
Finkbeiner et al., *J. Am. Chem. Soc.*, 85:616-622, 1963.
Gait et al., In: *Oligonucleotide Synthesis*, 1984.
Genain and Hauser, *J. Mol. Med.*, 75(3):187-197, 1997.
Ghosh et al., *Annu Rev Immunol.*, 16:225-60, 1998.
Glover, In: *DNA Cloning*, Volumes I and II, 1985
Grieco et al., *J. Org. Chem.*, 63:5929-5936, 1998.
Guttridge et al.i, *Mol. Cell. Biol.*, 19:5785-5799, 1999.
Hagiwara et al., *J. Org. Chem.*, 53:2308-2311, 1988.
Hames and Higgins, In: *Nucleic Acid Hybridization*, 1984.
Heathcock et al., *J. Org. Chem.*, 49:3264-3274, 1984.
Hinz et al.i, *Mol. Cell. Biol.*, 19:2690-2698, 1999.
Hirota et al., *Agric. Biol. Chem.*, 54:1073-1075, 1990.
Hirota et al., *Bull. Chem. Soc. Jpn.*, 61:4023-4028, 1988.
Hirota et al., *J. Org. Chem.*, 56:1119-1127, 1991.
Honda et al., *Chem. Lett.*, 299-302, 1981.
Honda et al., *J. Med. Chem.*, 43:4233-4246, 2000.
Honda, et al., *J. Med. Chem.*, 43:1866-1877, 2000.
Huang et al., *Cancer Res.*, 54:701-708, 1994.
Huang et al., *Nat. Struct. Biol.*, 7:634-638, 2000.
Javin et al., *Tetrahedron Asym.* 8:1101-1109, 1997.
Johnson et al. *J. Am. Chem. Soc.*, 67:1745-1754, 1945.
Joyce et al., *J. Biol. Chem.*, 274:25245-25249, 1999.
Kahne and Collum, *Tetrahedron Lett.*, 22:5011-5014, 1981.
Kaltschmidt et al., *Proc. Natl. Acad. Sci. USA*, 94(6):2642-2647, 1997.
Kerwin et al., *J. Org. Chem.*, 52:1686-1695, 1987.
Khan et al., *Proc. Natl. Acad. Sci. USA*, 94:13955-13960, 1997.
Lee et al., *Experimental Parasitology*, 91:212-221, 1999.
MacMicking et al., *Cell*, 81:641-650, 1995.
Marnett, *Cancer Res.*, 52(20):5575-5589, 1992.
Mayer and Walker, In: *Methods In Enzymology*, Academic Press, Inc., NY, 1987.
McGeer and McGeer, *Brain Res. Brain Res. Rev.*, 21(2):195-218, 1995.
McGeer et al., *Neurology*, 47(2):425-432, 1996.
Merrill and Benvenist, *Trends Neurosci.*, 19(8):331-338, 1996.
Miller, In: *Experiments in Molecular Genetics*, Cold Spring Harbor Press, Cold Spring Harbor, N.Y., 1972.
Moncada et al.i, *Pharmacol. Rev.*, 43:109-141, 1991.
Muzart, *Tetrahedron Lett.*, 28:4665-4668, 1987.
Nathan and Xie, *Cell*, 78:915-918, 1994.
Nicholson et al., *Shock*, 11:253-258, 1999.
Nishino et al., *Cancer Res.*, 48:5210-5215, 1988.
Ohshima and Bartsch, *Mutat. Res.*, 305:253-264, 1994.
Oppolzer and Godel, *J. Am. Chem. Soc.*, 100:2583-2584, 1978.
Oshima et al., *Cell*, 87(5):803-809, 1996.
Pahl, *Oncogene*, 18:6853-6866, 1999.
Prescott and White, *Cell*, 87(5):783-786, 1996.
Rasmussen et al., *J. Org. Chem.*, 46:4843-4846, 1981.
Rayet and Gelinas, *Oncogene*, 18:6938-6947, 1999.
Reddy et al., *Cancer Res.*, 56(20):4566-4569, 1996.
Rossi et al., *Nature*, 403:103-108, 2000.
Salvemini et al., *J. Clin. Invest.*, 93:1940-1947, 1994.
Sambrook. et. al., In: *Molecular Cloning: A Laboratory Manual*, $2^{nd}$. Ed., Cold Spring Harbor Laboratory Press, Cold Spring Harbor, N.Y., 1989.
Sheng et al., *Gastroenterology*, 113(6):1883-18891, 1997.
Simonian and Coyle, *Annu. Rev. Pharmacol. Toxicol.*, 36:83-106, 1996.
Singh et al., *J. Pharm. Pharmacol.*, 44:456-458, 1992.
Snitman et al., *Synth. Comm.*, 8:187-194, 1978.
Sporn and Roberts, *J. Cvlin. Invest.*, 78:329-332, 1986.
Srikrishna et al., *Tetrahedron*, 54:11517-11524, 1998.
Stewart et al., *Neurology*, 48(3):626-632, 1997.
Stork et al., *J. Am. Chem. Soc.*, 85:207-222, 1963.
Strejan et al., *J. Neuroimmunol.*, 7:27, 1984.
Suh et al, *Cancer Res.*, 59(2):336-41, 1999.
Suh et al., *Cancer Research*, 58:717-723, 1998.
Takahashi et al.i, *Cancer Res.*, 57:1233-1237, 1997.
Tamir and Tannebaum, *Biochim. Biophys. Acta*, 1288:F31-F36, 1996.
Tsujii and DuBois, *Cell*, 83(3):493-501, 1995.
Vodovotz et al., J. Exp. Med., 184(4):1425-1433, 1996.
Weir and Blackerll, In: *Handbook Of Experimental Immunology*, Volumes I-IV, 1986.
Williams et al., *Clin. Neurosci.*, 2(3-4):229-245, 1994.

What is claimed is:

1. A method of suppressing the expression of iNOS or COX-2 genes in a subject comprising administering to the subject an effective amount of a pharmaceutical composition comprising a compound of formula:

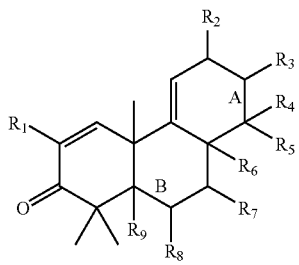

wherein $R_1$ is CN, or $CO_2H$;
$R_2$ is $=O$;
$R_3$ is H, $CH_3$, $CO_2H$, $CO_2Me$, $CONH_2$, CN, or $(CH_2)_n$—$R_{10}$;
$R_4$ is H, OH, OAc, $CH_3$, $CO_2H$, $CO_2Me$, $CONH_2$, CN, or $(CH_2)_n$—$R_{10}$;
$R_5$ is H, $CH_3$, $CH_2CH_3$, or part of a double-bond A;
$R_6$ is H, $CH_3$, $CO_2H$, $CO_2Me$, $CONH_2$, CN, $CH_2X$, $CH_2OAc$, $CH_2OH$, CHO, $CH_2NH_2$, or $(CH_2)_n$—$R_{10}$, $CH_2OSiMe_2$(t-Bu), $CONR_{11}R_{12}$, or $CH_2NHCOO$(t-Bu);
$R_7$ is H, or $=O$;
$R_8$ is H, OH, forms an epoxide with $R_9$; or forms part of double-bond B;
$R_9$ is H, forms an epoxide with $R_8$, or forms part of double-bond B;
$R_{10}$ is $CH_3$, $CO_2H$, $CO_2CH_3$, $CO_2CH_2CH_3$, $CONH_2$, CN, $NH_2$, $CH(CH_3)_2$, $NR_{11}R_{12}$, pyrrolidine, piperidine, pyrazine, imidazole, pyrazole, triazole, tetrazole, substituted at N with $R_{13}$, or 1,4-oxazine, where $R_{11}$, $R_{12}$, and $R_{13}$ are alkyl;
X is F, Cl, or Br;
n is 0-20; and
A & B independently signify a single- or double-bond;
or an optically active form (−)−, (+)−, thereof; or a (±) racemic form thereof;
or a pharmaceutically acceptable salt thereof.

2. The method of claim 1, wherein said compound is optically pure.

3. The method of claim 1, wherein said compound is predominantly the (+) enantiomer.

4. The method of claim 1, wherein said compound is predominantly the (−) enantiomer.

5. The method of claim 1, wherein said compound is a racemic mixture.

6. A method of inhibiting excessive nitric oxide or prostaglandin formation in a subject comprising administering to the subject an effective amount of a pharmaceutical composition comprising a compound of the formula:

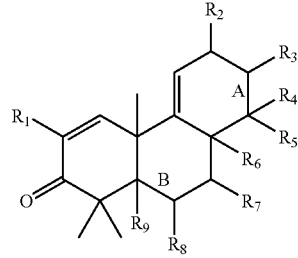

wherein $R_1$ is CN, or $CO_2H$;
$R_2$ is $=O$;
$R_3$ is H, $CH_3$, $CO_2H$, $CO_2Me$, $CONH_2$, CN, or $(CH_2)_n$—$R_{10}$;
$R_4$ is H, OH, OAc, $CH_3$, $CO_2H$, $CO_2Me$, $CONH_2$, CN, or $(CH_2)_n$—$R_{10}$;
$R_5$ is H, $CH_3$, $CH_2CH_3$, or part of a double-bond A;
$R_6$ is H, $CH_3$, $CO_2H$, $CO_2Me$, $CONH_2$, CN, $CH_2X$, $CH_2OAc$, $CH_2OH$, CHO, $CH_2NH_2$, or $(CH_2)_n$—$R_{10}$, $CH_2OSiMe_2$(t-Bu), $CONR_{11}R_{12}$, or $CH_2NHCOO$(t-Bu);
$R_7$ is H, or $=O$;
$R_8$ is H, OH, forms an epoxide with $R_9$; or forms part of double-bond B;
$R_9$ is H, forms an epoxide with $R_8$, or forms part of double-bond B;
$R_{10}$ is $CH_3$, $CO_2H$, $CO_2CH_3$, $CO_2CH_2CH_3$, $CONH_2$, CN, $NH_2$, $CH(CH_3)_2$, $NR_{11}R_{12}$, pyrrolidine, piperidine, pyrazine, imidazole, pyrazole, triazole, tetrazole, substituted at N with $R_{13}$, or 1,4-oxazine, where $R_{11}$, $R_{12}$, and $R_{13}$ are alkyl;
X is F, Cl, or Br;
n is 0-20; and A & B independently signify a single- or double-bond;
or an optically active form (−)−, (+)−, thereof; or a (±) racemic form thereof;
or a pharmaceutically acceptable salt or formulation thereof.

7. The method of claim 6, wherein said compound is optically pure.

8. The method of claim 6, wherein said compound is predominantly the (+) enantiomer.

9. The method of claim 6, wherein said compound is predominantly the (−) enantiomer.

10. The method of claim 6, wherein said compound is a racemic mixture.

* * * * *

UNITED STATES PATENT AND TRADEMARK OFFICE
CERTIFICATE OF CORRECTION

PATENT NO. : 7,678,830 B2
APPLICATION NO. : 11/672449
DATED : March 16, 2010
INVENTOR(S) : Tadashi Honda et al.

Page 1 of 1

It is certified that error appears in the above-identified patent and that said Letters Patent is hereby corrected as shown below:

In title page, item (56) References Cited - Other Publications, insert:
--Karin, "Nuclear factor-kappaB in cancer development and progression," *Nature*, 441:431-436, 2006.--.

In claim 1, column 79, line 3, delete "$COX_{-2}$" and insert -- COX-2 -- therefor.

Signed and Sealed this

First Day of June, 2010

David J. Kappos
*Director of the United States Patent and Trademark Office*